(12) United States Patent
Gao et al.

(10) Patent No.: US 9,567,464 B2
(45) Date of Patent: Feb. 14, 2017

(54) DISPERSE DYES, THEIR PREPARATION AND THEIR USE

(71) Applicant: DyStar Colours Distribution GmbH, Raunheim (DE)

(72) Inventors: Yongnian Gao, Singapore (SG); Si Sl Liew, Singapore (SG); Samuel Shantong Fu, Singapore (SG); Roxana Barbieru, Singapore (SG)

(73) Assignee: DyStar Colours Distribution GmbH (DE)

( * ) Notice: Subject to any disclaimer, the term of this patent is extended or adjusted under 35 U.S.C. 154(b) by 0 days.

(21) Appl. No.: 15/032,869

(22) PCT Filed: Oct. 22, 2014

(86) PCT No.: PCT/EP2014/072654
§ 371 (c)(1),
(2) Date: Apr. 28, 2016

(87) PCT Pub. No.: WO2015/062937
PCT Pub. Date: May 7, 2015

(65) Prior Publication Data
US 2016/0280922 A1   Sep. 29, 2016

(30) Foreign Application Priority Data

Oct. 29, 2013 (EP) .................................. 13190666

(51) Int. Cl.
| | | |
|---|---|---|
| *C09B 29/42* | (2006.01) | |
| *C09B 29/36* | (2006.01) | |
| *C09B 29/46* | (2006.01) | |
| *C07D 215/38* | (2006.01) | |
| *C07D 417/12* | (2006.01) | |
| *C07D 409/12* | (2006.01) | |
| *C07D 401/12* | (2006.01) | |

(52) U.S. Cl.
CPC ......... *C09B 29/3617* (2013.01); *C07D 215/38* (2013.01); *C07D 401/12* (2013.01); *C07D 409/12* (2013.01); *C07D 417/12* (2013.01); *C09B 29/3652* (2013.01); *C09B 29/3682* (2013.01); *C09B 29/3686* (2013.01); *C09B 29/3691* (2013.01)

(58) Field of Classification Search
CPC ............. C09B 29/3617; C09B 29/3691; C09B 29/3652; C09B 29/3686; C09B 29/3682
See application file for complete search history.

(56) References Cited

U.S. PATENT DOCUMENTS

| | | |
|---|---|---|
| 3,699,092 A | 10/1972 | Weaver et al. |
| 5,179,207 A | 1/1993 | Krutak et al. |
| 2006/0141203 A1 | 6/2006 | Monden et al. |

FOREIGN PATENT DOCUMENTS

| | | | |
|---|---|---|---|
| DE | 2640624 A1 * | 3/1977 | ......... C09B 29/0085 |
| DE | 2640624 A1 | 3/1977 | |
| EP | 1 154 774 A1 | 11/2001 | |
| JP | 2005305835 A | 11/2005 | |
| WO | WO-0047212 A1 | 8/2000 | |
| WO | WO-2008/034650 A1 | 3/2008 | |
| WO | WO-2009/036351 A2 | 3/2009 | |

OTHER PUBLICATIONS

International Search Report for PCT/EP2014/072654 mailed Jun. 1, 2015.

* cited by examiner

*Primary Examiner* — Joseph Kosack
(74) *Attorney, Agent, or Firm* — Drinker Biddle & Reath LLP

(57) ABSTRACT

The present invention refers to dyes of the formula (I) and mixtures thereof

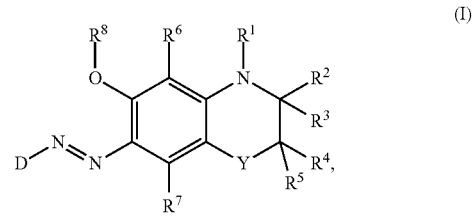

a process for their production and to their use.

19 Claims, 2 Drawing Sheets

DISPERSE DYES, THEIR PREPARATION AND THEIR USE

CROSS-REFERENCE TO RELATED APPLICATIONS

This application is a national stage application (under 35 U.S.C. §371) of PCT/EP2014/072654, filed Oct. 22, 2014, which claims benefit of European Application No. 13190666.1, filed Oct. 29, 2013, both of which are incorporated herein by reference in their entirety.

The present invention relates to disperse azo dyes comprising tetrahydroquinoline derivatives as coupling components, a process for the preparation of such dyes and the use thereof in dyeing or printing semi-synthetic and synthetic hydrophobic fibre materials, especially textile materials.

Azo compounds derived from substituted tetrahydroquinoline derivatives as coupling components are known to be used as intermediates for photoactivatable dyes used for non-textile applications such as cell staining (e.g. WO 2009/036351), dyes for photosensitive materials (e.g. JP2005/305835) or cationic dyes for dyeing keratin fibres (e.g. WO 2008/034650). Also a specific group of Thioazolyl-azo-tetrahydroquinolines is know to be useful for textile dyeing from U.S. Pat. No. 3,699,092. And structures

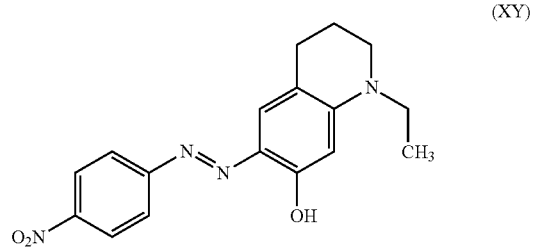

(XY)

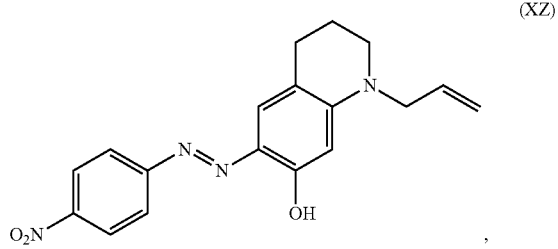

(XZ)

are disclosed in WO 2009/036351 on page 13 and 24 respectively as intermediates to photoactivatable dyes. However, in use for textile dyeing—and for red dyes in particular—are structures such as

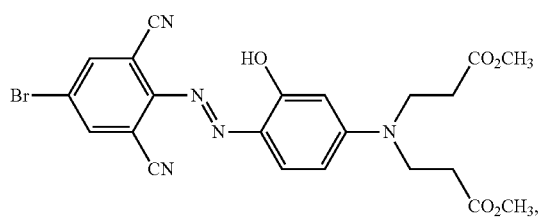

(xc1)

which is commonly known as C. I. Disperse Red 369 or dyes based on the following chemical compound:

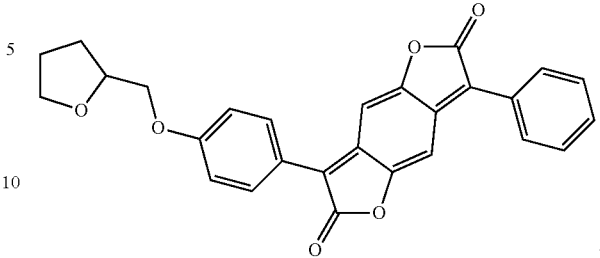

(xc2)

Surprisingly, it has now been found that disperse dyes of formula (I) show highly advantageous properties over the known disperse dyes for dyeing and printing textile materials. The superior properties include excellent wet contact fastness properties, good build-up, sublimation and light fastness properties both in the exhaust and thermosol process, and in textile printing.

The present invention refers to dyes of the formula (I) and mixtures thereof:

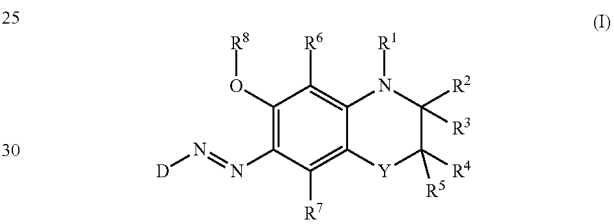

(I)

wherein
Y is a group of general formula (II) to (IV)

(II)

(III)

(IV)

$R^1$ is alkyl, alkenyl, cycloalkyl, aryl, heteroaryl, heterocycloalkyl
or
alkyl interrupted by one or more heteroatoms selected from the group consisting of oxygen and sulphur
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$ or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$, $R^2$ to $R^8$ independent of each other is hydrogen, alkyl, aryl, alkoxyl, cycloalkyl, halogen or alkyl interrupted by one or more heteroatoms selected from the group consisting of oxygen and sulphur or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$ or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$, $R^9$ is alkyl, aryl, cycloalkyl, alkyl interrupted by one or more heteroatoms selected from the group consisting of oxygen and sulphur
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$,
or
alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$
or
aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$, D represents a group of formula (VI)

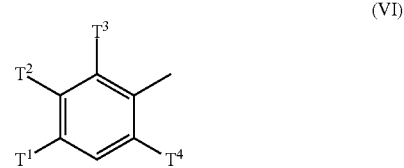

(VI)

wherein
$T^1$ to $T^4$ independent from each other is
hydrogen, alkyl, cycloalkyl, alkenyl, alkynyl, aryl, alkoxyl, halogen, cyano, nitro, acyl, aryloyl, arylsulfonyl, alkylsulfonyl, N-monoalkyl-sulfamoyl, N,N-dialkyl-sulfamoyl, alkoxylcarbonyl, aryloxycarbonyl, N-monoalkyl-carbamoyl, N,N-dialkyl-carbamoyl, aryloyloxy, acyloxy, aryloxy, thiocyano, hydroxyl, arylmethoxy, arylsulphonyloxy, alkylsulphonyloxy, aryloxysulfonyl, -[(alkoxycarbonyl)-methoxyl]carbonyl, [(aryloxycarbonyl)-methoxyl]carbonyl, [(alkylacyl)-methoxy]carbonyl, [(arylacyl)-methoxy]carbonyl, trifluoromethyl
or
alkyl interrupted by one or more heteroatoms selected from the group consisting of oxygen and sulfur
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$
or
alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, whereby at least one of $T^1$, $T^2$, $T^3$ and $T^4$ is not hydrogen or D represents a group of formula (VII)

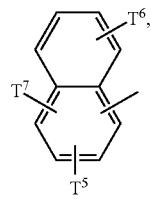

(VII)

wherein $T^5$ to $T^7$ independent from each other is hydrogen, alkyl, cycloalkyl, alkenyl, alkynyl, aryl, alkoxyl, halogen, cyano, nitro, acyl, arylacyl, alkoxycarbonyl, aryloxycarbonyl, [(alkoxycarbonyl)-methoxyl]carbonyl, [(aryloxycarbonyl)-methoxyl]carbonyl, [(alkylacyl)-methoxy]carbonyl, [(arylacyl)-methoxy]carbonyl, N-monoalkyl-carbamoyl, N,N-dialkyl-carbamoyl or alkyl interrupted by one or more heteroatoms selected from the group consisting of oxygen and sulfur or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N- monoarylsulfamoyl, arylsulphonyloxy, alkylsulphonyloxy, aryloxysulfonyl, alkoxylsulfonyl and COOR$^{12}$,
whereby at least one of T$^5$, T$^6$ and T$^7$ is not hydrogen,
or
D represents a group of the formula (VIII)

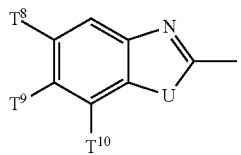

(VIII)

wherein
U is oxygen, sulphur or N—R$^{15}$,
T$^8$ and T$^{10}$ independent of each other is hydrogen, fluorine, chlorine or bromine,
T$^9$ is hydrogen, alkylsulfonyl, thiocyano, alkoxy, halogen or nitro,
R$^{15}$ is alkyl, aryl or cycloalkyl,
or
D represents a group of the formula (IX)

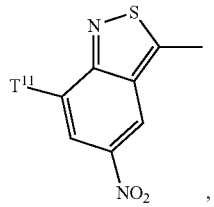

(IX)

wherein
T$^{11}$ is hydrogen, nitro or halogen,
or
D represents a group of the formula (X)

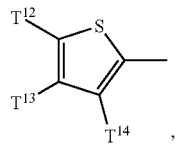

(X)

wherein
T$^{12}$ and T$^{14}$ independent from each other is nitro, cyano, acyl or alkoxycarbonyl,
T$^{13}$ is hydrogen, aryl, alkyl, halogen
or
alkyl interrupted by one or more heteroatoms selected from the group consisting of oxygen and sulfur
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, het-
eroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$
or
alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoaryl-sulfamoyl, arylsulphonyloxy, alkylsulphonyloxy, aryloxysulfonyl, alkoxylsulfonyl and COOR$^{12}$
or
aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$,
or
D represents a group of the formula (XI)

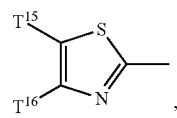

(XI)

wherein
T$^{15}$ and T$^{16}$ independent from each other is hydrogen, halogen, alkyl, nitro, cyano, acyl, alkoxycarbonyl, aryl
or
alkyl interrupted by one or more heteroatoms selected from the group consisting of oxygen and sulfur
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$
or
alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$
or
aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$
whereby at least one of T$^{15}$ and T$^{16}$ is not hydrogen,
or
D represents a group of the formula (XII)

(XII)

wherein
T$^{17}$ is aryl, thioalkoxyl
or
aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$,
Q is oxygen or sulphur,
or
D represents a group of the formula (XIII)

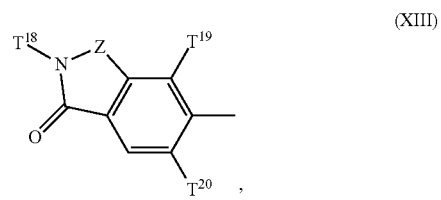

(XIII)

wherein
T$^{18}$ is alkyl, alkenyl, aryl
or
alkyl interrupted by one or more heteroatoms selected from the group consisting of oxygen and sulfur
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N- aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl, and COOR$^{12}$ or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, T$^{19}$ and T$^{20}$ independent from each other is hydrogen, halogen, cyano, nitro or trifluoromethyl, Z is a carbonyl or a sulfonyl rest, or D represents a group of the formula (XIV)

wherein

T$^{21}$ is cyano, nitro or alkoxycarbonyl,

T$^{22}$ is alkyl, hydrogen, halogen, aryl or alkyl interrupted by one or more heteroatoms selected from the group consisting of oxygen and sulfur or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or alkyl interrupted by one or more heteroatoms selected from the group consisting of oxygen or sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or aryl substituted by one or more substituents selected from the group consisting of hydroxy, aryl, cycloalkyl, alkoxy, thioalkoxy, amino, N-monoalkyl-amino, N,N-dialkylamino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or D represents a group of the formula (XV)

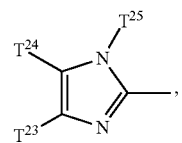

(XV)

wherein

T$^{23}$ and T$^{24}$ independent from each other is cyano, nitro, halogen, aryl or trifluoromethyl, T$^{25}$ is hydrogen, alkyl, alkenyl, aryl or alkyl interrupted by one or more heteroatoms selected from the group consisting of oxygen and sulphur or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-mono-aryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or D represents a group of the formula (XVI)

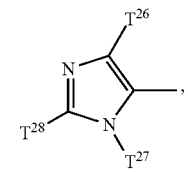

(XVI)

wherein

T$^{26}$ is cyano, nitro, aryl or trifluoromethyl,

T$^{27}$ is hydrogen, aryl, alkyl or alkyl interrupted by one or more heteroatoms selected from the group consisting of oxygen and sulfur or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, T$^{28}$ is hydrogen, alkyl, alkenyl, alkynyl, aryl, alkoxycarbonyl or alkyl interrupted by one or more heteroatoms selected from the group consisting of oxygen and sulfur or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N- monoarylsulfamoyl, arylsulphonyloxy, alkylsulphonyloxy, aryloxysulfonyl, alkoxylsulfonyl and COOR$^{12}$,
or
D represents a group of the formula (XVII)

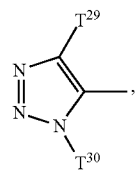

(XVII)

wherein
T$^{29}$ is cyano, nitro, aryl or trifluoromethyl,
T$^{30}$ is hydrogen, alkyl, alkenyl, alkenyl, alkynyl, aryl, arylmethyl, alkoxycarbonyl
or
alkyl interrupted by one or more heteroatoms selected from the group consisting of oxygen and sulfur
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$
or
alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkylmonoarylsulfamoyl, N-monoalkyl-N-monoarylsulfamoyl, arylsulphonyloxy, alkylsulphonyloxy, aryloxysulfonyl, alkoxylsulfonyl and COOR$^{12}$
or
aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$,
or
D represents a group of the formula (XVIII)

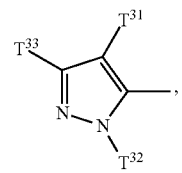

(XVIII)

wherein
T$^{31}$ is cyano, nitro, aryl, trifluoromethyl
or
aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$,
T$^{32}$ is hydrogen, alkyl, alkenyl, alkynyl, aryl, alkoxycarbonyl
or
alkyl interrupted by one or more heteroatoms selected from the group consisting of oxygen and sulphur or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$
or
alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N, N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$
or
aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, arylsulphonyloxy, alkylsulphonyloxy, aryloxysulfonyl, alkoxylsulfonyl and COOR$^{12}$, T$^{33}$ is hydrogen, alkyl
or
alkyl interrupted by one or more heteroatoms selected from the group consisting of oxygen and sulphur
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$
or
alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$
or
aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N- monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or D represents a group of the formula (XIX)

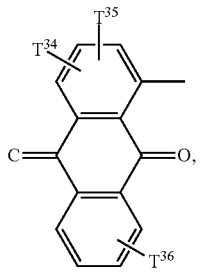

(XIX)

wherein
$T^{34}$, $T^{35}$ and $T^{36}$ independent from each other is hydrogen, halogen, nitro, cyano, hydroxyl, alkoxylcarbonyl, alkyl, acyl or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or D represents a group of the formula (XX)

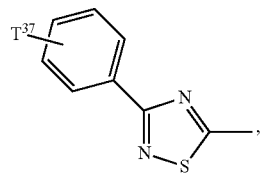

(XX)

wherein
$T^{37}$ is hydrogen, halogen or nitro,
$R^{12}$ is hydrogen, alkyl, alkenyl, cycloalkyl, aryl, heteroaryl, heterocycloalkyl or alkyl interrupted by one or more heteroatoms selected from the group consisting of oxygen and sulfur or alkyl substituted by one or more substituents selected from the group consisting of hydroxy, aryl, cycloalkyl, alkoxy, thioalkoxy, halogen, cyano, amino, thiocyano, nitro, acyl, thioacyl, alkylsulfonyl, aryloyl, trifluoromethyl, heteroaryl, heterocycloalkyl, alkoxythiocarbonyl, acyloxy, aryloyloxy, carbamoyl, sulfamoyl, arylsulphonyloxy, alkylsulphonyloxy, aryloxysulfonyl and alkoxylsulfonyl or alkyl interrupted by one or more heteroatoms selected from the group consisting of oxygen and sulphur and substituted by one or more substituents selected from the group consisting of hydroxy, aryl, cycloalkyl, alkoxy, thioalkoxy, halogen, cyano, amino, thiocyano, nitro, acyl, thioacyl, alkylsulfonyl, aryloyl, trifluoromethyl, heteroaryl, heterocycloalkyl, alkoxythiocarbonyl, acyloxy, aryloyloxy, carbamoyl, sulfamoyl, arylsulphonyloxy, alkylsulphonyloxy, aryloxysulfonyl and alkoxylsulfonyl or aryl substituted by one or more substituents selected from the group consisting of hydroxy, aryl, cycloalkyl, alkoxy, thioalkoxy, amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, sulfamoyl, arylsulphonyloxy, alkylsulphonyloxy, aryloxysulfonyl and alkoxylsulfonyl,
with the proviso that when D represents a group of formula (XV) Y is carbonyl only and no fused-ring formation is allowed among $R^2$ to $R^{14}$.

This invention refers to all tautomeric and geometric isomers of the dyes of formula (I) and mixtures thereof.

Figure 1:
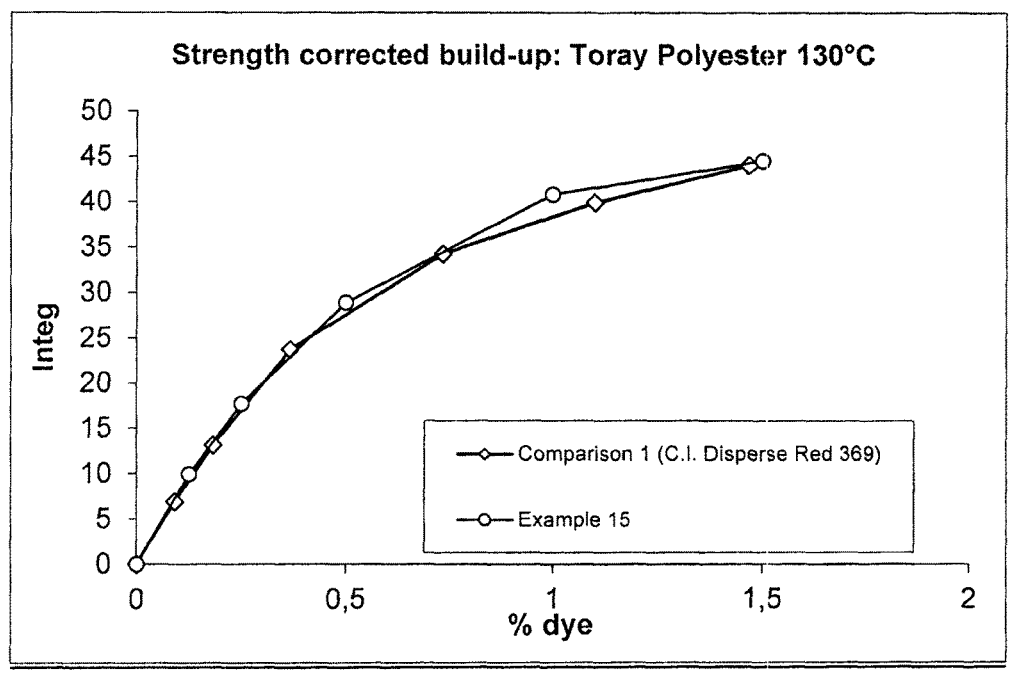
FIG. 1 illustrates the dye according to Example 15 of the present invention which has build-up on Toray polyester at 130° C. which is compared to the commercial product C.I. Disperse Red 369 (Comparison 1).

Alkyl groups appearing in this invention may be straight-chain or branched and are $(C_1-C_{12})$-alkyl groups, preferably $(C_1-C_6)$-alkyl groups, for example methyl, ethyl, propyl, isopropyl, n-butyl, isobutyl, tert-butyl, n-pentyl, isopentyl or n-hexyl.

The same applies to alkoxy groups which accordingly are preferably $(C_1-C_8)$-alkoxy, for example methoxy and ethoxy, to thioalkoxy groups, which are preferably $(C_1-C_8)$-thioalkoxy, for example methylsulfanyl or ethylsulfanyl.

Cycloalkyl groups are preferably $(C_3-C_8)$-cycloalkyl and especially preferably cyclopentyl and cyclohexyl. The term cycloalkyl comprises for the purpose of the present invention substituted cycloalkyl groups and unsaturated cycloalkyl groups as well. A preferred group of this type is cyclopentenyl. Preferred substituents are alkyl, hydroxyalkyl, halogen, hydroxyl, alkoxy, acyl, cyano, nitro, amino, monoalkylamino, dialkylamino, mono(hydroxyalkyl)amino, bis (hydroxyalkyl)amino, monoalkyl-mono(hydroxyalkyl)amino, carbamoyl, sulfamoyl, acylamino, aminosulfonylamino, alkoxycarbonyl and acyloxy.

Alkenyl groups may be straight-chain or branched and are preferably $(C_2-C_6)$-groups for example vinyl and allyl. The term alkenyl comprises for the purpose of the present invention alkynyl groups as well, for example ethynyl and propargyl.

Aryl groups appearing in this invention are preferably phenyl or naphthyl. The terms phenyl and naphthyl comprises unsubstituted as well as substituted phenyl and naphthyl. Preferred substituents are alkyl, cycloalkyl, heterocloalkyl, hydroxyalkyl, halogen, hydroxyl, alkoxy, alkylthio, acyl, nitro, cyano, amino, monoalkylamino, dialkylamino, mono(hydroxyalkyl)amino, bis (hydroxyalkyl)amino, monoalkyl-mono(hydroxyalkyl)amino, carbamoyl, sulfamoyl, acylamino, aminosulfonylamino, alkoxycarbonyl, acyloxy, arylsulphonyloxy, alkylsulphonyloxy, aryloxysulfonyl or alkoxylsulfonyl.

Heteroaryl groups appearing in this invention are preferably pyridine, pyrimidine, pyridazine, pyrazine, pyrrole, imidazole, pyrazole, 1,2,4-thiadiazole, 1,2,4-triazole, tetrazole, thiophene, thiazole, isothiazole, benzothiazole, benzoisothiazole, 1,3,4-thiadiazole, furane, oxazole, benzoxazole or isoxazole. The terms heteroaryl comprises the above groups in unsubstituted as well as in substituted form. Preferred substituents are alkyl, hydroxyalkyl, halogen, hydroxyl, alkoxy, alkylthio, acyl, nitro, cyano, amino, monoalkylamino, dialkylamino, mono(hydroxyalkyl)amino, bis (hydroxyalkyl)amino, monoalkyl-mono(hydroxyalkyl)amino, carbamoyl, sulfamoyl, acylamino, aminosulfonylamino, alkoxycarbonyl, arylsulphonyloxy, alkylsulphonyloxy, aryloxysulfonyl, alkoxylsulfonyl or acyloxy.

Heterocycloalkyl groups are preferably pyrrolidine, piperidine, morpholine, tetrahydrofuran or piperazine. The terms heterocycloalkyl comprises the above groups in unsubstituted as well as in substituted form. Preferred substituents are alkyl, hydroxyalkyl, halogen, hydroxyl, alkoxy, alkylthio, acyl, nitro, cyano, amino, monoalkylamino, dialkylamino, mono(hydroxyalkyl)amino, bis(hydroxyalkyl)amino, monoalkyl-mono(hydroxyalkyl)amino, carbamoyl, sulfamoyl, acylamino, aminocarbonylamino, aminosulfonylamino, alkoxycarbonyl, arylsulphonyloxy, alkylsulphonyloxy, aryloxysulfonyl, alkoxylsulfonyl or acyloxy.

Halogen is preferably chlorine, bromine or fluorine.

A preferred group of dyes is the group wherein Y is carbonyl.

Preferred are dyes as described above having formula (I-a)

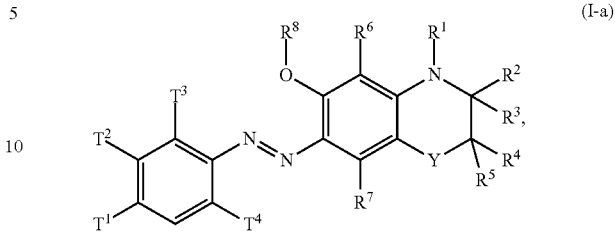

(I-a)

wherein
each of $T^1$ to $T^4$ independent from each other is hydrogen, $(C_1-C_6)$-alkyl, $(C_3-C_6)$-cycloalkyl, substituted $(C_1-C_6)$-alkyl, $(C_3-C_4)$-alkenyl, $(C_3-C_4)$-alkynyl, aryl, O-interrupted $(C_1-C_6)$-alkyl, S-interrupted $(C_1-C_6)$-alkyl, $(C_1-C_8)$-alkoxyl, $(C_1-C_6)$-cycloalkyl, halogen, cyano, nitro, arylsulfonyl, arylsulfonyloxy, $(C_1-C_6)$-alkylsulfonyl, $(C_1-C_6)$-alkoxylsulfonyl, N—$(C_1-C_6)$-alkylsulfamoyl, N,N-bis$(C_1-C_6)$alkylsulfamoyl, N—$(C_1-C_6)$-alkyl carbamoyl, N-bis$(C_1-C_6)$alkylcarbamoyl, $(C_1-C_6)$-alkylacyl, arylacyl, $(C_1-C_6)$-alkoxylcarbonyl, aryloxycarbonyl, thiocyano, hydroxyl, aryloxy, arylmethoxyl, aryloyloxy, arylsulfonyloxy, {[($C_1$-$C_6$)-alkoxylcarbonyl]methoxyl}carbonyl, [(aryloxycarbonyl)methoxy]carbonyl, {[($C_1$-$C_6$)-alkylacyl]-methoxy}carbonyl or [(arylacyl)-methoxy]carbonyl, $R^1$ is $(C_1-C_6)$-alkyl, $(C_1-C_6)$-acyloxy substituted $(C_2-C_6)$ alkyl, cyano$(C_1-C_6)$alkyl, arylmethyl, arylacyl $(C_1-C_6)$alkyl, 2-$(C_1-C_6)$alkoxyl-2-oxoethyl, O-interrupted $(C_2-C_6)$-alkyl, S-interrupted $(C_2-C_6)$-alkyl, $(C_3-C_4)$-alkenyl, $(C_3-C_4)$-alkynyl, 3-$(C_1-C_6)$alkoxyl-3-oxopropyl, 3-[O-interrupted $(C_2-C_6)$-alkoxyl]-3-oxopropyl, 2-$(C_1-C_6)$alkoxyl-2-oxoethyl, 2-[O-interrupted $(C_2-C_6)$-alkoxyl]-2-oxoethyl, 2-{[($C_1$-$C_6$)-alkylacyl]-methoxy}-2-oxoethyl, 3-{[($C_1$-$C_6$)-alkylacyl]-methoxy}-3-oxopropyl, 2-[(arylacyl)-methoxy]-2-oxoethyl, 3-[(arylacyl)-methoxy]-3-oxopropyl, 3-{[($C_1$-$C_6$)-alkoxyl-carbonyl]-methoxy}-3-oxopropyl, 3-(arylmethoxy)-3-oxopropyl, 3-[(arylacyl)-methoxy]-3-oxopropyl, 2-(cyanomethoxy)-2-oxoethyl, 3-(cyanomethoxy)-3-oxopropyl, 2-{[($C_1$-$C_6$)-alkoxylcarbonyl]methoxy}-2-oxoethyl, 1-[($C_1$-$C_6$)-alkyl]-3-[($C_1$-$C_6$)-alkoxyl]-3-oxopropyl, 1-[($C_1$-$C_6$)-alkyl]-3-[O-interrupted $(C_1-C_6)$-alkoxyl]-3-oxopropyl, 1-[($C_1$-$C_6$)-alkyl]-3-(arylmethoxyl)-3-oxopropyl, 1-[($C_1$-$C_6$)-alkyl]-3-{[($C_1$-$C_6$)-alkylacyl]methoxy}-3-oxopropyl or 1-[($C_1$-$C_6$)-alkyl]-3-{[($C_1$-$C_6$)-alkoxylcarbonyl]-methoxy}-3-oxopropyl, $R^2$ to $R^7$ independent from each other is hydrogen, $(C_1-C_6)$ alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl
and
Y is carbonyl.

In particularly preferred dyes of the formula (I-a):
$T^1$, $T^3$ and $T^4$ independent from each other is hydrogen, nitro, cyano, bromine, chlorine, benzoxyl, phenoxy, methoxy, ethoxy, methyl, trifluromethyl, ethyl, benzoyl, acetyl, hydroxyl, methoxycarbonyl, ethoxycarbonyl, methylsulfonyl, cyanomethylsulfonyl, acetonylsulfonyl, (2-ethoxy-2-oxoethyl)sulfonyl, (2-methoxy-2-oxoethyl)sulfonyl, phenylsulfonyloxy, phenoxymethylsulfonyl, ethoxylsulfonyl, phenoxysulfonyl cyanomethoxylcarbonyl, (2-ethoxy-2-oxoethyl)carbonyl, (2-methoxy-2-oxoethyl)carbonyl, acetonylcarbonyl or phenacylcarbonyl, $T^2$ is hydrogen, chlorine, bromine, methoxy, ethoxyl, phenoxy, benzoxy, nitro, methyl or ethyl, $R^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-($C_1$-$C_6$)alkoxyl-3-oxopropyl, 3-[O-interrupted ($C_2$-$C_6$)-alkoxyl]-3-oxopropyl, 2-($C_2$-$C_6$)alkyl-2-oxoethyl, 2-[O-interrupted ($C_2$-$C_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[($C_1$-$C_6$)alkylacyl]-methoxyl}-3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)-alkoxycabonyl]methoxy}-2-oxoethyl or 2-{[($C_1$-$C_6$)alkylacyl]-methoxyl}2-oxoethyl, $R^2$ to $R^7$ independent from each other is hydrogen, bromine, chlorine, ethyl or methyl, $R^8$ is hydrogen, methyl, ethyl, propyl, isopropyl, 2-ethoxy-2-oxoethyl or 2-methoxy-2-oxoethyl and Y is carbonyl.

Examples of preferred dyes of the formula (I-a) are the compounds illustrated in Table 1 and mixtures thereof.

TABLE 1

(I-a)

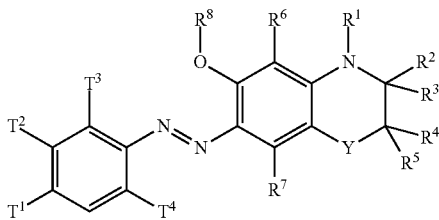

$R^3$ to $R^7$ is hydrogen, Y is carbonyl

| Expl. | $T^1$ | $T^2$ | $T^3$ | $T^4$ | $R^2$ | $R^8$ | $R^1$ |
|---|---|---|---|---|---|---|---|
| 1 | $NO_2$ | H | CN | Br | H | H | —$(CH_2)_2CO_2H$ |
| 2 | $NO_2$ | H | CN | Br | H | H | —$(CH_2)_2CO_2CH_3$ |
| 3 | $NO_2$ | H | CN | Br | H | H | —$(CH_2)_2CO_2CH_2CH_3$ |
| 4 | $NO_2$ | H | CN | Br | H | H | —$(CH_2)_2CO_2(CH_2)_2CH_3$ |
| 5 | $NO_2$ | H | CN | Br | H | H | —$(CH_2)_2CO_2CH(CH_3)_2$ |
| 6 | $NO_2$ | H | CN | Br | H | H | —$(CH_2)_2CO_2(CH_2)_3CH_3$ |
| 7 | $NO_2$ | H | CN | Br | H | H | —$(CH_2)_2CO_2CH(CH_3)CH_2CH_3$ |
| 8 | $NO_2$ | H | CN | Br | H | H | —$(CH_2)_2CO_2CH_2C_6H_5$ |
| 9 | $NO_2$ | H | CN | Br | H | H | —$(CH_2)_2CO_2(CH_2)_2OCH_3$ |
| 10 | $NO_2$ | H | CN | Br | H | H | —$(CH_2)_2CO_2(CH_2)_2OCH_2CH_3$ |
| 11 | $NO_2$ | H | CN | Br | H | H | —$(CH_2)_2CO_2(CH_2)_3OCH_3$ |
| 12 | $NO_2$ | H | CN | Br | H | H | —$(CH_2)_2CO_2(CH_2)_3OCH_2CH_3$ |
| 13 | $NO_2$ | H | CN | H | H | H | —$(CH_2)_2CO_2H$ |
| 14 | $NO_2$ | H | CN | H | H | H | —$(CH_2)_2CO_2CH_3$ |
| 15 | $NO_2$ | H | CN | H | H | H | —$(CH_2)_2CO_2CH_2CH_3$ |
| 16 | $NO_2$ | H | CN | H | H | H | —$(CH_2)_2CO_2(CH_2)_2CH_3$ |
| 17 | $NO_2$ | H | CN | H | H | H | —$(CH_2)_2CO_2CH(CH_3)_2$ |
| 18 | $NO_2$ | H | CN | H | H | H | —$(CH_2)_2CO_2(CH_2)_3CH_3$ |
| 19 | $NO_2$ | H | CN | H | H | H | —$(CH_2)_2CO_2CH(CH_3)CH_2CH_3$ |
| 20 | $NO_2$ | H | CN | H | H | H | —$(CH_2)_2CO_2CH_2C_6H_5$ |
| 21 | $NO_2$ | H | CN | H | H | H | —$(CH_2)_2CO_2(CH_2)_2OCH_3$ |
| 22 | $NO_2$ | H | CN | H | H | H | —$(CH_2)_2CO_2(CH_2)_2OCH_2CH_3$ |
| 23 | $NO_2$ | H | CN | H | H | H | —$(CH_2)_2CO_2(CH_2)_3OCH_3$ |
| 24 | $NO_2$ | H | CN | H | H | H | —$(CH_2)_2CO_2(CH_2)_3OCH_2CH_3$ |
| 25 | $NO_2$ | H | $NO_2$ | H | H | H | —$(CH_2)_2CO_2H$ |
| 26 | $NO_2$ | H | $NO_2$ | H | H | H | —$(CH_2)_2CO_2CH_3$ |
| 27 | $NO_2$ | H | $NO_2$ | H | H | H | —$(CH_2)_2CO_2CH_2CH_3$ |
| 28 | $NO_2$ | H | $NO_2$ | H | H | H | —$(CH_2)_2CO_2(CH_2)_2CH_3$ |
| 29 | $NO_2$ | H | $NO_2$ | H | H | H | —$(CH_2)_2CO_2CH(CH_3)_2$ |
| 30 | $NO_2$ | H | $NO_2$ | H | H | H | —$(CH_2)_2CO_2(CH_2)_3CH_3$ |
| 31 | $NO_2$ | H | $NO_2$ | H | H | H | —$(CH_2)_2CO_2CH(CH_3)CH_2CH_3$ |
| 32 | $NO_2$ | H | $NO_2$ | H | H | H | —$(CH_2)_2CO_2CH_2C_6H_5$ |
| 33 | $NO_2$ | H | $NO_2$ | H | H | H | —$(CH_2)_2CO_2(CH_2)_2OCH_3$ |
| 34 | $NO_2$ | H | $NO_2$ | H | H | H | —$(CH_2)_2CO_2(CH_2)_2OCH_2CH_3$ |
| 35 | $NO_2$ | H | $NO_2$ | H | H | H | —$(CH_2)_2CO_2(CH_2)_3OCH_3$ |
| 36 | $NO_2$ | H | $NO_2$ | H | H | H | —$(CH_2)_2CO_2(CH_2)_3OCH_2CH_3$ |
| 37 | $NO_2$ | H | $NO_2$ | Br | H | H | —$(CH_2)_2CO_2H$ |
| 38 | $NO_2$ | H | $NO_2$ | Br | H | H | —$(CH_2)_2CO_2CH_3$ |
| 39 | $NO_2$ | H | $NO_2$ | Br | H | H | —$(CH_2)_2CO_2CH_2CH_3$ |
| 40 | $NO_2$ | H | $NO_2$ | Br | H | H | —$(CH_2)_2CO_2(CH_2)_2CH_3$ |
| 41 | $NO_2$ | H | $NO_2$ | Br | H | H | —$(CH_2)_2CO_2CH(CH_3)_2$ |
| 42 | $NO_2$ | H | $NO_2$ | Br | H | H | —$(CH_2)_2CO_2(CH_2)_3CH_3$ |
| 43 | $NO_2$ | H | $NO_2$ | Br | H | H | —$(CH_2)_2CO_2CH(CH_3)CH_2CH_3$ |
| 44 | $NO_2$ | H | $NO_2$ | Br | H | H | —$(CH_2)_2CO_2CH_2C_6H_5$ |
| 45 | $NO_2$ | H | $NO_2$ | Br | H | H | —$(CH_2)_2CO_2(CH_2)_2OCH_3$ |

TABLE 1-continued

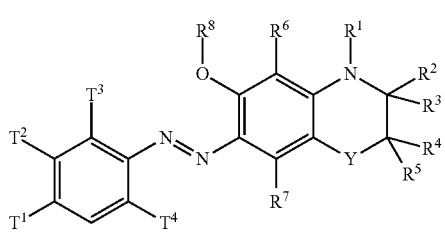

R³ to R⁷ is hydrogen, Y is carbonyl

| Expl. | T¹ | T² | T³ | T⁴ | R² | R⁸ | R¹ |
|---|---|---|---|---|---|---|---|
| 46 | NO₂ | H | NO₂ | Br | H | H | —(CH₂)₂CO₂(CH₂)₂OCH₂CH₃ |
| 47 | NO₂ | H | NO₂ | Br | H | H | —(CH₂)₂CO₂(CH₂)₃OCH₃ |
| 48 | NO₂ | H | NO₂ | Br | H | H | —(CH₂)₂CO₂(CH₂)₃OCH₂CH₃ |
| 49 | NO₂ | H | NO₂ | Cl | H | H | —(CH₂)₂CO₂H |
| 50 | NO₂ | H | NO₂ | Cl | H | H | —(CH₂)₂CO₂CH₃ |
| 51 | NO₂ | H | NO₂ | Cl | H | H | —(CH₂)₂CO₂CH₂CH₃ |
| 52 | NO₂ | H | NO₂ | Cl | H | H | —(CH₂)₂CO₂(CH₂)₂CH₃ |
| 53 | NO₂ | H | NO₂ | Cl | H | H | —(CH₂)₂CO₂CH(CH₃)₂ |
| 54 | NO₂ | H | NO₂ | Cl | H | H | —(CH₂)₂CO₂(CH₂)₃CH₃ |
| 55 | NO₂ | H | NO₂ | Cl | H | H | —(CH₂)₂CO₂CH(CH₃)CH₂CH₃ |
| 56 | NO₂ | H | NO₂ | Cl | H | H | —(CH₂)₂CO₂CH₂C₆H₅ |
| 57 | NO₂ | H | NO₂ | Cl | H | H | —(CH₂)₂CO₂(CH₂)₂OCH₃ |
| 58 | NO₂ | H | NO₂ | Cl | H | H | —(CH₂)₂CO₂(CH₂)₂OCH₂CH₃ |
| 59 | NO₂ | H | NO₂ | Cl | H | H | —(CH₂)₂CO₂(CH₂)₃OCH₃ |
| 60 | NO₂ | H | NO₂ | Cl | H | H | —(CH₂)₂CO₂(CH₂)₃OCH₂CH₃ |
| 61 | NO₂ | H | NO₂ | CN | H | H | —(CH₂)₂CO₂H |
| 62 | NO₂ | H | NO₂ | CN | H | H | —(CH₂)₂CO₂CH₃ |
| 63 | NO₂ | H | NO₂ | CN | H | H | —(CH₂)₂CO₂CH₂CH₃ |
| 64 | NO₂ | H | NO₂ | CN | H | H | —(CH₂)₂CO₂(CH₂)₂CH₃ |
| 65 | NO₂ | H | NO₂ | CN | H | H | —(CH₂)₂CO₂CH(CH₃)₂ |
| 66 | NO₂ | H | NO₂ | CN | H | H | —(CH₂)₂CO₂(CH₂)₃CH₃ |
| 67 | NO₂ | H | NO₂ | CN | H | H | —(CH₂)₂CO₂CH(CH₃)CH₂CH₃ |
| 68 | NO₂ | H | NO₂ | CN | H | H | —(CH₂)₂CO₂CH₂C₆H₅ |
| 69 | NO₂ | H | NO₂ | CN | H | H | —(CH₂)₂CO₂(CH₂)₂OCH₃ |
| 70 | NO₂ | H | NO₂ | CN | H | H | —(CH₂)₂CO₂(CH₂)₂OCH₂CH₃ |
| 71 | NO₂ | H | NO₂ | CN | H | H | —(CH₂)₂CO₂(CH₂)₃OCH₃ |
| 72 | NO₂ | H | NO₂ | CN | H | H | —(CH₂)₂CO₂(CH₂)₃OCH₂CH₃ |
| 73 | NO₂ | H | CN | CN | H | H | —(CH₂)₂CO₂H |
| 74 | NO₂ | H | CN | CN | H | H | —(CH₂)₂CO₂CH₃ |
| 75 | NO₂ | H | CN | CN | H | H | —(CH₂)₂CO₂CH₂CH₃ |
| 76 | NO₂ | H | CN | CN | H | H | —(CH₂)₂CO₂(CH₂)₂CH₃ |
| 77 | NO₂ | H | CN | CN | H | H | —(CH₂)₂CO₂CH(CH₃)₂ |
| 78 | NO₂ | H | CN | CN | H | H | —(CH₂)₂CO₂(CH₂)₃CH₃ |
| 79 | NO₂ | H | CN | CN | H | H | —(CH₂)₂CO₂CH(CH₃)CH₂CH₃ |
| 80 | NO₂ | H | CN | CN | H | H | —(CH₂)₂CO₂CH₂C₆H₅ |
| 81 | NO₂ | H | CN | CN | H | H | —(CH₂)₂CO₂(CH₂)₂OCH₃ |
| 82 | NO₂ | H | CN | CN | H | H | —(CH₂)₂CO₂(CH₂)₂OCH₂CH₃ |
| 83 | NO₂ | H | CN | CN | H | H | —(CH₂)₂CO₂(CH₂)₃OCH₃ |
| 84 | NO₂ | H | CN | CN | H | H | —(CH₂)₂CO₂(CH₂)₃OCH₂CH₃ |
| 85 | Br | H | CN | CN | H | H | —(CH₂)₂CO₂H |
| 86 | Br | H | CN | CN | H | H | —(CH₂)₂CO₂CH₃ |
| 87 | Br | H | CN | CN | H | H | —(CH₂)₂CO₂CH₂CH₃ |
| 88 | Br | H | CN | CN | H | H | —(CH₂)₂CO₂(CH₂)₂CH₃ |
| 89 | Br | H | CN | CN | H | H | —(CH₂)₂CO₂CH(CH₃)₂ |
| 90 | Br | H | CN | CN | H | H | —(CH₂)₂CO₂(CH₂)₃CH₃ |
| 91 | Br | H | CN | CN | H | H | —(CH₂)₂CO₂CH(CH₃)CH₂CH₃ |
| 92 | Br | H | CN | CN | H | H | —(CH₂)₂CO₂CH₂C₆H₅ |
| 93 | Br | H | CN | CN | H | H | —(CH₂)₂CO₂(CH₂)₂OCH₃ |
| 94 | Br | H | CN | CN | H | H | —(CH₂)₂CO₂(CH₂)₂OCH₂CH₃ |
| 95 | Br | H | CN | CN | H | H | —(CH₂)₂CO₂(CH₂)₃OCH₃ |
| 96 | Br | H | CN | CN | H | H | —(CH₂)₂CO₂(CH₂)₃OCH₂CH₃ |
| 97 | —CO₂CH₃ | H | NO₂ | NO₂ | H | H | —(CH₂)₂CO₂H |
| 98 | —CO₂CH₃ | H | NO₂ | NO₂ | H | H | —(CH₂)₂CO₂CH₃ |
| 99 | —CO₂CH₃ | H | NO₂ | NO₂ | H | H | —(CH₂)₂CO₂CH₂CH₃ |
| 100 | —CO₂CH₃ | H | NO₂ | NO₂ | H | H | —(CH₂)₂CO₂(CH₂)₂CH₃ |
| 101 | —CO₂CH₃ | H | NO₂ | NO₂ | H | H | —(CH₂)₂CO₂CH(CH₃)₂ |
| 102 | —CO₂CH₃ | H | NO₂ | NO₂ | H | H | —(CH₂)₂CO₂(CH₂)₃CH₃ |
| 103 | —CO₂CH₃ | H | NO₂ | NO₂ | H | H | —(CH₂)₂CO₂CH(CH₃)CH₂CH₃ |
| 104 | —CO₂CH₃ | H | NO₂ | NO₂ | H | H | —(CH₂)₂CO₂CH₂C₆H₅ |

TABLE 1-continued

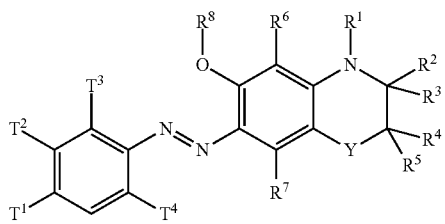

(I-a)

R³ to R⁷ is hydrogen, Y is carbonyl

| Expl. | T¹ | T² | T³ | T⁴ | R² | R⁸ | R¹ |
|---|---|---|---|---|---|---|---|
| 105 | —CO₂CH₃ | H | NO₂ | NO₂ | H | H | —(CH₂)₂CO₂(CH₂)₂OCH₃ |
| 106 | —CO₂CH₃ | H | NO₂ | NO₂ | H | H | —(CH₂)₂CO₂(CH₂)₂OCH₂CH₃ |
| 107 | —CO₂CH₃ | H | NO₂ | NO₂ | H | H | —(CH₂)₂CO₂(CH₂)₃OCH₃ |
| 108 | —CO₂CH₃ | H | NO₂ | NO₂ | H | H | —(CH₂)₂CO₂(CH₂)₃OCH₂CH₃ |
| 109 | —CO₂CH₂CH₃ | H | NO₂ | H | H | H | —(CH₂)₂CO₂H |
| 110 | —CO₂CH₂CH₃ | H | NO₂ | H | H | H | —(CH₂)₂CO₂CH₃ |
| 111 | —CO₂CH₂CH₃ | H | NO₂ | H | H | H | —(CH₂)₂CO₂CH₂CH₃ |
| 112 | —CO₂CH₂CH₃ | H | NO₂ | H | H | H | —(CH₂)₂CO₂(CH₂)₂CH₃ |
| 113 | —CO₂CH₂CH₃ | H | NO₂ | H | H | H | —(CH₂)₂CO₂CH(CH₃)₂ |
| 114 | —CO₂CH₂CH₃ | H | NO₂ | H | H | H | —(CH₂)₂CO₂(CH₂)₃CH₃ |
| 115 | —CO₂CH₂CH₃ | H | NO₂ | H | H | H | —(CH₂)₂CO₂CH(CH₃)CH₂CH₃ |
| 116 | —CO₂CH₂CH₃ | H | NO₂ | H | H | H | —(CH₂)₂CO₂CH₂C₆H₅ |
| 117 | —CO₂CH₂CH₃ | H | NO₂ | H | H | H | —(CH₂)₂CO₂(CH₂)₂OCH₃ |
| 118 | —CO₂CH₂CH₃ | H | NO₂ | H | H | H | —(CH₂)₂CO₂(CH₂)₂OCH₂CH₃ |
| 119 | —CO₂CH₂CH₃ | H | NO₂ | H | H | H | —(CH₂)₂CO₂(CH₂)₃OCH₃ |
| 120 | —CO₂CH₂CH₃ | H | NO₂ | H | H | H | —(CH₂)₂CO₂(CH₂)₃OCH₂CH₃ |
| 121 | —CO₂CH₃ | H | NO₂ | H | H | H | —(CH₂)₂CO₂H |
| 122 | —CO₂CH₃ | H | NO₂ | H | H | H | —(CH₂)₂CO₂CH₃ |
| 123 | —CO₂CH₃ | H | NO₂ | H | H | H | —(CH₂)₂CO₂CH₂CH₃ |
| 124 | —CO₂CH₃ | H | NO₂ | H | H | H | —(CH₂)₂CO₂(CH₂)₂CH₃ |
| 125 | —CO₂CH₃ | H | NO₂ | H | H | H | —(CH₂)₂CO₂CH(CH₃)₂ |
| 126 | —CO₂CH₃ | H | NO₂ | H | H | H | —(CH₂)₂CO₂(CH₂)₃CH₃ |
| 127 | —CO₂CH₃ | H | NO₂ | H | H | H | —(CH₂)₂CO₂CH(CH₃)CH₂CH₃ |
| 128 | —CO₂CH₃ | H | NO₂ | H | H | H | —(CH₂)₂CO₂CH₂C₆H₅ |
| 129 | —CO₂CH₃ | H | NO₂ | H | H | H | —(CH₂)₂CO₂(CH₂)₂OCH₃ |
| 130 | —CO₂CH₃ | H | NO₂ | H | H | H | —(CH₂)₂CO₂(CH₂)₂OCH₂CH₃ |
| 131 | —CO₂CH₃ | H | NO₂ | H | H | H | —(CH₂)₂CO₂(CH₂)₃OCH₃ |
| 132 | —CO₂CH₃ | H | NO₂ | H | H | H | —(CH₂)₂CO₂(CH₂)₃OCH₂CH₃ |
| 133 | C₆H₅CO— | H | NO₂ | H | H | H | —(CH₂)₂CO₂H |
| 134 | C₆H₅CO— | H | NO₂ | H | H | H | —(CH₂)₂CO₂CH₃ |
| 135 | C₆H₅CO— | H | NO₂ | H | H | H | —(CH₂)₂CO₂CH₂CH₃ |
| 136 | C₆H₅CO— | H | NO₂ | H | H | H | —(CH₂)₂CO₂(CH₂)₂CH₃ |
| 137 | C₆H₅CO— | H | NO₂ | H | H | H | —(CH₂)₂CO₂CH(CH₃)₂ |
| 138 | C₆H₅CO— | H | NO₂ | H | H | H | —(CH₂)₂CO₂(CH₂)₃CH₃ |
| 139 | C₆H₅CO— | H | NO₂ | H | H | H | —(CH₂)₂CO₂CH(CH₃)CH₂CH₃ |
| 140 | C₆H₅CO— | H | NO₂ | H | H | H | —(CH₂)₂CO₂CH₂C₆H₅ |
| 141 | C₆H₅CO— | H | NO₂ | H | H | H | —(CH₂)₂CO₂(CH₂)₂OCH₃ |
| 142 | C₆H₅CO— | H | NO₂ | H | H | H | —(CH₂)₂CO₂(CH₂)₂OCH₂CH₃ |
| 143 | C₆H₅CO— | H | NO₂ | H | H | H | —(CH₂)₂CO₂(CH₂)₃OCH₃ |
| 144 | C₆H₅CO— | H | NO₂ | H | H | H | —(CH₂)₂CO₂(CH₂)₃OCH₂CH₃ |
| 145 | NO₂ | H | C₆H₅CO— | H | H | H | —(CH₂)₂CO₂H |
| 146 | NO₂ | H | C₆H₅CO— | H | H | H | —(CH₂)₂CO₂CH₃ |
| 147 | NO₂ | H | C₆H₅CO— | H | H | H | —(CH₂)₂CO₂CH₂CH₃ |
| 148 | NO₂ | H | C₆H₅CO— | H | H | H | —(CH₂)₂CO₂(CH₂)₂CH₃ |
| 149 | NO₂ | H | C₆H₅CO— | H | H | H | —(CH₂)₂CO₂CH(CH₃)₂ |
| 150 | NO₂ | H | C₆H₅CO— | H | H | H | —(CH₂)₂CO₂(CH₂)₃CH₃ |
| 151 | NO₂ | H | C₆H₅CO— | H | H | H | —(CH₂)₂CO₂CH(CH₃)CH₂CH₃ |
| 152 | NO₂ | H | C₆H₅CO— | H | H | H | —(CH₂)₂CO₂CH₂C₆H₅ |
| 153 | NO₂ | H | C₆H₅CO— | H | H | H | —(CH₂)₂CO₂(CH₂)₂OCH₃ |
| 154 | NO₂ | H | C₆H₅CO— | H | H | H | —(CH₂)₂CO₂(CH₂)₂OCH₂CH₃ |
| 155 | NO₂ | H | C₆H₅CO— | H | H | H | —(CH₂)₂CO₂(CH₂)₃OCH₃ |
| 156 | NO₂ | H | C₆H₅CO— | H | H | H | —(CH₂)₂CO₂(CH₂)₃OCH₂CH₃ |
| 157 | NO₂ | H | CN | Cl | H | H | —(CH₂)₂CO₂H |
| 158 | NO₂ | H | CN | Cl | H | H | —(CH₂)₂CO₂CH₃ |
| 159 | NO₂ | H | CN | Cl | H | H | —(CH₂)₂CO₂CH₂CH₃ |
| 160 | NO₂ | H | CN | Cl | H | H | —(CH₂)₂CO₂(CH₂)₂CH₃ |
| 161 | NO₂ | H | CN | Cl | H | H | —(CH₂)₂CO₂CH(CH₃)₂ |
| 162 | NO₂ | H | CN | Cl | H | H | —(CH₂)₂CO₂(CH₂)₃CH₃ |
| 163 | NO₂ | H | CN | Cl | H | H | —(CH₂)₂CO₂CH(CH₃)CH₂CH₃ |

TABLE 1-continued (I-a)

$R^3$ to $R^7$ is hydrogen, Y is carbonyl

| Expl. | T$^1$ | T$^2$ | T$^3$ | T$^4$ | R$^2$ | R$^8$ | R$^1$ |
|---|---|---|---|---|---|---|---|
| 164 | NO$_2$ | H | CN | Cl | H | H | —(CH$_2$)$_2$CO$_2$CH$_2$C$_6$H$_5$ |
| 165 | NO$_2$ | H | CN | Cl | H | H | —(CH$_2$)$_2$CO$_2$(CH$_2$)$_2$OCH$_3$ |
| 166 | NO$_2$ | H | CN | Cl | H | H | —(CH$_2$)$_2$CO$_2$(CH$_2$)$_2$OCH$_2$CH$_3$ |
| 167 | NO$_2$ | H | CN | Cl | H | H | —(CH$_2$)$_2$CO$_2$(CH$_2$)$_3$OCH$_3$ |
| 168 | NO$_2$ | H | CN | Cl | H | H | —(CH$_2$)$_2$CO$_2$(CH$_2$)$_3$OCH$_2$CH$_3$ |
| 169 | NO$_2$ | H | Cl | Cl | H | H | —(CH$_2$)$_2$CO$_2$H |
| 170 | NO$_2$ | H | Cl | Cl | H | H | —(CH$_2$)$_2$CO$_2$CH$_3$ |
| 171 | NO$_2$ | H | Cl | Cl | H | H | —(CH$_2$)$_2$CO$_2$CH$_2$CH$_3$ |
| 172 | NO$_2$ | H | Cl | Cl | H | H | —(CH$_2$)$_2$CO$_2$(CH$_2$)$_2$CH$_3$ |
| 173 | NO$_2$ | H | Cl | Cl | H | H | —(CH$_2$)$_2$CO$_2$CH(CH$_3$)$_2$ |
| 174 | NO$_2$ | H | Cl | Cl | H | H | —(CH$_2$)$_2$CO$_2$(CH$_2$)$_3$CH$_3$ |
| 175 | NO$_2$ | H | Cl | Cl | H | H | —(CH$_2$)$_2$CO$_2$CH(CH$_3$)CH$_2$CH$_3$ |
| 176 | NO$_2$ | H | Cl | Cl | H | H | —(CH$_2$)$_2$CO$_2$CH$_2$C$_6$H$_5$ |
| 177 | NO$_2$ | H | Cl | Cl | H | H | —(CH$_2$)$_2$CO$_2$(CH$_2$)$_2$OCH$_3$ |
| 178 | NO$_2$ | H | Cl | Cl | H | H | —(CH$_2$)$_2$CO$_2$(CH$_2$)$_2$OCH$_2$CH$_3$ |
| 179 | NO$_2$ | H | Cl | Cl | H | H | —(CH$_2$)$_2$CO$_2$(CH$_2$)$_3$OCH$_3$ |
| 180 | NO$_2$ | H | Cl | Cl | H | H | —(CH$_2$)$_2$CO$_2$(CH$_2$)$_3$OCH$_2$CH$_3$ |
| 181 | NO$_2$ | H | Cl | Br | H | H | —(CH$_2$)$_2$CO$_2$H |
| 182 | NO$_2$ | H | Cl | Br | H | H | —(CH$_2$)$_2$CO$_2$CH$_3$ |
| 183 | NO$_2$ | H | Cl | Br | H | H | —(CH$_2$)$_2$CO$_2$CH$_2$CH$_3$ |
| 184 | NO$_2$ | H | Cl | Br | H | H | —(CH$_2$)$_2$CO$_2$(CH$_2$)$_2$CH$_3$ |
| 185 | NO$_2$ | H | Cl | Br | H | H | —(CH$_2$)$_2$CO$_2$CH(CH$_3$)$_2$ |
| 186 | NO$_2$ | H | Cl | Br | H | H | —(CH$_2$)$_2$CO$_2$(CH$_2$)$_3$CH$_3$ |
| 187 | NO$_2$ | H | Cl | Br | H | H | —(CH$_2$)$_2$CO$_2$CH(CH$_3$)CH$_2$CH$_3$ |
| 188 | NO$_2$ | H | Cl | Br | H | H | —(CH$_2$)$_2$CO$_2$CH$_2$C$_6$H$_5$ |
| 189 | NO$_2$ | H | Cl | Br | H | H | —(CH$_2$)$_2$CO$_2$(CH$_2$)$_2$OCH$_3$ |
| 190 | NO$_2$ | H | Cl | Br | H | H | —(CH$_2$)$_2$CO$_2$(CH$_2$)$_2$OCH$_2$CH$_3$ |
| 191 | NO$_2$ | H | Cl | Br | H | H | —(CH$_2$)$_2$CO$_2$(CH$_2$)$_3$OCH$_3$ |
| 192 | NO$_2$ | H | Cl | Br | H | H | —(CH$_2$)$_2$CO$_2$(CH$_2$)$_3$OCH$_2$CH$_3$ |
| 193 | NO$_2$ | H | Br | Br | H | H | —(CH$_2$)$_2$CO$_2$H |
| 194 | NO$_2$ | H | Br | Br | H | H | —(CH$_2$)$_2$CO$_2$CH$_3$ |
| 195 | NO$_2$ | H | Br | Br | H | H | —(CH$_2$)$_2$CO$_2$CH$_2$CH$_3$ |
| 196 | NO$_2$ | H | Br | Br | H | H | —(CH$_2$)$_2$CO$_2$(CH$_2$)$_2$CH$_3$ |
| 197 | NO$_2$ | H | Br | Br | H | H | —(CH$_2$)$_2$CO$_2$CH(CH$_3$)$_2$ |
| 198 | NO$_2$ | H | Br | Br | H | H | —(CH$_2$)$_2$CO$_2$(CH$_2$)$_3$CH$_3$ |
| 199 | NO$_2$ | H | Br | Br | H | H | —(CH$_2$)$_2$CO$_2$CH(CH$_3$)CH$_2$CH$_3$ |
| 200 | NO$_2$ | H | Br | Br | H | H | —(CH$_2$)$_2$CO$_2$CH$_2$C$_6$H$_5$ |
| 201 | NO$_2$ | H | Br | Br | H | H | —(CH$_2$)$_2$CO$_2$(CH$_2$)$_2$OCH$_3$ |
| 202 | NO$_2$ | H | Br | Br | H | H | —(CH$_2$)$_2$CO$_2$(CH$_2$)$_2$OCH$_2$CH$_3$ |
| 203 | NO$_2$ | H | Br | Br | H | H | —(CH$_2$)$_2$CO$_2$(CH$_2$)$_3$OCH$_3$ |
| 204 | NO$_2$ | H | Br | Br | H | H | —(CH$_2$)$_2$CO$_2$(CH$_2$)$_3$OCH$_2$CH$_3$ |
| 205 | —CO$_2$CH$_2$CH$_3$ | CH$_3$ | CN | CN | H | H | —(CH$_2$)$_2$CO$_2$H |
| 206 | —CO$_2$CH$_2$CH$_3$ | CH$_3$ | CN | CN | H | H | —(CH$_2$)$_2$CO$_2$CH$_3$ |
| 207 | —CO$_2$CH$_2$CH$_3$ | CH$_3$ | CN | CN | H | H | —(CH$_2$)$_2$CO$_2$CH$_2$CH$_3$ |
| 208 | —CO$_2$CH$_2$CH$_3$ | CH$_3$ | CN | CN | H | H | —(CH$_2$)$_2$CO$_2$(CH$_2$)$_2$CH$_3$ |
| 209 | —CO$_2$CH$_2$CH$_3$ | CH$_3$ | CN | CN | H | H | —(CH$_2$)$_2$CO$_2$CH(CH$_3$)$_2$ |
| 210 | —CO$_2$CH$_2$CH$_3$ | CH$_3$ | CN | CN | H | H | —(CH$_2$)$_2$CO$_2$(CH$_2$)$_3$CH$_3$ |
| 211 | —CO$_2$CH$_2$CH$_3$ | CH$_3$ | CN | CN | H | H | —(CH$_2$)$_2$CO$_2$CH(CH$_3$)CH$_2$CH$_3$ |
| 212 | —CO$_2$CH$_2$CH$_3$ | CH$_3$ | CN | CN | H | H | —(CH$_2$)$_2$CO$_2$CH$_2$C$_6$H$_5$ |
| 213 | —CO$_2$CH$_2$CH$_3$ | CH$_3$ | CN | CN | H | H | —(CH$_2$)$_2$CO$_2$(CH$_2$)$_2$OCH$_3$ |
| 214 | —CO$_2$CH$_2$CH$_3$ | CH$_3$ | CN | CN | H | H | —(CH$_2$)$_2$CO$_2$(CH$_2$)$_2$OCH$_2$CH$_3$ |
| 215 | —CO$_2$CH$_2$CH$_3$ | CH$_3$ | CN | CN | H | H | —(CH$_2$)$_2$CO$_2$(CH$_2$)$_3$OCH$_3$ |
| 216 | —CO$_2$CH$_2$CH$_3$ | CH$_3$ | CN | CN | H | H | —(CH$_2$)$_2$CO$_2$(CH$_2$)$_3$OCH$_2$CH$_3$ |
| 217 | NO$_2$ | H | H | OCH$_3$ | H | H | —(CH$_2$)$_2$CO$_2$H |
| 218 | NO$_2$ | H | H | OCH$_3$ | H | H | —(CH$_2$)$_2$CO$_2$CH$_3$ |
| 219 | NO$_2$ | H | H | OCH$_3$ | H | H | —(CH$_2$)$_2$CO$_2$CH$_2$CH$_3$ |
| 220 | NO$_2$ | H | H | —OCH$_3$ | H | H | —(CH$_2$)$_2$CO$_2$(CH$_2$)$_2$CH$_3$ |
| 221 | NO$_2$ | H | H | —OCH$_3$ | H | H | —(CH$_2$)$_2$CO$_2$CH(CH$_3$)$_2$ |
| 222 | NO$_2$ | H | H | —OCH$_3$ | H | H | —(CH$_2$)$_2$CO$_2$(CH$_2$)$_3$CH$_3$ |

TABLE 1-continued (I-a)

$R^3$ to $R^7$ is hydrogen, Y is carbonyl

| Expl. | $T^1$ | $T^2$ | $T^3$ | $T^4$ | $R^2$ | $R^8$ | $R^1$ |
|---|---|---|---|---|---|---|---|
| 223 | NO$_2$ | H | H | —OCH$_3$ | H | H | —(CH$_2$)$_2$CO$_2$CH(CH$_3$)CH$_2$CH$_3$ |
| 224 | NO$_2$ | H | H | —OCH$_3$ | H | H | —(CH$_2$)$_2$CO$_2$CH$_2$C$_6$H$_5$ |
| 225 | NO$_2$ | H | H | —OCH$_3$ | H | H | —(CH$_2$)$_2$CO$_2$(CH$_2$)$_2$OCH$_3$ |
| 226 | NO$_2$ | H | H | —OCH$_3$ | H | H | —(CH$_2$)$_2$CO$_2$(CH$_2$)$_2$OCH$_2$CH$_3$ |
| 227 | NO$_2$ | H | H | —OCH$_3$ | H | H | —(CH$_2$)$_2$CO$_2$(CH$_2$)$_3$OCH$_3$ |
| 228 | NO$_2$ | H | H | —OCH$_3$ | H | H | —(CH$_2$)$_2$CO$_2$(CH$_2$)$_3$OCH$_2$CH$_3$ |
| 229 | NO$_2$ | H | H | —OCH$_3$ | H | H | —(CH$_2$)$_2$CO$_2$H |
| 230 | NO$_2$ | H | H | —OCH$_3$ | H | H | —(CH$_2$)$_2$CO$_2$CH$_3$ |
| 231 | NO$_2$ | H | H | —OCH$_3$ | H | H | —(CH$_2$)$_2$CO$_2$CH$_2$CH$_3$ |
| 232 | NO$_2$ | H | H | —OCH$_3$ | H | H | —(CH$_2$)$_2$CO$_2$(CH$_2$)$_2$CH$_3$ |
| 233 | NO$_2$ | H | H | —OCH$_3$ | H | H | —(CH$_2$)$_2$CO$_2$CH(CH$_3$)$_2$ |
| 234 | NO$_2$ | H | H | —OCH$_3$ | H | H | —(CH$_2$)$_2$CO$_2$(CH$_2$)$_3$CH$_3$ |
| 235 | NO$_2$ | H | H | —OCH$_3$ | H | H | —(CH$_2$)$_2$CO$_2$CH(CH$_3$)CH$_2$CH$_3$ |
| 236 | NO$_2$ | H | H | —OCH$_3$ | H | H | —(CH$_2$)$_2$CO$_2$CH$_2$C$_6$H$_5$ |
| 237 | NO$_2$ | H | H | —OCH$_3$ | H | H | —(CH$_2$)$_2$CO$_2$(CH$_2$)$_2$OCH$_3$ |
| 238 | NO$_2$ | H | H | —OCH$_3$ | H | H | —(CH$_2$)$_2$CO$_2$(CH$_2$)$_2$OCH$_2$CH$_3$ |
| 239 | NO$_2$ | H | H | —OCH$_3$ | H | H | —(CH$_2$)$_2$CO$_2$(CH$_2$)$_3$OCH$_3$ |
| 240 | NO$_2$ | H | H | —OCH$_3$ | H | H | —(CH$_2$)$_2$CO$_2$(CH$_2$)$_3$OCH$_2$CH$_3$ |
| 241 | CF$_3$ | H | H | NO$_2$ | H | H | —(CH$_2$)$_2$CO$_2$H |
| 242 | CF$_3$ | H | H | NO$_2$ | H | H | —(CH$_2$)$_2$CO$_2$CH$_3$ |
| 243 | CF$_3$ | H | H | NO$_2$ | H | H | —(CH$_2$)$_2$CO$_2$CH$_2$CH$_3$ |
| 244 | CF$_3$ | H | H | NO$_2$ | H | H | —(CH$_2$)$_2$CO$_2$(CH$_2$)$_2$CH$_3$ |
| 245 | CF$_3$ | H | H | NO$_2$ | H | H | —(CH$_2$)$_2$CO$_2$CH(CH$_3$)$_2$ |
| 246 | CF$_3$ | H | H | NO$_2$ | H | H | —(CH$_2$)$_2$CO$_2$(CH$_2$)$_3$CH$_3$ |
| 247 | CF$_3$ | H | H | NO$_2$ | H | H | —(CH$_2$)$_2$CO$_2$CH(CH$_3$)CH$_2$CH$_3$ |
| 248 | CF$_3$ | H | H | NO$_2$ | H | H | —(CH$_2$)$_2$CO$_2$CH$_2$C$_6$H$_5$ |
| 249 | CF$_3$ | H | H | NO$_2$ | H | H | —(CH$_2$)$_2$CO$_2$(CH$_2$)$_2$OCH$_3$ |
| 250 | CF$_3$ | H | H | NO$_2$ | H | H | —(CH$_2$)$_2$CO$_2$(CH$_2$)$_2$OCH$_2$CH$_3$ |
| 251 | CF$_3$ | H | H | NO$_2$ | H | H | —(CH$_2$)$_2$CO$_2$(CH$_2$)$_3$OCH$_3$ |
| 252 | CF$_3$ | H | H | NO$_2$ | H | H | —(CH$_2$)$_2$CO$_2$(CH$_2$)$_3$OCH$_2$CH$_3$ |
| 253 | CF$_3$ | H | H | Cl | H | H | —(CH$_2$)$_2$CO$_2$H |
| 254 | CF$_3$ | H | H | Cl | H | H | —(CH$_2$)$_2$CO$_2$CH$_3$ |
| 255 | CF$_3$ | H | H | Cl | H | H | —(CH$_2$)$_2$CO$_2$CH$_2$CH$_3$ |
| 256 | CF$_3$ | H | H | Cl | H | H | —(CH$_2$)$_2$CO$_2$(CH$_2$)$_2$CH$_3$ |
| 257 | CF$_3$ | H | H | Cl | H | H | —(CH$_2$)$_2$CO$_2$CH(CH$_3$)$_2$ |
| 258 | CF$_3$ | H | H | Cl | H | H | —(CH$_2$)$_2$CO$_2$(CH$_2$)$_3$CH$_3$ |
| 259 | CF$_3$ | H | H | Cl | H | H | —(CH$_2$)$_2$CO$_2$CH(CH$_3$)CH$_2$CH$_3$ |
| 260 | CF$_3$ | H | H | Cl | H | H | —(CH$_2$)$_2$CO$_2$CH$_2$C$_6$H$_5$ |
| 261 | CF$_3$ | H | H | Cl | H | H | —(CH$_2$)$_2$CO$_2$(CH$_2$)$_2$OCH$_3$ |
| 262 | CF$_3$ | H | H | Cl | H | H | —(CH$_2$)$_2$CO$_2$(CH$_2$)$_2$OCH$_2$CH$_3$ |
| 263 | CF$_3$ | H | H | Cl | H | H | —(CH$_2$)$_2$CO$_2$(CH$_2$)$_3$OCH$_3$ |
| 264 | CF$_3$ | H | H | Cl | H | H | —(CH$_2$)$_2$CO$_2$(CH$_2$)$_3$OCH$_2$CH$_3$ |
| 265 | H | H | NO$_2$ | NO$_2$ | H | H | —(CH$_2$)$_2$CO$_2$H |
| 266 | H | H | NO$_2$ | NO$_2$ | H | H | —(CH$_2$)$_2$CO$_2$CH$_3$ |
| 267 | H | H | NO$_2$ | NO$_2$ | H | H | —(CH$_2$)$_2$CO$_2$CH$_2$CH$_3$ |
| 268 | H | H | NO$_2$ | NO$_2$ | H | H | —(CH$_2$)$_2$CO$_2$(CH$_2$)$_2$CH$_3$ |
| 269 | H | H | NO$_2$ | NO$_2$ | H | H | —(CH$_2$)$_2$CO$_2$CH(CH$_3$)$_2$ |
| 270 | H | H | NO$_2$ | NO$_2$ | H | H | —(CH$_2$)$_2$CO$_2$(CH$_2$)$_3$CH$_3$ |
| 271 | H | H | NO$_2$ | NO$_2$ | H | H | —(CH$_2$)$_2$CO$_2$CH(CH$_3$)CH$_2$CH$_3$ |
| 272 | H | H | NO$_2$ | NO$_2$ | H | H | —(CH$_2$)$_2$CO$_2$CH$_2$C$_6$H$_5$ |
| 273 | H | H | NO$_2$ | NO$_2$ | H | H | —(CH$_2$)$_2$CO$_2$(CH$_2$)$_2$OCH$_3$ |
| 274 | H | H | NO$_2$ | NO$_2$ | H | H | —(CH$_2$)$_2$CO$_2$(CH$_2$)$_2$OCH$_2$CH$_3$ |
| 275 | H | H | NO$_2$ | NO$_2$ | H | H | —(CH$_2$)$_2$CO$_2$(CH$_2$)$_3$OCH$_3$ |
| 276 | H | H | NO$_2$ | NO$_2$ | H | H | —(CH$_2$)$_2$CO$_2$(CH$_2$)$_3$OCH$_2$CH$_3$ |
| 277 | CH$_3$ | H | CN | CN | H | H | —(CH$_2$)$_2$CO$_2$H |
| 278 | CH$_3$ | H | CN | CN | H | H | —(CH$_2$)$_2$CO$_2$CH$_3$ |
| 279 | CH$_3$ | H | CN | CN | H | H | —(CH$_2$)$_2$CO$_2$CH$_2$CH$_3$ |
| 280 | CH$_3$ | H | CN | CN | H | H | —(CH$_2$)$_2$CO$_2$(CH$_2$)$_2$CH$_3$ |
| 281 | CH$_3$ | H | CN | CN | H | H | —(CH$_2$)$_2$CO$_2$CH(CH$_3$)$_2$ |

TABLE 1-continued (I-a)

R³ to R⁷ is hydrogen, Y is carbonyl

| Expl. | T¹ | T² | T³ | T⁴ | R² | R⁸ | R¹ |
|---|---|---|---|---|---|---|---|
| 282 | CH₃ | H | CN | CN | H | H | —(CH₂)₂CO₂(CH₂)₃CH₃ |
| 283 | CH₃ | H | CN | CN | H | H | —(CH₂)₂CO₂CH(CH₃)CH₂CH₃ |
| 284 | CH₃ | H | CN | CN | H | H | —(CH₂)₂CO₂CH₂C₆H₅ |
| 285 | CH₃ | H | CN | CN | H | H | —(CH₂)₂CO₂(CH₂)₂OCH₃ |
| 286 | CH₃ | H | CN | CN | H | H | —(CH₂)₂CO₂(CH₂)₂OCH₂CH₃ |
| 287 | CH₃ | H | CN | CN | H | H | —(CH₂)₂CO₂(CH₂)₃OCH₃ |
| 288 | CH₃ | H | CN | CN | H | H | —(CH₂)₂CO₂(CH₂)₃OCH₂CH₃ |
| 289 | —SO₂CH₃ | H | Br | Br | H | H | —(CH₂)₂CO₂H |
| 290 | —SO₂CH₃ | H | Br | Br | H | H | —(CH₂)₂CO₂CH₃ |
| 291 | —SO₂CH₃ | H | Br | Br | H | H | —(CH₂)₂CO₂CH₂CH₃ |
| 292 | —SO₂CH₃ | H | Br | Br | H | H | —(CH₂)₂CO₂(CH₂)₂CH₃ |
| 293 | —SO₂CH₃ | H | Br | Br | H | H | —(CH₂)₂CO₂CH(CH₃)₂ |
| 294 | —SO₂CH₃ | H | Br | Br | H | H | —(CH₂)₂CO₂(CH₂)₃CH₃ |
| 295 | —SO₂CH₃ | H | Br | Br | H | H | —(CH₂)₂CO₂CH(CH₃)CH₂CH₃ |
| 296 | —SO₂CH₃ | H | Br | Br | H | H | —(CH₂)₂CO₂CH₂C₆H₅ |
| 297 | —SO₂CH₃ | H | Br | Br | H | H | —(CH₂)₂CO₂(CH₂)₂OCH₃ |
| 298 | —SO₂CH₃ | H | Br | Br | H | H | —(CH₂)₂CO₂(CH₂)₂OCH₂CH₃ |
| 299 | —SO₂CH₃ | H | Br | Br | H | H | —(CH₂)₂CO₂(CH₂)₃OCH₃ |
| 300 | —SO₂CH₃ | H | Br | Br | H | H | —(CH₂)₂CO₂(CH₂)₃OCH₂CH₃ |
| 301 | —SO₂CH₃ | H | NO₂ | H | H | H | —(CH₂)₂CO₂H |
| 302 | —SO₂CH₃ | H | NO₂ | Br | H | H | —(CH₂)₂CO₂CH₃ |
| 303 | —SO₂CH₃ | H | NO₂ | Br | H | H | —(CH₂)₂CO₂CH₂CH₃ |
| 304 | —SO₂CH₃ | H | NO₂ | Br | H | H | —(CH₂)₂CO₂(CH₂)₂CH₃ |
| 305 | —SO₂CH₃ | H | NO₂ | Br | H | H | —(CH₂)₂CO₂CH(CH₃)₂ |
| 306 | —SO₂CH₃ | H | NO₂ | Br | H | H | —(CH₂)₂CO₂(CH₂)₃CH₃ |
| 307 | —SO₂CH₃ | H | NO₂ | Br | H | H | —(CH₂)₂CO₂CH(CH₃)CH₂CH₃ |
| 308 | —SO₂CH₃ | H | NO₂ | Br | H | H | —(CH₂)₂CO₂CH₂C₆H₅ |
| 309 | —SO₂CH₃ | H | NO₂ | Br | H | H | —(CH₂)₂CO₂(CH₂)₂OCH₃ |
| 310 | —SO₂CH₃ | H | NO₂ | Br | H | H | —(CH₂)₂CO₂(CH₂)₂OCH₂CH₃ |
| 311 | —SO₂CH₃ | H | NO₂ | Br | H | H | —(CH₂)₂CO₂(CH₂)₃OCH₃ |
| 312 | —SO₂CH₃ | H | NO₂ | Br | H | H | —(CH₂)₂CO₂(CH₂)₃OCH₂CH₃ |
| 313 | NO₂ | H | —SO₂CH₃ | H | H | H | —(CH₂)₂CO₂H |
| 314 | NO₂ | H | —SO₂CH₃ | H | H | H | —(CH₂)₂CO₂CH₃ |
| 315 | NO₂ | H | —SO₂CH₃ | H | H | H | —(CH₂)₂CO₂CH₂CH₃ |
| 316 | NO₂ | H | —SO₂CH₃ | H | H | H | —(CH₂)₂CO₂(CH₂)₂CH₃ |
| 317 | NO₂ | H | —SO₂CH₃ | H | H | H | —(CH₂)₂CO₂CH(CH₃)₂ |
| 318 | NO₂ | H | —SO₂CH₃ | H | H | H | —(CH₂)₂CO₂(CH₂)₃CH₃ |
| 319 | NO₂ | H | —SO₂CH₃ | H | H | H | —(CH₂)₂CO₂CH(CH₃)CH₂CH₃ |
| 320 | NO₂ | H | —SO₂CH₃ | H | H | H | —(CH₂)₂CO₂CH₂C₆H₅ |
| 321 | NO₂ | H | —SO₂CH₃ | H | H | H | —(CH₂)₂CO₂(CH₂)₂OCH₃ |
| 322 | NO₂ | H | —SO₂CH₃ | H | H | H | —(CH₂)₂CO₂(CH₂)₂OCH₂CH₃ |
| 323 | NO₂ | H | —SO₂CH₃ | H | H | H | —(CH₂)₂CO₂(CH₂)₃OCH₃ |
| 324 | NO₂ | H | —SO₂CH₃ | H | H | H | —(CH₂)₂CO₂(CH₂)₃OCH₂CH₃ |
| 325 | —CO₂CH₃ | H | H | H | H | CH₃ | —(CH₂)₂CO₂CH₂CH₃ |
| 326 | —CO₂CH₃ | H | H | H | H | H | —(CH₂)₂CO₂CH₂CH₃ |
| 327 | Cl | H | H | NO₂ | H | H | —(CH₂)₂CO₂CH₂CH₃ |
| 328 | Cl | H | H | —OCH₃ | H | H | —(CH₂)₂CO₂CH₂CH₃ |
| 329 | CN | Cl | H | H | H | H | —(CH₂)₂CO₂CH₂CH₃ |
| 330 | CH₃ | H | H | NO₂ | H | H | —(CH₂)₂CO₂CH₂CH₃ |
| 331 | H | NO₂ | H | H | H | H | —(CH₂)₂CO₂CH₂CH₃ |
| 332 | NO₂ | H | Cl | H | H | H | —(CH₂)₂CO₂CH₂CH₃ |
| 333 | NO₂ | Cl | Cl | H | CH₃ | H | —CH(CH₃)CO₂CH₂CH₃ |
| 334 | NO₂ | H | H | H | H | H | —(CH₂)₂CO₂CH₂CN |
| 335 | NO₂ | H | H | H | H | H | —(CH₂)₂CO₂CH₂CO₂CH₃ |
| 336 | NO₂ | H | H | H | H | H | —(CH₂)₂CO₂CH₂CO₂C₂H₅ |
| 337 | NO₂ | H | H | H | H | H | —(CH₂)₂CO₂CH₂COCH₃ |
| 338 | NO₂ | H | H | H | H | H | —(CH₂)₂CO₂CH₂COC₂H₅ |
| 339 | NO₂ | H | H | H | H | H | —(CH₂)₂CO₂CH₂COC₆H₅ |
| 340 | NO₂ | H | Br | CF₃ | H | CH₃ | —(CH₂)₂CO₂CH₂CH₃ |
| 341 | NO₂ | H | CN | H | H | CH₃ | —(CH₂)₂CO₂CH₂CH₃ |

TABLE 1-continued (I-a)

$R^3$ to $R^7$ is hydrogen, Y is carbonyl

| Expl. | $T^1$ | $T^2$ | $T^3$ | $T^4$ | $R^2$ | $R^8$ | $R^1$ |
|---|---|---|---|---|---|---|---|
| 342 | $NO_2$ | H | $NO_2$ | H | H | $CH_3$ | —$(CH_2)_2CO_2CH_3$ |
| 343 | $NO_2$ | H | CN | CN | H | $CH_3$ | —$(CH_2)_2CH_2CH_2CH_3$ |
| 344 | $NO_2$ | H | CN | $NO_2$ | H | $CH_3$ | —$(CH_2)_2CH_2CH_2CH_3$ |
| 345 | $NO_2$ | H | Br | Cl | H | $CH_3$ | —$(CH_2)_2CH_2CH_2CH_3$ |

Preferred are dyes as described above having formula (I-b)

(I-b)

wherein
$T^5$ to $T^7$ independent from each other is hydrogen, $(C_1-C_6)$ alkyl, $(C_3-C_8)$cycloalkyl, O-interrupted $(C_1-C_6)$-alkyl, S-interrupted $(C_1-C_6)$-alkyl, aryl, $(C_1-C_6)$alkoxyl, halogen, cyano, nitro, $(C_1-C_6)$-alkylacyl, arylacyl, $(C_1-C_6)$-alkoxycarbonyl, aryloxycarbonyl, N—$(C_1-C_6)$-alkyl carbamoyl, or N,N-bis$(C_1-C_6)$-alkyl carbamoyl,
whereby at least one of $T^5$, $T^6$ and $T^7$ is not hydrogen,
$R^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$ alkylacyl]-methoxyl}-2-oxoethyl,
$R^2$ to $R^7$ independent from each other is hydrogen, $(C_1-C_6)$ alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen,
$R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl
and
Y is carbonyl.

Examples of preferred dyes of the formula (I-b) are the compounds illustrated in Table 2, and mixtures thereof.

TABLE 2

| Example | Structure |
|---|---|
| 346 | 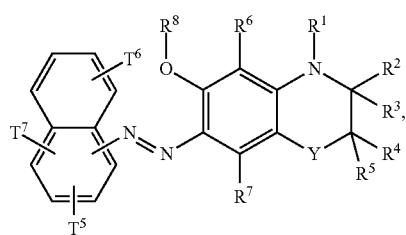 |

TABLE 2-continued

| Example | Structure |
|---|---|
| 347 | 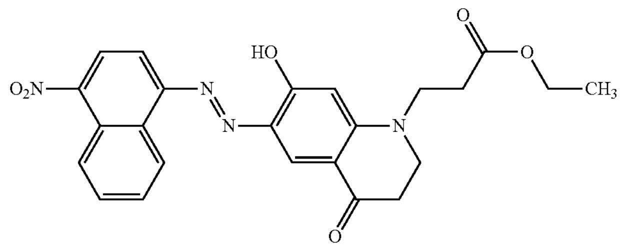 [SMILES: CCOC(=O)CCN1CCC(=O)c2cc(/N=N/c3ccc([N+](=O)[O-])c4ccccc34)c(O)cc21] |
| 348 | 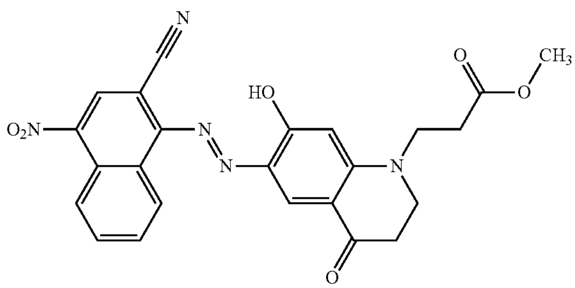 [SMILES: COC(=O)CCN1CCC(=O)c2cc(/N=N/c3c(C#N)cc([N+](=O)[O-])c4ccccc34)c(O)cc21] |
| 349 | 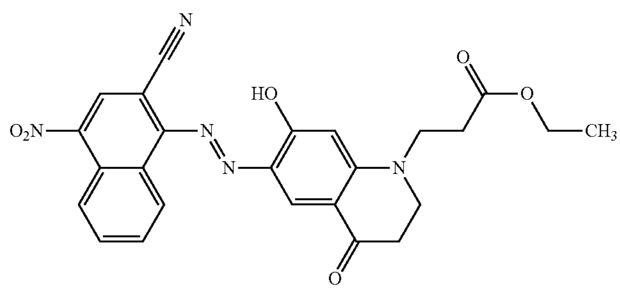 [SMILES: CCOC(=O)CCN1CCC(=O)c2cc(/N=N/c3c(C#N)cc([N+](=O)[O-])c4ccccc34)c(O)cc21] |

Another preferred aspect of the present invention are dyes as described above having formula (I-c)

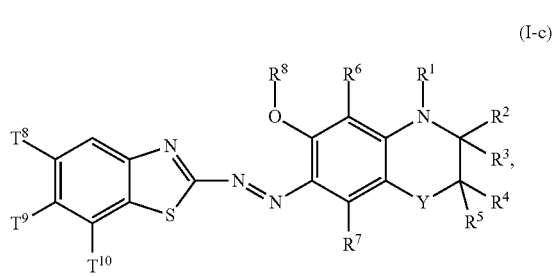

(I-c)

wherein $T^8$ and $T^{10}$ independent from each other is hydrogen, chlorine or bromine, $T^9$ is hydrogen, $(C_1-C_6)$-alkylsulfonyl, thiocyano, $(C_1-C_6)$ alkoxy, chlorine or nitro, $R^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$ alkylacyl]-methoxyl}-2-oxoethyl, $R^2$ to $R^7$ independent from each other is hydrogen, $(C_1-C_6)$ alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

Examples of preferred dyes of the formula (I-c) are the compounds illustrated in Table 3 and mixtures thereof.

TABLE 3

(I-c)

R³ to R⁷ is hydrogen, Y is carbonyl

| Example | $T^8$ | $T^9$ | $T^{10}$ | $R^2$ | $R^1$ | $R^8$ |
|---|---|---|---|---|---|---|
| 350 | H | $NO_2$ | H | H | —$(CH_2)_2CO_2H$ | H |
| 351 | H | $NO_2$ | H | H | —$(CH_2)_2CO_2CH_3$ | H |
| 352 | H | $NO_2$ | H | H | —$(CH_2)_2CO_2CH_2CH_3$ | H |
| 353 | H | $NO_2$ | H | H | —$(CH_2)_2CO_2(CH_2)_2CH_3$ | H |
| 354 | H | $NO_2$ | H | H | —$(CH_2)_2CO_2CH(CH_3)_2$ | H |
| 355 | H | $NO_2$ | H | H | —$(CH_2)_2CO_2(CH_2)_3CH_3$ | H |
| 356 | H | $NO_2$ | H | H | —$(CH_2)_2CO_2CH(CH_3)CH_2CH_3$ | H |
| 357 | H | $NO_2$ | H | H | —$(CH_2)_2CO_2CH_2C_6H_5$ | H |
| 358 | H | $NO_2$ | H | H | —$(CH_2)_2CO_2(CH_2)_2OCH_3$ | H |
| 359 | H | $NO_2$ | H | H | —$(CH_2)_2CO_2(CH_2)_2OCH_2CH_3$ | H |
| 360 | H | $NO_2$ | H | H | —$(CH_2)_2CO_2(CH_2)_3OCH_3$ | H |
| 361 | H | $NO_2$ | H | H | —$(CH_2)_2CO_2(CH_2)_3OCH_2CH_3$ | H |
| 362 | Cl | Cl | H | H | —$(CH_2)_2CO_2H$ | H |
| 363 | Cl | Cl | H | H | —$(CH_2)_2CO_2CH_3$ | H |
| 364 | Cl | Cl | H | H | —$(CH_2)_2CO_2CH_2CH_3$ | H |
| 365 | Cl | Cl | H | H | —$(CH_2)_2CO_2(CH_2)_2CH_3$ | H |
| 366 | Cl | Cl | H | H | —$(CH_2)_2CO_2CH(CH_3)_2$ | H |
| 367 | Cl | Cl | H | H | —$(CH_2)_2CO_2(CH_2)_3CH_3$ | H |
| 368 | Cl | Cl | H | H | —$(CH_2)_2CO_2CH(CH_3)CH_2CH_3$ | H |
| 369 | Cl | Cl | H | H | —$(CH_2)_2CO_2CH_2C_6H_5$ | H |
| 370 | Cl | Cl | H | H | —$(CH_2)_2CO_2CH_2C_6H_5$ | H |
| 371 | Cl | Cl | H | H | —$(CH_2)_2CO_2(CH_2)_2OCH_2CH_3$ | H |
| 372 | Cl | Cl | H | H | —$(CH_2)_2CO_2(CH_2)_3OCH_3$ | H |
| 373 | Cl | Cl | H | H | —$(CH_2)_2CO_2(CH_2)_3OCH_2CH_3$ | H |
| 374 | H | —$OCH_3$ | H | H | —$(CH_2)_2CO_2H$ | H |
| 375 | H | —$OCH_3$ | H | H | —$(CH_2)_2CO_2CH_3$ | H |
| 376 | H | —$OCH_3$ | H | H | —$(CH_2)_2CO_2CH_2CH_3$ | H |
| 377 | H | —$OCH_3$ | H | H | —$(CH_2)_2CO_2(CH_2)_2CH_3$ | H |
| 378 | H | —$OCH_3$ | H | H | —$(CH_2)_2CO_2CH(CH_3)_2$ | H |
| 379 | H | —$OCH_3$ | H | H | —$(CH_2)_2CO_2(CH_2)_3CH_3$ | H |
| 380 | H | —$OCH_3$ | H | H | —$(CH_2)_2CO_2CH(CH_3)CH_2CH_3$ | H |
| 381 | H | —$OCH_3$ | H | H | —$(CH_2)_2CO_2CH_2C_6H_5$ | H |
| 382 | H | —$OCH_3$ | H | H | —$(CH_2)_2CO_2(CH_2)_2OCH_3$ | H |
| 383 | H | —$OCH_3$ | H | H | —$(CH_2)_2CO_2(CH_2)_2OCH_2CH_3$ | H |
| 384 | H | —$OCH_3$ | H | H | —$(CH_2)_2CO_2(CH_2)_3OCH_3$ | H |
| 385 | H | —$OCH_3$ | H | H | —$(CH_2)_2CO_2(CH_2)_3OCH_2CH_3$ | H |
| 386 | H | H | H | H | —$(CH_2)_2CO_2H$ | H |
| 387 | H | H | H | H | —$(CH_2)_2CO_2CH_3$ | H |
| 388 | H | H | H | H | —$(CH_2)_2CO_2CH_2CH_3$ | H |
| 389 | H | H | H | H | —$(CH_2)_2CO_2(CH_2)_2CH_3$ | H |
| 390 | H | H | H | H | —$(CH_2)_2CO_2CH(CH_3)_2$ | H |
| 391 | H | H | H | H | —$(CH_2)_2CO_2(CH_2)_3CH_3$ | H |
| 392 | H | H | H | H | —$(CH_2)_2CO_2CH(CH_3)CH_2CH_3$ | H |
| 393 | H | H | H | H | —$(CH_2)_2CO_2CH_2C_6H_5$ | H |
| 394 | H | H | H | H | —$(CH_2)_2CO_2(CH_2)_2OCH_3$ | H |
| 395 | H | H | H | H | —$(CH_2)_2CO_2(CH_2)_2OCH_2CH_3$ | H |
| 396 | H | H | H | H | —$(CH_2)_2CO_2(CH_2)_3OCH_3$ | H |
| 397 | H | H | H | H | —$(CH_2)_2CO_2(CH_2)_3OCH_2CH_3$ | H |
| 398 | H | —$SO_2CH_3$ | H | H | —$(CH_2)_2CO_2H$ | H |
| 399 | H | —$SO_2CH_3$ | H | H | —$(CH_2)_2CO_2CH_3$ | H |
| 400 | H | —$SO_2CH_3$ | H | H | —$(CH_2)_2CO_2CH_2CH_3$ | H |
| 401 | H | —$SO_2CH_3$ | H | H | —$(CH_2)_2CO_2(CH_2)_2CH_3$ | H |
| 402 | H | —$SO_2CH_3$ | H | H | —$(CH_2)_2CO_2CH(CH_3)_2$ | H |
| 403 | H | —$SO_2CH_3$ | H | H | —$(CH_2)_2CO_2(CH_2)_3CH_3$ | H |
| 404 | H | —$SO_2CH_3$ | H | H | —$(CH_2)_2CO_2CH(CH_3)CH_2CH_3$ | H |
| 405 | H | —$SO_2CH_3$ | H | H | —$(CH_2)_2CO_2CH_2C_6H_5$ | H |
| 406 | H | —$SO_2CH_3$ | H | H | —$(CH_2)_2CO_2(CH_2)_2OCH_3$ | H |
| 407 | H | —$SO_2CH_3$ | H | H | —$(CH_2)_2CO_2(CH_2)_2OCH_2CH_3$ | H |
| 408 | H | —$SO_2CH_3$ | H | H | —$(CH_2)_2CO_2(CH_2)_3OCH_3$ | H |
| 409 | H | —$SO_2CH_3$ | H | H | —$(CH_2)_2CO_2(CH_2)_3OCH_2CH_3$ | H |
| 410 | H | —$SO_2CH_3$ | H | H | —$(CH_2)_2CO_2(CH_2)_3OCH_2CH_3$ | —$CH_3$ |

Just another preferred embodiment of the present invention are dyes as described above having formula (I-d)

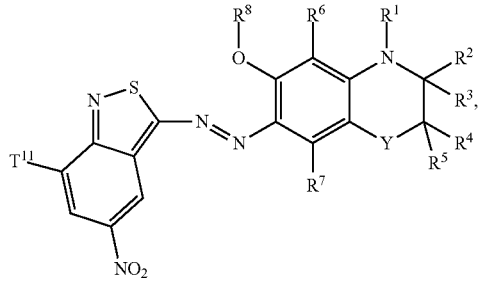

(I-d)

wherein
$T^{11}$ is hydrogen, nitro or bromine,
$R^1$ is methyl, ethyl, propyl, isopropyl, n-butyl, isobutyl, benzyl, 2-methoxyethyl, 2-ethoxyethyl, 2-acetoxyethyl, 2-(propionyl)oxyethyl, 2-(benzoyl)oxyethyl, cyanomethyl, 2-cyanoethyl, 3-cyanopropyl, 3-($C_1$-$C_6$)alkoxyl-3-oxopropyl, 3-[O-interrupted ($C_2$-$C_6$)-alkoxyl]-3-oxopropyl, 2-($C_1$-$C_6$)alkyl-2-oxoethyl, 2-[O-interrupted ($C_2$-$C_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(aryl-methoxy)-3-oxopropyl, 3-{[($C_1$-$C_6$)alkylacyl]-methoxyl}-3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)-alkoxycabonyl]methoxy}-2-oxoethyl or 2-{[($C_1$-$C_6$)alkylacyl]-methoxyl}2-oxoethyl,
$R^2$ to $R^7$ independent from each other is hydrogen, ($C_1$-$C_6$)alkyl, aryl, ($C_1$-$C_8$)alkoxyl, ($C_3$-$C_8$)cycloalkyl, O-interrupted ($C_2$-$C_6$)alkyl, S-interrupted ($C_2$-$C_6$)alkyl or halogen,
$R^8$ is hydrogen, ($C_1$-$C_6$)alkyl, ($C_3$-$C_4$)-alkenyl, ($C_3$-$C_4$)-alkynyl, arylmethyl, 2-($C_1$-$C_6$)alkoxyl-2-oxoethyl, 2-(aryl-methyl)-2-oxoethyl, cyano($C_1$-$C_6$)alkyl, O-interrupted ($C_1$-$C_6$)alkyl or S-interrupted ($C_1$-$C_6$)alkyl
and
Y is carbonyl.

Examples of preferred dyes of the formula (l-d) are the compounds illustrated in Table 4 and mixtures thereof.

TABLE 4

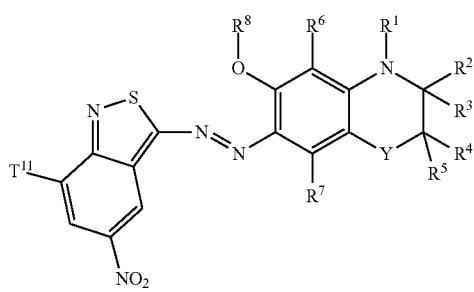

(I-d)

$R^3$ to $R^7$ is hydrogen, Y is carbonyl

| Example | $T^{11}$ | $R^2$ | $R^1$ | $R^8$ |
|---|---|---|---|---|
| 411 | H | H | —($CH_2$)$_2$$CO_2$H | H |
| 412 | H | H | —($CH_2$)$_2$$CO_2$$CH_3$ | H |
| 413 | H | H | —($CH_2$)$_2$$CO_2$$CH_2$$CH_3$ | H |
| 414 | H | H | —($CH_2$)$_2$$CO_2$($CH_2$)$_2$$CH_3$ | H |
| 415 | H | H | —($CH_2$)$_2$$CO_2$$CH(CH_3)_2$ | H |

TABLE 4-continued

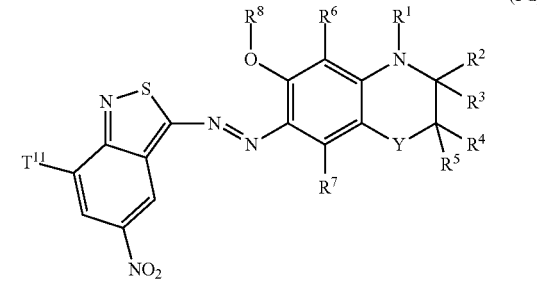

(I-d)

$R^3$ to $R^7$ is hydrogen, Y is carbonyl

| Example | $T^{11}$ | $R^2$ | $R^1$ | $R^8$ |
|---|---|---|---|---|
| 416 | H | H | —($CH_2$)$_2$$CO_2$($CH_2$)$_3$$CH_3$ | H |
| 417 | H | H | —($CH_2$)$_2$$CO_2$$CH(CH_3)CH_2$$CH_3$ | H |
| 418 | H | H | —($CH_2$)$_2$$CO_2$$CH_2$$C_6$$H_5$ | H |
| 419 | H | H | —($CH_2$)$_2$$CO_2$($CH_2$)$_2$$OCH_3$ | H |
| 420 | H | H | —($CH_2$)$_2$$CO_2$($CH_2$)$_2$$OCH_2$$CH_3$ | H |
| 421 | H | H | —($CH_2$)$_2$$CO_2$($CH_2$)$_3$$OCH_3$ | H |
| 422 | H | H | —($CH_2$)$_2$$CO_2$($CH_2$)$_3$$OCH_2$$CH_3$ | H |
| 423 | Br | H | —($CH_2$)$_2$$CO_2$H | H |
| 424 | Br | H | —($CH_2$)$_2$$CO_2$$CH_3$ | H |
| 425 | Br | H | —($CH_2$)$_2$$CO_2$$CH_2$$CH_3$ | H |
| 426 | Br | H | —($CH_2$)$_2$$CO_2$($CH_2$)$_2$$CH_3$ | H |
| 427 | Br | H | —($CH_2$)$_2$$CO_2$$CH(CH_3)_2$ | H |
| 428 | Br | H | —($CH_2$)$_2$$CO_2$($CH_2$)$_3$$CH_3$ | H |
| 429 | Br | H | —($CH_2$)$_2$$CO_2$$CH(CH_3)CH_2$$CH_3$ | H |
| 430 | Br | H | —($CH_2$)$_2$$CO_2$$CH_2$$C_6$$H_5$ | H |
| 431 | Br | H | —($CH_2$)$_2$$CO_2$($CH_2$)$_2$$OCH_3$ | H |
| 432 | Br | H | —($CH_2$)$_2$$CO_2$($CH_2$)$_2$$OCH_2$$CH_3$ | H |
| 433 | Br | H | —($CH_2$)$_2$$CO_2$($CH_2$)$_3$$OCH_3$ | H |
| 434 | Br | H | —($CH_2$)$_2$$CO_2$($CH_2$)$_3$$OCH_2$$CH_3$ | H |
| 435 | Br | —$CH_3$ | —$CH(CH_3)CH_2$$CO_2$($CH_2$)$_3$$OCH_2$$CH_3$ | H |
| 436 | Br | H | —($CH_2$)$_2$$CO_2$($CH_2$)$_3$$OCH_2$$CH_3$ | —$CH_3$ |

Also preferred are dyes as described above having formula (I-e)

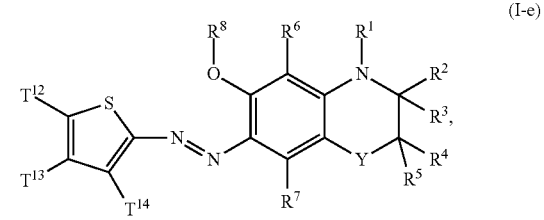

(I-e)

wherein
$T^{12}$ and $T^{14}$ independent from each other, are nitro, cyano, formyl, acetyl or ($C_1$-$C_6$)-alkoxycarbonyl,
$T^{13}$ is hydrogen, aryl, ($C_1$-$C_6$)-alkyl or halogen,
$R^1$ is methyl, ethyl, propyl, isopropyl, n-butyl, isobutyl, benzyl, 2-methoxyethyl, 2-ethoxyethyl, 2-acetoxyethyl, 2-(propionyl)oxyethyl, 2-(benzoyl)oxyethyl, cyanomethyl, 2-cyanoethyl, 3-cyanopropyl, 3-($C_1$-$C_6$)alkoxyl-3-oxopropyl, 3-[O-interrupted ($C_2$-$C_6$)-alkoxyl]-3-oxopropyl, 2-($C_1$-$C_6$)alkyl-2-oxoethyl, 2-[O-interrupted ($C_2$-$C_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(aryl-methoxy)-3-oxopropyl, 3-{[($C_1$-$C_6$)alkylacyl]-methoxyl}-3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)- alkoxycabonyl]methoxy}-2-oxoethyl or 2-{[(C$_1$-C$_6$)alkylacyl]-methoxyl}-2-oxoethyl,
R$^2$ to R$^7$ independent from each other is hydrogen, (C$_1$-C$_6$) alkyl, aryl, (C$_1$-C$_8$)alkoxyl, (C$_3$-C$_8$)cycloalkyl, O-interrupted (C$_2$-C$_6$)alkyl, S-interrupted (C$_2$-C$_6$)alkyl or halogen,
R$^8$ is hydrogen, (C$_1$-C$_6$)alkyl, (C$_3$-C$_4$)-alkenyl, (C$_3$-C$_4$)-alkynyl, arylmethyl, 2-(C$_1$-C$_6$)alkoxyl-2-oxoethyl, 2-(arylmethyl)-2-oxoethyl, cyano(C$_1$-C$_6$)alkyl, O-interrupted (C$_1$-C$_6$)alkyl or S-interrupted (C$_1$-C$_6$)alkyl
and
Y is carbonyl.

Examples of preferred dyes of the formula (I-e) are the compounds illustrated in Table 5 and mixtures thereof.

TABLE 5

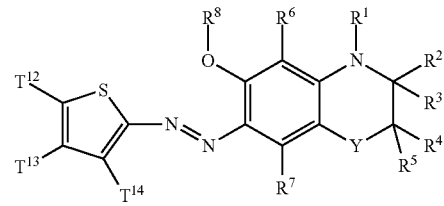

(I-e)

R$^3$ to R$^7$ is hydrogen, Y is carbonyl

| Expl. | T$^{12}$ | T$^{14}$ | T$^{13}$ | R$^2$ | R$^1$ | R$^8$ |
|---|---|---|---|---|---|---|
| 437 | NO$_2$ | NO$_2$ | H | H | —(CH$_2$)$_2$CO$_2$H | H |
| 438 | NO$_2$ | NO$_2$ | H | H | —(CH$_2$)$_2$CO$_2$CH$_3$ | H |
| 439 | NO$_2$ | NO$_2$ | H | H | —(CH$_2$)$_2$CO$_2$CH$_2$CH$_3$ | H |
| 440 | NO$_2$ | NO$_2$ | H | H | —(CH$_2$)$_2$CO$_2$(CH$_2$)$_2$CH$_3$ | H |
| 441 | NO$_2$ | NO$_2$ | H | H | —(CH$_2$)$_2$CO$_2$CH(CH$_3$)$_2$ | H |
| 442 | NO$_2$ | NO$_2$ | H | H | —(CH$_2$)$_2$CO$_2$(CH$_2$)$_3$CH$_3$ | H |
| 443 | NO$_2$ | NO$_2$ | H | H | —(CH$_2$)$_2$CO$_2$CH(CH$_3$)CH$_2$CH$_3$ | H |
| 444 | NO$_2$ | NO$_2$ | H | H | —(CH$_2$)$_2$CO$_2$CH$_2$C$_6$H$_5$ | H |
| 445 | NO$_2$ | NO$_2$ | H | H | —(CH$_2$)$_2$CO$_2$(CH$_2$)$_2$OCH$_3$ | H |
| 446 | NO$_2$ | NO$_2$ | H | H | —(CH$_2$)$_2$CO$_2$(CH$_2$)$_2$OCH$_2$CH$_3$ | H |
| 447 | NO$_2$ | NO$_2$ | H | H | —(CH$_2$)$_2$CO$_2$(CH$_2$)$_3$OCH$_3$ | H |
| 448 | NO$_2$ | NO$_2$ | H | H | —(CH$_2$)$_2$CO$_2$(CH$_2$)$_3$OCH$_2$CH$_3$ | H |
| 449 | CN | CN | H | H | —(CH$_2$)$_2$CO$_2$H | H |
| 450 | CN | CN | H | H | —(CH$_2$)$_2$CO$_2$CH$_3$ | H |
| 451 | CN | CN | CH$_3$ | H | —(CH$_2$)$_2$CO$_2$CH$_2$CH$_3$ | H |
| 452 | CN | CN | CH$_3$ | H | —(CH$_2$)$_2$CO$_2$(CH$_2$)$_2$CH$_3$ | H |
| 453 | CN | CN | CH$_3$ | H | —(CH$_2$)$_2$CO$_2$CH(CH$_3$)$_2$ | H |
| 454 | CN | CN | CH$_3$ | H | —(CH$_2$)$_2$CO$_2$(CH$_2$)$_3$CH$_3$ | H |
| 455 | CN | CN | CH$_3$ | H | —(CH$_2$)$_2$CO$_2$CH(CH$_3$)CH$_2$CH$_3$ | H |
| 456 | CN | CN | CH$_3$ | H | —(CH$_2$)$_2$CO$_2$CH$_2$C$_6$H$_5$ | H |
| 457 | CN | CN | CH$_3$ | H | —(CH$_2$)$_2$CO$_2$(CH$_2$)$_2$OCH$_3$ | H |
| 458 | CN | CN | CH$_3$ | H | —(CH$_2$)$_2$CO$_2$(CH$_2$)$_2$OCH$_2$CH$_3$ | H |
| 459 | CN | CN | CH$_3$ | H | —(CH$_2$)$_2$CO$_2$(CH$_2$)$_3$OCH$_3$ | H |
| 460 | CN | CN | CH$_3$ | H | —(CH$_2$)$_2$CO$_2$(CH$_2$)$_3$OCH$_2$CH$_3$ | H |
| 461 | —CHO | CN | Cl | H | —(CH$_2$)$_2$CO$_2$H | H |
| 462 | —CHO | CN | Cl | H | —(CH$_2$)$_2$CO$_2$CH$_3$ | H |
| 463 | —CHO | CN | Cl | H | —(CH$_2$)$_2$CO$_2$CH$_2$CH$_3$ | H |
| 464 | —CHO | CN | Cl | H | —(CH$_2$)$_2$CO$_2$(CH$_2$)$_2$CH$_3$ | H |
| 465 | —CHO | CN | Cl | H | —(CH$_2$)$_2$CO$_2$CH(CH$_3$)$_2$ | H |
| 466 | —CHO | CN | Cl | H | —(CH$_2$)$_2$CO$_2$(CH$_2$)$_3$CH$_3$ | H |
| 467 | —CHO | CN | Cl | H | —(CH$_2$)$_2$CO$_2$CH(CH$_3$)CH$_2$CH$_3$ | H |
| 468 | —CHO | CN | Cl | H | —(CH$_2$)$_2$CO$_2$CH$_2$C$_6$H$_5$ | H |
| 469 | —CHO | CN | Cl | H | —(CH$_2$)$_2$CO$_2$(CH$_2$)$_2$OCH$_3$ | H |
| 470 | —CHO | CN | Cl | H | —(CH$_2$)$_2$CO$_2$(CH$_2$)$_2$OCH$_2$CH$_3$ | H |
| 471 | —CHO | CN | Cl | H | —(CH$_2$)$_2$CO$_2$(CH$_2$)$_3$OCH$_3$ | H |
| 472 | —CHO | CN | Cl | H | —(CH$_2$)$_2$CO$_2$(CH$_2$)$_3$OCH$_2$CH$_3$ | H |
| 473 | —CO$_2$CH$_2$CH$_3$ | CN | CH$_3$ | H | —(CH$_2$)$_2$CO$_2$H | H |
| 474 | —CO$_2$CH$_2$CH$_3$ | CN | CH$_3$ | H | —(CH$_2$)$_2$CO$_2$CH$_3$ | H |
| 475 | —CO$_2$CH$_2$CH$_3$ | CN | CH$_3$ | H | —(CH$_2$)$_2$CO$_2$CH$_2$CH$_3$ | H |
| 476 | —CO$_2$CH$_2$CH$_3$ | CN | CH$_3$ | H | —(CH$_2$)$_2$CO$_2$(CH$_2$)$_2$CH$_3$ | H |
| 477 | —CO$_2$CH$_2$CH$_3$ | CN | CH$_3$ | H | —(CH$_2$)$_2$CO$_2$CH(CH$_3$)$_2$ | H |
| 478 | —CO$_2$CH$_2$CH$_3$ | CN | CH$_3$ | H | —(CH$_2$)$_2$CO$_2$(CH$_2$)$_3$CH$_3$ | H |
| 479 | —CO$_2$CH$_2$CH$_3$ | CN | CH$_3$ | H | —(CH$_2$)$_2$CO$_2$CH(CH$_3$)CH$_2$CH$_3$ | H |
| 480 | —CO$_2$CH$_2$CH$_3$ | CN | CH$_3$ | H | —(CH$_2$)$_2$CO$_2$CH$_2$C$_6$H$_5$ | H |
| 481 | —CO$_2$CH$_2$CH$_3$ | CN | CH$_3$ | H | —(CH$_2$)$_2$CO$_2$(CH$_2$)$_2$OCH$_3$ | H |
| 482 | —CO$_2$CH$_2$CH$_3$ | CN | CH$_3$ | H | —(CH$_2$)$_2$CO$_2$(CH$_2$)$_2$OCH$_2$CH$_3$ | H |
| 483 | —CO$_2$CH$_2$CH$_3$ | CN | CH$_3$ | H | —(CH$_2$)$_2$CO$_2$(CH$_2$)$_3$OCH$_3$ | H |
| 484 | —CO$_2$CH$_2$CH$_3$ | CN | CH$_3$ | H | —(CH$_2$)$_2$CO$_2$(CH$_2$)$_3$OCH$_2$CH$_3$ | H |
| 485 | CN | —CO$_2$CH$_2$CH$_3$ | CH$_3$ | H | —(CH$_2$)$_2$CO$_2$H | H |
| 486 | CN | —CO$_2$CH$_2$CH$_3$ | CH$_3$ | H | —(CH$_2$)$_2$CO$_2$CH$_3$ | H |
| 487 | CN | —CO$_2$CH$_2$CH$_3$ | CH$_3$ | H | —(CH$_2$)$_2$CO$_2$CH$_2$CH$_3$ | H |
| 488 | CN | —CO$_2$CH$_2$CH$_3$ | CH$_3$ | H | —(CH$_2$)$_2$CO$_2$(CH$_2$)$_2$CH$_3$ | H |
| 489 | CN | —CO$_2$CH$_2$CH$_3$ | CH$_3$ | H | —(CH$_2$)$_2$CO$_2$CH(CH$_3$)$_2$ | H |
| 490 | CN | —CO$_2$CH$_2$CH$_3$ | CH$_3$ | H | —(CH$_2$)$_2$CO$_2$(CH$_2$)$_3$CH$_3$ | H |
| 491 | CN | —CO$_2$CH$_2$CH$_3$ | CH$_3$ | H | —(CH$_2$)$_2$CO$_2$CH(CH$_3$)CH$_2$CH$_3$ | H |

TABLE 5-continued (I-e)

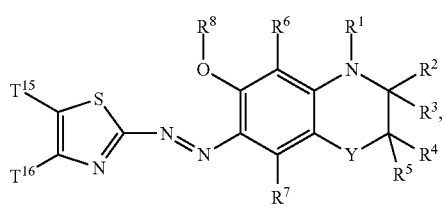

$R^3$ to $R^7$ is hydrogen, Y is carbonyl

| Expl. | $T^{12}$ | $T^{14}$ | $T^{13}$ | $R^2$ | $R^1$ | $R^8$ |
|---|---|---|---|---|---|---|
| 492 | CN | —CO$_2$CH$_2$CH$_3$ | CH$_3$ | H | —(CH$_2$)$_2$CO$_2$CH$_2$C$_6$H$_5$ | H |
| 493 | CN | —CO$_2$CH$_2$CH$_3$ | CH$_3$ | H | —(CH$_2$)$_2$CO$_2$(CH$_2$)$_2$OCH$_3$ | H |
| 494 | CN | —CO$_2$CH$_2$CH$_3$ | CH$_3$ | H | —(CH$_2$)$_2$CO$_2$(CH$_2$)$_2$OCH$_2$CH$_3$ | H |
| 495 | CN | —CO$_2$CH$_2$CH$_3$ | CH$_3$ | H | —(CH$_2$)$_2$CO$_2$(CH$_2$)$_3$OCH$_3$ | H |
| 496 | CN | —CO$_2$CH$_2$CH$_3$ | CH$_3$ | H | —(CH$_2$)$_2$CO$_2$(CH$_2$)$_3$OCH$_2$CH$_3$ | H |
| 497 | NO$_2$ | —CO$_2$CH$_2$CH$_3$ | H | H | —(CH$_2$)$_2$CO$_2$H | H |
| 498 | NO$_2$ | —CO$_2$CH$_2$CH$_3$ | H | H | —(CH$_2$)$_2$CO$_2$CH$_3$ | H |
| 499 | NO$_2$ | —CO$_2$CH$_2$CH$_3$ | H | H | —(CH$_2$)$_2$CO$_2$CH$_2$CH$_3$ | H |
| 500 | NO$_2$ | —CO$_2$CH$_2$CH$_3$ | H | H | —(CH$_2$)$_2$CO$_2$(CH$_2$)$_2$CH$_3$ | H |
| 501 | NO$_2$ | —CO$_2$CH$_2$CH$_3$ | H | H | —(CH$_2$)$_2$CO$_2$CH(CH$_3$)$_2$ | H |
| 502 | NO$_2$ | —CO$_2$CH$_2$CH$_3$ | H | H | —(CH$_2$)$_2$CO$_2$(CH$_2$)$_3$CH$_3$ | H |
| 503 | NO$_2$ | —CO$_2$CH$_2$CH$_3$ | H | H | —(CH$_2$)$_2$CO$_2$CH(CH$_3$)CH$_2$CH$_3$ | H |
| 504 | NO$_2$ | —CO$_2$CH$_2$CH$_3$ | H | H | —(CH$_2$)$_2$CO$_2$CH$_2$C$_6$H$_5$ | H |
| 505 | NO$_2$ | —CO$_2$CH$_2$CH$_3$ | H | H | —(CH$_2$)$_2$CO$_2$(CH$_2$)$_2$OCH$_3$ | H |
| 506 | NO$_2$ | —CO$_2$CH$_2$CH$_3$ | H | H | —(CH$_2$)$_2$CO$_2$(CH$_2$)$_2$OCH$_2$CH$_3$ | H |
| 507 | NO$_2$ | —CO$_2$CH$_2$CH$_3$ | H | H | —(CH$_2$)$_2$CO$_2$(CH$_2$)$_3$OCH$_3$ | H |
| 508 | NO$_2$ | —CO$_2$CH$_2$CH$_3$ | H | H | —(CH$_2$)$_2$CO$_2$(CH$_2$)$_3$OCH$_2$CH$_3$ | H |
| 509 | NO$_2$ | —CO$_2$CH$_2$CH$_3$ | H | CH$_3$ | —CH(CH$_3$)CO$_2$(CH$_2$)$_2$CH$_3$ | H |
| 510 | NO$_2$ | —CO$_2$CH$_2$CH$_3$ | H | H | —(CH$_2$)$_2$CO$_2$(CH$_2$)$_3$OCH$_2$CH$_3$ | H |

Also preferred are dyes as described above having formula (I-f)

(I-f)

wherein
$T^{15}$ and $T^{16}$ independent from each other is hydrogen, halogen, (C$_1$-C$_6$)-alkyl, nitro, cyano, formyl, acetyl, (C$_1$-C$_6$)-alkoxycarbonyl, O-interrupted (C$_1$-C$_6$)-alkyl, S-interrupted (C$_1$-C$_6$)-alkyl or aryl,
$R^1$ is methyl, ethyl, propyl, isopropyl, n-butyl, isobutyl, benzyl, 2-methoxyethyl, 2-ethoxyethyl, 2-acetoxyethyl, 2-(propionyl)oxyethyl, 2-(benzoyl)oxyethyl, cyanomethyl, 2-cyanoethyl, 3-cyanopropyl, 3-(C$_1$-C$_6$)alkoxyl-3-oxopropyl, 3-[O-interrupted (C$_2$-C$_6$)-alkoxyl]-3-oxopropyl, 2-(C$_1$-C$_6$)alkyl-2-oxoethyl, 2-[O-interrupted (C$_2$-C$_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[(C$_1$-C$_6$)alkylacyl]-methoxyl}-3-oxopropyl, 3-[(arylacyl)-methoxy]-3-oxopropyl, 3-{[(C$_1$-C$_6$)-alkoxycabonyl]methoxy}-3-oxopropyl, 2-{[(C$_1$-C$_6$)-alkoxycabonyl]methoxy}-2-oxoethyl or 2-{[(C$_1$-C$_6$)alkylacyl]-methoxyl}-2-oxoethyl,
$R^2$ to $R^7$ independent from each other is hydrogen, (C$_1$-C$_6$) alkyl, aryl, (C$_1$-C$_8$)alkoxyl, (C$_3$-C$_8$)cycloalkyl, O-interrupted (C$_2$-C$_6$)alkyl, S-interrupted (C$_2$-C$_6$)alkyl or halogen,
$R^8$ is hydrogen, (C$_1$-C$_6$)alkyl, (C$_3$-C$_4$)-alkenyl, (C$_3$-C$_4$)-alkynyl, arylmethyl, 2-(C$_1$-C$_6$)alkoxyl-2-oxoethyl, 2-(arylmethyl)-2-oxoethyl, cyano(C$_1$-C$_6$)alkyl, O-interrupted (C$_1$-C$_6$)alkyl or S-interrupted (C$_1$-C$_6$)alkyl
and
Y is carbonyl.

Examples of preferred dyes of the formula (I-f) are the compounds illustrated in Table 6 and mixtures thereof.

TABLE 6

(I-f)

$R^3$ to $R^7$ is hydrogen, Y is carbonyl

| Example | $T^{15}$ | $T^{16}$ | $R^2$ | $R^1$ | $R^8$ |
|---|---|---|---|---|---|
| 511 | NO$_2$ | H | H | —(CH$_2$)$_2$CO$_2$H | H |
| 512 | NO$_2$ | H | H | —(CH$_2$)$_2$CO$_2$CH$_3$ | H |
| 513 | NO$_2$ | H | H | —(CH$_2$)$_2$CO$_2$CH$_2$CH$_3$ | H |
| 514 | NO$_2$ | H | H | —(CH$_2$)$_2$CO$_2$(CH$_2$)$_2$CH$_3$ | H |
| 515 | NO$_2$ | H | H | —(CH$_2$)$_2$CO$_2$CH(CH$_3$)$_2$ | H |
| 516 | NO$_2$ | H | H | —(CH$_2$)$_2$CO$_2$(CH$_2$)$_3$CH$_3$ | H |
| 517 | NO$_2$ | H | H | —(CH$_2$)$_2$CO$_2$CH(CH$_3$)CH$_2$CH$_3$ | H |
| 518 | NO$_2$ | H | H | —(CH$_2$)$_2$CO$_2$CH$_2$C$_6$H$_5$ | H |
| 519 | NO$_2$ | H | H | —(CH$_2$)$_2$CO$_2$(CH$_2$)$_2$OCH$_3$ | H |
| 520 | NO$_2$ | H | H | —(CH$_2$)$_2$CO$_2$(CH$_2$)$_2$OCH$_2$CH$_3$ | H |
| 521 | NO$_2$ | H | H | —(CH$_2$)$_2$CO$_2$(CH$_2$)$_3$OCH$_3$ | H |
| 522 | NO$_2$ | H | H | —(CH$_2$)$_2$CO$_2$(CH$_2$)$_3$OCH$_2$CH$_3$ | H |
| 523 | —CHO | Cl | H | —(CH$_2$)$_2$CO$_2$H | H |
| 524 | —CHO | Cl | H | —(CH$_2$)$_2$CO$_2$CH$_3$ | H |

TABLE 6-continued

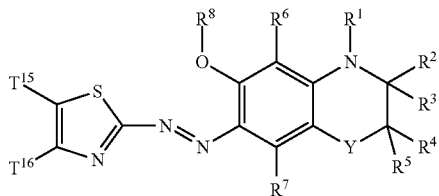

(I-f)

R³ to R⁷ is hydrogen, Y is carbonyl

| Example | $T^{15}$ | $T^{16}$ | $R^2$ | $R^1$ | $R^8$ |
|---|---|---|---|---|---|
| 525 | —CHO | Cl | H | —(CH$_2$)$_2$CO$_2$CH$_2$CH$_3$ | H |
| 526 | —CHO | Cl | H | —(CH$_2$)$_2$CO$_2$(CH$_2$)$_2$CH$_3$ | H |
| 527 | —CHO | Cl | H | —(CH$_2$)$_2$CO$_2$CH(CH$_3$)$_2$ | H |
| 528 | —CHO | Cl | H | —(CH$_2$)$_2$CO$_2$(CH$_2$)$_3$CH$_3$ | H |
| 529 | —CHO | Cl | H | —(CH$_2$)$_2$CO$_2$CH(CH$_3$)CH$_2$CH$_3$ | H |
| 530 | —CHO | Cl | H | —(CH$_2$)$_2$CO$_2$CH$_2$C$_6$H$_5$ | H |
| 531 | —CHO | Cl | H | —(CH$_2$)$_2$CO$_2$(CH$_2$)$_2$OCH$_3$ | H |
| 532 | —CHO | Cl | H | —(CH$_2$)$_2$CO$_2$(CH$_2$)$_2$OCH$_2$CH$_3$ | H |
| 533 | —CHO | Cl | H | —(CH$_2$)$_2$CO$_2$(CH$_2$)$_3$OCH$_3$ | H |
| 534 | —CHO | Cl | H | —(CH$_2$)$_2$CO$_2$(CH$_2$)$_3$OCH$_2$CH$_3$ | H |
| 535 | —CHO | Cl | H | —CH(CH$_3$)CO$_2$CH$_2$CH$_3$ | H |
| 536 | —CHO | Cl | H | —(CH$_2$)$_2$CO$_2$CH$_2$CH$_3$ | —CH$_3$ |

Another preferred group of dyes are dyes as described above having formula (I-g)

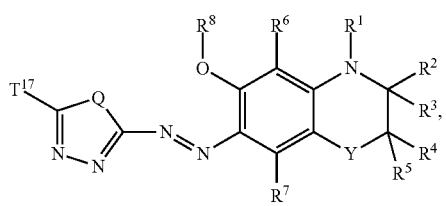

(I-g)

wherein
$T^{17}$ is aryl or (C$_1$-C$_6$)-thioalkoxyl,
Q is oxygen or sulphur,
$R^1$ is methyl, ethyl, propyl, isopropyl, n-butyl, isobutyl, benzyl, 2-methoxyethyl, 2-ethoxyethyl, 2-acetoxyethyl, 2-(propionyl)oxyethyl, 2-(benzoyl)oxyethyl, cyanomethyl, 2-cyanoethyl, 3-cyanopropyl, 3-(C$_1$-C$_6$)alkoxyl-3-oxopropyl, 3-[O-interrupted (C$_2$-C$_6$)-alkoxyl]-3-oxopropyl, 2-(C$_1$-C$_6$)alkyl-2-oxoethyl, 2-[O-interrupted (C$_2$-C$_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[(C$_1$-C$_6$)alkylacyl]-methoxyl}-3-oxopropyl, 3-[(arylacyl)-methoxy]-3-oxopropyl, 3-{[(C$_1$-C$_6$)-alkoxycabonyl]methoxy}-3-oxopropyl, 2-{[(C$_1$-C$_6$)-alkoxycabonyl]methoxy}-2-oxoethyl or 2-{[(C$_1$-C$_6$) alkylacyl]-methoxyl}-2-oxoethyl,
$R^2$ to $R^7$ independent from each other is hydrogen, (C$_1$-C$_6$) alkyl, aryl, (C$_1$-C$_8$)alkoxyl, (C$_3$-C$_8$)cycloalkyl, O-interrupted (C$_2$-C$_6$)alkyl, S-interrupted (C$_2$-C$_6$)alkyl, halogen,
$R^8$ is hydrogen, (C$_1$-C$_6$)alkyl, (C$_3$-C$_4$)-alkenyl, (C$_3$-C$_4$)-alkynyl, arylmethyl, 2-(C$_1$-C$_6$)alkoxyl-2-oxoethyl, 2-(arylmethyl)-2-oxoethyl, cyano(C$_1$-C$_6$)alkyl, O-interrupted (C$_1$-C$_6$)alkyl or S-interrupted (C$_1$-C$_6$)alkyl
and
Y is carbonyl.

Examples of preferred dyes of the formula (I-g) are the compounds illustrated in Table 7 and mixtures thereof.

TABLE 7

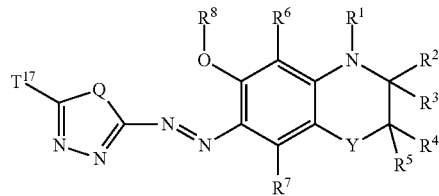

(I-g)

R³ to R⁷ is hydrogen, Y is carbonyl and Q is sulphur

| Example | $T^{17}$ | $R^1$ | $R^2$ | $R^8$ |
|---|---|---|---|---|
| 537 | —SCH$_2$CH$_3$ | —CH$_2$CH$_3$ | H | H |
| 538 | —SCH$_2$CH$_3$ | —CH$_2$C$_6$H$_5$ | H | H |
| 539 | —SCH$_2$CH$_3$ | —(CH$_2$)$_2$CN | H | H |
| 540 | —SCH$_2$CH$_3$ | —CH$_3$ | H | H |
| 541 | —SCH$_2$CH$_3$ | —CH$_2$CH$_3$ | —CH$_3$ | H |
| 542 | —SCH$_2$CH$_3$ | —CH$_2$CH$_3$ | H | H |
| 543 | —SCH$_2$CH$_3$ | —CH(CH$_3$)$_2$ | H | H |
| 544 | —SCH$_2$CH$_3$ | —(CH$_2$)$_3$CH$_3$ | H | H |
| 545 | —SCH$_2$CH$_3$ | —CH(CH$_3$)CH$_2$CH$_3$ | H | H |
| 546 | —SCH$_2$CH$_3$ | —CH$_2$CO$_2$CH$_3$ | H | H |
| 547 | —SCH$_2$CH$_3$ | —CH$_2$CO$_2$CH$_2$CH$_3$ | H | H |
| 548 | —SCH$_2$CH$_3$ | —(CH$_2$)$_2$CO$_2$H | H | H |
| 549 | —SCH$_2$CH$_3$ | —(CH$_2$)$_2$CO$_2$CH$_3$ | H | H |
| 550 | —SCH$_2$CH$_3$ | —(CH$_2$)$_2$CO$_2$CH$_2$CH$_3$ | H | H |
| 551 | —SCH$_2$CH$_3$ | —(CH$_2$)$_2$CO$_2$(CH$_2$)$_2$CH$_3$ | H | H |
| 552 | —SCH$_2$CH$_3$ | —(CH$_2$)$_2$CO$_2$CH(CH$_3$)$_2$ | H | H |
| 553 | —SCH$_2$CH$_3$ | —(CH$_2$)$_2$CO$_2$(CH$_2$)$_3$CH$_3$ | H | H |
| 554 | —SCH$_2$CH$_3$ | —(CH$_2$)$_2$CO$_2$CH(CH$_3$)CH$_2$CH$_3$ | H | H |
| 555 | —SCH$_2$CH$_3$ | —(CH$_2$)$_2$CO$_2$CH$_2$C$_6$H$_5$ | H | H |
| 556 | —SCH$_2$CH$_3$ | —(CH$_2$)$_2$CO$_2$(CH$_2$)$_2$OCH$_3$ | H | H |
| 557 | —SCH$_2$CH$_3$ | —(CH$_2$)$_2$CO$_2$(CH$_2$)$_2$OCH$_2$CH$_3$ | H | H |
| 558 | —SCH$_2$CH$_3$ | —(CH$_2$)$_2$CO$_2$(CH$_2$)$_3$OCH$_3$ | H | H |
| 559 | —SCH$_2$CH$_3$ | —(CH$_2$)$_2$CO$_2$(CH$_2$)$_3$OCH$_2$CH$_3$ | H | H |
| 560 | —SCH$_2$CH$_3$ | —CH(CH$_3$)CO$_2$CH$_2$CH$_3$ | —CH$_3$ | H |
| 561 | —SCH$_2$CH$_3$ | —(CH$_2$)$_2$CO$_2$CH$_2$CH$_3$ | H | —CH$_3$ |

Also preferred are dyes as described above having formula (I-h)

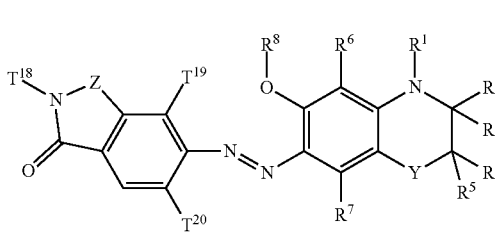

(I-h)

wherein
$T^{18}$ is (C$_1$-C$_6$)alkyl, (C$_1$-C$_6$)-acyloxy substituted (C$_1$-C$_6$) alkyl, cyano(C$_1$-C$_6$)alkyl, arylmethyl, arylcarbonyl substituted (C$_1$-C$_6$)alkyl, 2-(C$_1$-C$_6$)alkoxyl-2-oxoethyl, O-interrupted (C$_1$-C$_6$)-alkyl, S-interrupted (C$_1$-C$_6$)-alkyl or aryl,
$T^{19}$ and $T^{20}$ independent from each other are hydrogen, halogen, cyano, nitro or trifluoromethyl,
Z is a carbonyl or a sulfonyl rest,
$R^1$ is methyl, ethyl, propyl, isopropyl, n-butyl, isobutyl, benzyl, 2-methoxyethyl, 2-ethoxyethyl, 2-acetoxyethyl, 2-(propionyl)oxyethyl, 2-(benzoyl)oxyethyl, cyanomethyl, 2-cyanoethyl, 3-cyanopropyl, 3-(C$_1$-C$_6$)alkoxyl-3-oxopropyl, 3-[O-interrupted (C$_2$-C$_6$)-alkoxyl]-3-oxopropyl, 2-(C$_1$-C$_6$)alkyl-2-oxoethyl, 2-[O-interrupted (C$_2$-C$_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[($C_1$-$C_6$)alkylacyl]-methoxyl}-3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)-alkoxycabonyl]methoxy}-2-oxoethyl or 2-{[($C_1$-$C_6$) alkylacyl]-methoxyl}-2-oxoethyl, $R^2$ to $R^7$ independent from each other is hydrogen, ($C_1$-$C_6$) alkyl, aryl, ($C_1$-$C_8$)alkoxyl, ($C_3$-$C_8$)cycloalkyl, O-interrupted ($C_2$-$C_6$)alkyl, S-interrupted ($C_2$-$C_6$)alkyl or halogen, $R^8$ is hydrogen, ($C_1$-$C_6$)alkyl, ($C_3$-$C_4$)-alkenyl, ($C_3$-$C_4$)-alkynyl, arylmethyl, 2-($C_1$-$C_6$)alkoxyl-2-oxoethyl, 2-(arylmethyl)-2-oxoethyl, cyano($C_1$-$C_6$)alkyl, O-interrupted ($C_1$-$C_6$)alkyl or S-interrupted ($C_1$-$C_6$)alkyl
and
Y is carbonyl.

Examples of preferred dyes of the formula (I-h) are the compounds illustrated in Table 8 and mixtures thereof.

TABLE 8

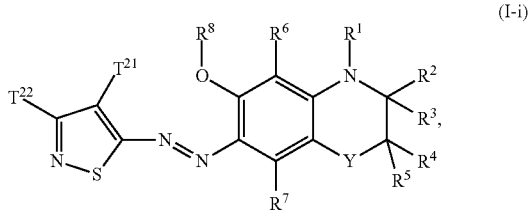

(I-h)

$R^3$ to $R^7$ is hydrogen, Y and Z are carbonyl

| Example | $T^{18}$ | $T^{19}$ | $T^{20}$ | $R^2$ | $R^1$ | $R^8$ |
|---|---|---|---|---|---|---|
| 562 | —$CH_2CH_3$ | CN | CN | H | —$(CH_2)_2CO_2CH_2CH_3$ | H |
| 563 | —$CH_2CH_3$ | CN | CN | H | —$(CH_2)_2CO_2CH_3$ | H |
| 564 | —$CH_2CH_3$ | Br | Br | H | —$(CH_2)_2CO_2CH_2CH_3$ | H |
| 565 | —$CH_2CH_3$ | Br | Br | H | —$(CH_2)_2CO_2CH_3$ | H |
| 566 | —$CH_2CH_3$ | H | Br | H | —$(CH_2)_2CO_2CH_2CH_3$ | H |
| 567 | —$CH_2CH_3$ | H | Br | H | —$(CH_2)_2CO_2CH_3$ | H |
| 568 | —$CH_2CH_3$ | H | CN | H | —$(CH_2)_2CO_2CH_2CH_3$ | H |
| 569 | —$CH_2CH_3$ | H | CN | H | —$(CH_2)_2CO_2CH_3$ | H |
| 570 | —$CH_2CH_3$ | H | H | H | —$(CH_2)_2CO_2CH_2CH_3$ | H |
| 571 | —$CH_2CH_3$ | H | H | H | —$(CH_2)_2CO_2CH_3$ | H |

Preferred dyes according to the present invention are also those as described above having formula (I-i)

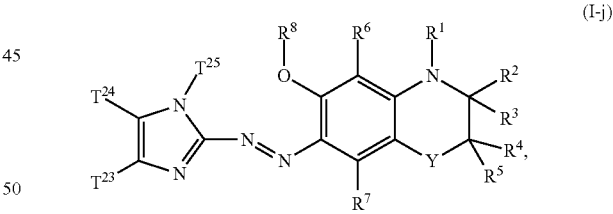

(I-i)

wherein
$T^{21}$ is cyano, nitro or ($C_1$-$C_6$)-alkoxycarbonyl,
$T^{22}$ is ($C_1$-$C_6$)-alkyl, hydrogen, halogen or aryl,
$R^1$ is methyl, ethyl, propyl, isopropyl, n-butyl, isobutyl, benzyl, 2-methoxyethyl, 2-ethoxyethyl, 2-acetoxyethyl, 2-(propionyl)oxyethyl, 2-(benzoyl)oxyethyl, cyanomethyl, 2-cyanoethyl, 3-cyanopropyl, 3-($C_1$-$C_6$)alkoxyl-3-oxopropyl, 3-[O-interrupted ($C_2$-$C_6$)-alkoxyl]-3-oxopropyl, 2-($C_1$-$C_6$)alkyl-2-oxoethyl, 2-[O-interrupted ($C_2$-$C_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[($C_1$-$C_6$)alkylacyl]-methoxyl}-3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)-alkoxycabonyl]methoxy}-2-oxoethyl or 2-{[($C_1$-$C_6$) alkylacyl]-methoxyl}-2-oxoethyl, $R^2$ to $R^7$ independent from each other is hydrogen, ($C_1$-$C_6$) alkyl, aryl, ($C_1$-$C_8$)alkoxyl, ($C_3$-$C_8$)cycloalkyl, O-interrupted ($C_2$-$C_6$)alkyl, S-interrupted ($C_2$-$C_6$)alkyl or halogen, $R^8$ is hydrogen, ($C_1$-$C_6$)alkyl, ($C_3$-$C_4$)-alkenyl, ($C_3$-$C_4$)-alkynyl, arylmethyl, 2-($C_1$-$C_6$)alkoxyl-2-oxoethyl, 2-(arylmethyl)-2-oxoethyl, cyano($C_1$-$C_6$)alkyl, O-interrupted ($C_1$-$C_6$)alkyl or S-interrupted ($C_1$-$C_6$)alkyl
and
Y is carbonyl.

Examples of preferred dyes of the formula (I-i) are the compounds illustrated in Table 9 and mixtures thereof.

TABLE 9

(I-i)

$R^3$ to $R^7$ is hydrogen, Y is carbonyl

| Example | $T^{21}$ | $T^{22}$ | $R^2$ | $R^1$ | $R^8$ |
|---|---|---|---|---|---|
| 572 | CN | —$C_6H_5$ | H | —$CH_2CH_3$ | H |
| 573 | CN | —$C_6H_5$ | H | —$(CH_2)_2CO_2CH_3$ | H |
| 574 | CN | —$C_6H_5$ | H | —$(CH_2)_2CN$ | H |
| 575 | CN | Cl | H | —$CH_2CH_3$ | H |
| 576 | CN | Cl | H | —$(CH_2)_2CO_2CH_2CH_3$ | H |
| 577 | CN | Cl | H | —$(CH_2)_2CN$ | H |
| 578 | CN | Cl | H | —$(CH_2)_2CN$ | —$CH_3$ |

Another preferred embodiment of the present invention are dyes as described above having formula (I-j)

(I-j)

wherein
$T^{23}$ and $T^{24}$ independent from each other is cyano, nitro, halogen, aryl or trifluoromethyl,
$T^{25}$ is hydrogen, ($C_1$-$C_6$)-alkyl, O-interrupted ($C_1$-$C_6$)-alkyl, S-interrupted ($C_1$-$C_6$)-alkyl or aryl,
$R^1$ is methyl, ethyl, propyl, isopropyl, n-butyl, isobutyl, benzyl, 2-methoxyethyl, 2-ethoxyethyl, 2-acetoxyethyl, 2-(propionyl)oxyethyl, 2-(benzoyl)oxyethyl, cyanomethyl, 2-cyanoethyl, 3-cyanopropyl, 3-($C_1$-$C_6$)alkoxyl-3-oxopropyl, 3-[O-interrupted ($C_2$-$C_6$)-alkoxyl]-3-oxopropyl, 2-($C_1$-$C_6$)alkyl-2-oxoethyl, 2-[O-interrupted ($C_2$-$C_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[($C_1$-$C_6$)alkylacyl]-methoxyl}-

3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)-alkoxycabonyl]methoxy}-2-oxoethyl or 2-{[($C_1$-$C_6$)alkylacyl]-methoxyl}-2-oxoethyl, Each of $R^2$ to $R^7$, independent from each other, is hydrogen, ($C_1$-$C_6$)alkyl, aryl, ($C_1$-$C_8$)alkoxyl, ($C_3$-$C_8$)cycloalkyl, O-interrupted ($C_2$-$C_6$)alkyl, S-interrupted ($C_2$-$C_6$)alkyl or halogen, $R^8$ is hydrogen, ($C_1$-$C_6$)alkyl, ($C_3$-$C_4$)-alkenyl, ($C_3$-$C_4$)-alkynyl, arylmethyl, 2-($C_1$-$C_6$)alkoxyl-2-oxoethyl, 2-(arylmethyl)-2-oxoethyl, cyano($C_1$-$C_6$)alkyl, O-interrupted ($C_1$-$C_6$)alkyl or S-interrupted ($C_1$-$C_6$)alkyl and Y is carbonyl.

Examples of preferred dyes of the formula (I-j) are the compounds illustrated in Table 10, and mixtures thereof

TABLE 10

(I-j)

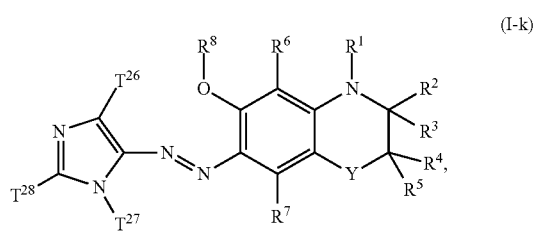

$R^3$ to $R^7$ is hydrogen, Y is carbonyl

| Example | $T^{23}$ | $T^{24}$ | $T^{25}$ | $R^2$ | $R^1$ | $R^8$ |
|---|---|---|---|---|---|---|
| 579 | CN | CN | —$CH_2CN$ | H | —$(CH_2)_2CO_2H$ | H |
| 580 | CN | CN | —$CH_2CN$ | H | —$(CH_2)_2CO_2CH_3$ | H |
| 581 | CN | CN | —$CH_2CN$ | H | —$(CH_2)_2CO_2CH_2CH_3$ | H |
| 582 | CN | CN | —$CH_2CN$ | H | —$(CH_2)_2CO_2(CH_2)_2CH_3$ | H |
| 583 | CN | CN | —$CH_2CN$ | H | —$(CH_2)_2CO_2CH(CH_3)_2$ | H |
| 584 | CN | CN | —$CH_2CN$ | H | —$(CH_2)_2CO_2(CH_2)_3CH_3$ | H |
| 585 | CN | CN | —$CH_2CN$ | H | —$(CH_2)_2CO_2CH(CH_3)CH_2CH_3$ | H |
| 586 | CN | CN | —$CH_2CN$ | H | —$(CH_2)_2CO_2CH_2C_6H_5$ | H |
| 587 | CN | CN | —$CH_2CN$ | H | —$(CH_2)_2CO_2(CH_2)_2OCH_3$ | H |
| 588 | CN | CN | —$CH_2CN$ | H | —$(CH_2)_2CO_2(CH_2)_2OCH_2CH_3$ | H |
| 589 | CN | CN | —$CH_2CN$ | H | —$(CH_2)_2CO_2(CH_2)_3OCH_3$ | H |
| 590 | CN | CN | —$CH_2CN$ | H | —$(CH_2)_2CO_2(CH_2)_3OCH_2CH_3$ | H |
| 591 | CN | CN | —$CH_2CN$ | H | —$(CH_2)_2CO_2CH_2CH_3$ | $CH_3$ |

Another group of preferred dyes are dyes as described above having formula (I-k)

(I-k)

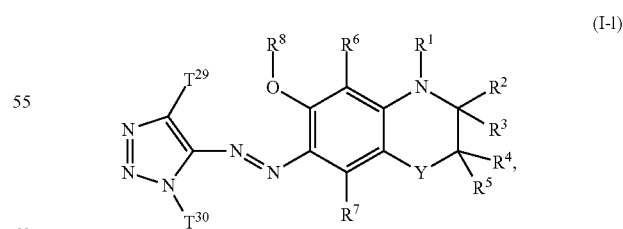

wherein $T^{26}$ is cyano, nitro, aryl or trifluoromethyl, $T^{27}$ is hydrogen, aryl or ($C_1$-$C_6$)-alkyl, $T^{28}$ is hydrogen, ($C_1$-$C_6$)-acyloxy substituted ($C_1$-$C_6$)alkyl, cyano($C_1$-$C_6$)alkyl, aryl, O-interrupted ($C_1$-$C_6$)-alkyl or S-interrupted ($C_1$-$C_6$)-alkyl, $R^1$ is methyl, ethyl, propyl, isopropyl, n-butyl, isobutyl, benzyl, 2-methoxyethyl, 2-ethoxyethyl, 2-acetoxyethyl, 2-(propionyl)oxyethyl, 2-(benzoyl)oxyethyl, cyanomethyl, 2-cyanoethyl, 3-cyanopropyl, 3-($C_1$-$C_6$)alkoxyl-3-oxopropyl, 3-[O-interrupted ($C_2$-$C_6$)-alkoxyl]-3-oxopropyl, 2-($C_1$-$C_6$)alkyl-2-oxoethyl, 2-[O-interrupted ($C_2$-$C_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[($C_1$-$C_6$)alkylacyl]-methoxyl}-3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)-alkoxycabonyl]methoxy}-2-oxoethyl or 2-{[($C_1$-$C_6$)alkylacyl]-methoxyl}-2-oxoethyl, $R^2$ to $R^7$ independent from each other is hydrogen, ($C_1$-$C_6$)alkyl, aryl, ($C_1$-$C_8$)alkoxyl, ($C_3$-$C_8$)cycloalkyl, O-interrupted ($C_2$-$C_6$)alkyl, S-interrupted ($C_2$-$C_6$)alkyl or halogen, $R^8$ is hydrogen, ($C_1$-$C_6$)alkyl, ($C_3$-$C_4$)-alkenyl, ($C_3$-$C_4$)-alkynyl, arylmethyl, 2-($C_1$-$C_6$)alkoxyl-2-oxoethyl, 2-(arylmethyl)-2-oxoethyl, cyano($C_1$-$C_6$)alkyl, O-interrupted ($C_1$-$C_6$)alkyl or S-interrupted ($C_1$-$C_6$)alkyl and Y is carbonyl.

Examples of preferred dyes of the formula (I-k) are the compounds illustrated in Table 11 and mixtures thereof.

TABLE 11

(I-k)

$R^3$ to $R^7$ is hydrogen, Y is carbonyl

| Example | $T^{26}$ | $T^{27}$ | $T^{28}$ | $R^2$ | $R^1$ | $R^8$ |
|---|---|---|---|---|---|---|
| 592 | $NO_2$ | $CH_3$ | H | H | —$(CH_2)_2CO_2H$ | H |
| 593 | $NO_2$ | $CH_3$ | H | H | —$(CH_2)_2CO_2CH_3$ | H |
| 594 | $NO_2$ | $CH_3$ | H | H | —$(CH_2)_2CO_2CH_2CH_3$ | H |
| 595 | $NO_2$ | $CH_3$ | H | H | —$(CH_2)_2CO_2(CH_2)_2CH_3$ | H |
| 596 | $NO_2$ | $CH_3$ | H | H | —$(CH_2)_2CO_2CH(CH_3)_2$ | H |
| 597 | $NO_2$ | $CH_3$ | H | H | —$(CH_2)_2CO_2(CH_2)_3CH_3$ | H |
| 598 | $NO_2$ | $CH_3$ | H | H | —$(CH_2)_2CO_2CH(CH_3)CH_2CH_3$ | H |
| 599 | $NO_2$ | $CH_3$ | H | H | —$(CH_2)_2CO_2CH_2C_6H_5$ | H |
| 600 | $NO_2$ | $CH_3$ | H | H | —$(CH_2)_2CO_2(CH_2)_2OCH_3$ | H |
| 601 | $NO_2$ | $CH_3$ | H | H | —$(CH_2)_2CO_2(CH_2)_2OCH_2CH_3$ | H |
| 602 | $NO_2$ | $CH_3$ | H | H | —$(CH_2)_2CO_2(CH_2)_3OCH_3$ | H |
| 603 | $NO_2$ | $CH_3$ | H | H | —$(CH_2)_2CO_2(CH_2)_3OCH_2CH_3$ | H |
| 604 | $NO_2$ | $CH_3$ | H | H | —$(CH_2)_2CO_2CH_2CH_3$ | $CH_3$ |

Preferred are dyes as described above having formula (I-l)

(I-l)

wherein $T^{29}$ is cyano, nitro, aryl or trifluoromethyl, $T^{30}$ is hydrogen, ($C_1$-$C_6$)-alkyl, cyano($C_1$-$C_6$)alkyl, O-interrupted ($C_1$-$C_6$)alkyl, S-interrupted ($C_1$-$C_6$)alkyl, aryl, benzyl, ($C_1$-$C_6$)-acyloxy substituted ($C_1$-$C_6$)alkyl or cyano($C_1$-$C_6$)alkyl, R¹ is methyl, ethyl, propyl, isopropyl, n-butyl, isobutyl, benzyl, 2-methoxyethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-($C_1$-$C_6$)alkoxyl-3-oxopropyl, 3-[O-interrupted ($C_2$-$C_6$)-alkoxyl]-3-oxopropyl, 2-($C_1$-$C_6$)alkyl-2-oxoethyl, 2-[O-interrupted ($C_2$-$C_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[($C_1$-$C_6$)alkylacyl]-methoxyl}-3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)-alkoxycabonyl]methoxy}-2-oxoethyl or 2-{[($C_1$-$C_6$)alkylacyl]-methoxyl}-2-oxoethyl, R² to R⁷ independent from each other is hydrogen, ($C_1$-$C_6$) alkyl, aryl, ($C_1$-$C_8$)alkoxyl, ($C_3$-$C_8$)cycloalkyl, O-interrupted ($C_2$-$C_6$)alkyl, S-interrupted ($C_2$-$C_6$)alkyl or halogen, R⁸ is hydrogen, ($C_1$-$C_6$)alkyl, ($C_3$-$C_4$)-alkenyl, ($C_3$-$C_4$)-alkynyl, arylmethyl, 2-($C_1$-$C_6$)alkoxyl-2-oxoethyl, 2-(arylmethyl)-2-oxoethyl, cyano($C_1$-$C_6$)alkyl, O-interrupted ($C_1$-$C_6$)alkyl or S-interrupted ($C_1$-$C_6$)alkyl and Y is carbonyl.

Examples of preferred dyes of the formula (I-l) are the compounds illustrated in Table 12 and mixtures thereof.

TABLE 12

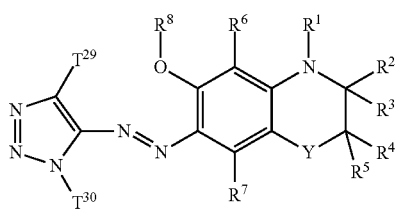

(I-l)

R³ to R⁷ is hydrogen, Y is carbonyl

| Example | T²⁹ | T³⁰ | R² | R¹ | R⁸ |
|---|---|---|---|---|---|
| 605 | CN | —CH₂C₆H₅ | H | —(CH₂)₂CO₂CH₂CH₃ | H |
| 606 | CN | —CH₂C₆H₅ | H | —(CH₂)₂CO₂CH₃ | H |
| 607 | CN | —CH₂C₆H₅ | H | —(CH₂)₂CO₂CH₃ | H |
| 608 | CN | —CH₂C₆H₅ | H | —(CH₂)₂CO₂CH₂CH₃ | H |
| 609 | CN | —CH₂C₆H₅ | H | —(CH₂)₂CO₂CH₂CH₃ | —CH₃ |

Preferred are also dyes as described above having formula (I-m)

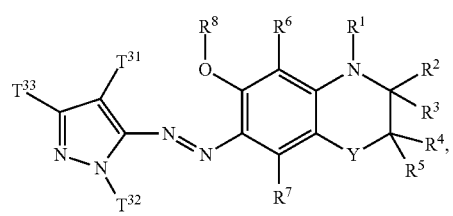

(I-m)

wherein

T³¹ is cyano, nitro, aryl or trifluoromethyl,

T³² is hydrogen, ($C_1$-$C_6$)-alkyl, O-interrupted ($C_1$-$C_6$)-alkyl, S-interrupted ($C_1$-$C_6$)-alkyl, cyano($C_1$-$C_6$)alkyl, arylmethyl, cyano($C_1$-$C_6$)alkyl or ($C_1$-$C_6$)-acyloxy substituted ($C_1$-$C_6$) alkyl, T³³ is hydrogen or ($C_1$-$C_6$)alkyl, R¹ is methyl, ethyl, propyl, isopropyl, n-butyl, isobutyl, benzyl, 2-methoxyethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-($C_1$-$C_6$)alkoxyl-3-oxopropyl, 3-[O-interrupted ($C_2$-$C_6$)-alkoxyl]-3-oxopropyl, 2-($C_1$-$C_6$)alkyl-2-oxoethyl, 2-[O-interrupted ($C_2$-$C_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[($C_1$-$C_6$)alkylacyl]-methoxyl}-3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)-alkoxycabonyl]methoxy}-2-oxoethyl or 2-{[($C_1$-$C_6$)alkylacyl]-methoxyl}-2-oxoethyl, R² to R⁷ independent from each other is hydrogen, ($C_1$-$C_6$) alkyl, aryl, ($C_1$-$C_8$)alkoxyl, ($C_3$-$C_8$)cycloalkyl, O-interrupted ($C_2$-$C_6$)alkyl, S-interrupted ($C_2$-$C_6$)alkyl or halogen, R⁸ is hydrogen, ($C_1$-$C_6$)alkyl, ($C_3$-$C_4$)-alkenyl, ($C_3$-$C_4$)-alkynyl, arylmethyl, 2-($C_1$-$C_6$)alkoxyl-2-oxoethyl, 2-(arylmethyl)-2-oxoethyl, cyano($C_1$-$C_6$)alkyl, O-interrupted ($C_1$-$C_6$)alkyl or S-interrupted ($C_1$-$C_6$)alkyl and Y is carbonyl.

Examples of preferred dyes of the formula (I-m) are the compounds illustrated in Table 13 and mixtures thereof.

TABLE 13

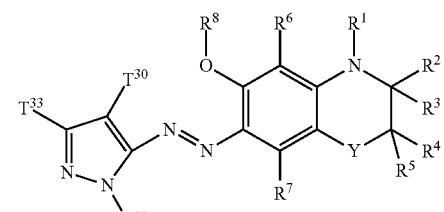

(I-m)

R³ to R⁷ is hydrogen, Y is carbonyl

| Example | T³¹ | T³² | T³³ | R² | R¹ | R⁸ |
|---|---|---|---|---|---|---|
| 610 | CN | H | H | H | —CH₂CH₃ | H |
| 611 | CN | H | CN | H | —(CH₂)₂CO₂CH₃ | H |
| 612 | CN | H | CN | H | —(CH₂)₂CN | H |
| 613 | CN | —C₆H₅ | CN | H | —CH₂CH₃ | H |
| 614 | CN | —C₆H₅ | CN | H | —(CH₂)₂CO₂CH₂CH₃ | H |
| 615 | CN | —C₆H₅ | CN | H | —(CH₂)₂CN | H |
| 616 | CN | —C₆H₅ | CN | H | —(CH₂)₂CN | —CH₃ |

Another preferred group of dyes are those as described above having formula (I-n)

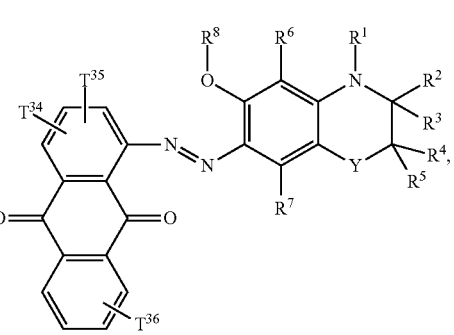

(I-n)

wherein $T^{34}$, $T^{35}$ and $T^{36}$ independent from each other is hydrogen, halogen, nitro, cyano, hydroxyl, $(C_1-C_6)$-alkoxylcarbonyl, $(C_1-C_6)$-alkyl or acyl, $R^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$alkylacyl]-methoxyl}-2-oxoethyl, $R^2$ to $R^7$ independent from each other is hydrogen, $(C_1-C_6)$ alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

Examples of preferred dyes of the formula (I-n) are the compounds illustrated in Table 14, and mixtures thereof.

TABLE 14

| Example | Structure |
|---|---|
| 617 | 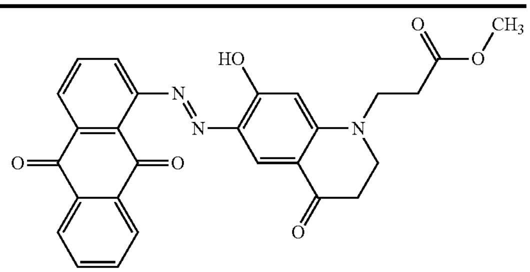 |
| 618 | 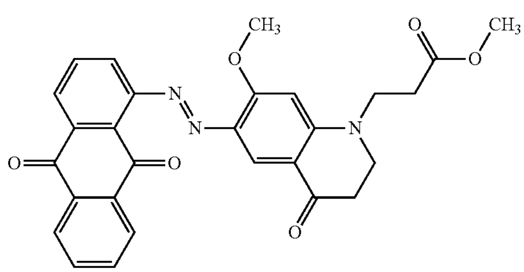 [SMILES: COC(=O)CCN1CCC(=O)c2cc(/N=N/c3cccc4c3C(=O)c3ccccc3C4=O)c(OC)cc21] |
| 619 | 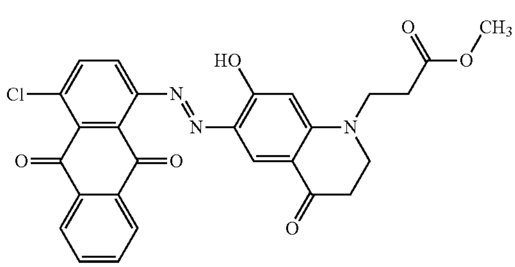 [SMILES: COC(=O)CCN1CCC(=O)c2cc(/N=N/c3ccc(Cl)c4c3C(=O)c3ccccc3C4=O)c(O)cc21] |

TABLE 14-continued

| Example | Structure |
|---|---|
| 620 | 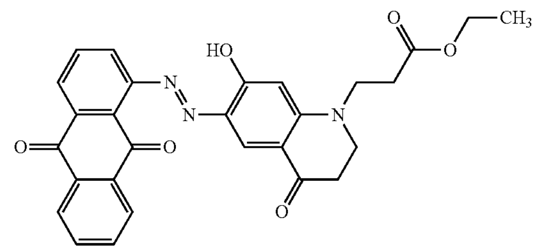 [SMILES: CCOC(=O)CCN1CCC(=O)c2cc(/N=N/c3cccc4c3C(=O)c3ccccc3C4=O)c(O)cc21] |

Just another preferred group of dyes are the dyes as described above having formula (I-o)

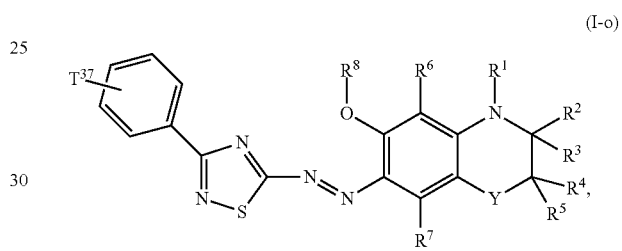

(I-o)

wherein $T^{37}$ is nitro, hydrogen or halogen, $R^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$alkylacyl]-methoxyl}-2-oxoethyl, $R^2$ to $R^7$ independent from each other is hydrogen, $(C_1-C_6)$ alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

Examples of preferred dyes of the formula (I-o) are the compounds illustrated in Table 15, and mixtures thereof

TABLE 15

| Example | Structure |
|---|---|
| 621 | Phenyl-thiadiazole-N=N-[6-position of 7-methoxy-1-(CH2CH2C(O)OCH3)-2,3-dihydroquinolin-4(1H)-one] |
| 622 | Phenyl-thiadiazole-N=N-[6-position of 7-hydroxy-1-(CH2CH2C(O)OCH3)-2,3-dihydroquinolin-4(1H)-one] |
| 623 | Phenyl-thiadiazole-N=N-[6-position of 7-methoxy-1-(CH2CH2C(O)OC2H5)-2,3-dihydroquinolin-4(1H)-one] |
| 624 | Phenyl-thiadiazole-N=N-[6-position of 7-hydroxy-1-(CH2CH2C(O)OC2H5)-2,3-dihydroquinolin-4(1H)-one] |

The present invention also provides a process for the production of dyes having formula (I) and mixtures thereof, comprising a) diazotization of a compound of the general formula (XD)

$$d—NH_2, \quad (XD)$$

wherein
D is as defined above, and
b) reacting the obtained corresponding diazonium salt with a compound of formula (XC)

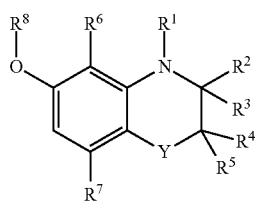

(XC)

wherein $R^1$ to $R^8$ and Y are each as defined above.

The diazotization of the compounds of the general formula (XD) is generally effected in a known manner, for example using sodium nitrite in an aqueous medium rendered acidic, for example with hydrochloric or sulfuric acid, or using nitrosylsulfuric acid in dilute sulfuric acid, phosphoric acid or in a mixture of acetic acid and propionic acid. The preferred temperature range is between 0° C. and 15° C.

The coupling of the diazotized compounds onto the compounds of the general formula (XD) is generally likewise effected in a known manner, for example in an acidic, aqueous, aqueous-organic or organic medium, particularly advantageously at temperatures below 10° C. Acids used are in particular sulfuric acid, acetic acid or propionic acid.

The compounds of the general formulae (XC) and (XD) are known and can be prepared by known methods (e.g. EP 1 154 774, WO 2009/036351, J. Chem. Soc., 1925, 127, 2303, Khim. Geterotsil., 1996, 32(4), 523).

The present invention's dyes of the general formula (I) are very useful for dyeing and printing hydrophobic materials, the dyeings and prints obtained being notable for level hues and high service fastnesses. Deserving of particular mention are excellent wash fastnesses and very good sublimation fastnesses.

The present invention thus also provides for the use of the dyes of the general formula I for dyeing and printing hydrophobic materials, i.e., processes for dyeing or printing such materials in a conventional manner wherein one or more dyes of the general formula (I) according to the present invention are used as a colorant.

The hydrophobic materials mentioned may be of synthetic or semisynthetic origin. Useful hydrophobic materials include for example secondary cellulose acetate, cellulose triacetate, polyamides and, in particular, high molecular weight polyesters. Materials of high molecular weight polyester are in particular those based on polyethylene glycol terephthalates.

The hydrophobic synthetic materials can be present in the form of sheet or threadlike constructions and can have been processed, for example, into yarns or into woven or knit textile materials. Preference is given to fibrous textile materials, which may also be present in the form of micro fibers for example.

The dyeing in accordance with the use provided by the present invention can be carried out in a conventional manner, preferably from an aqueous dispersion, if appropriate in the presence of carriers, at between 80 to about 110° C. by the exhaust process or by the HT process in a dyeing autoclave at 110 to 140° C., but also by the so-called thermo-fix process, in which the fabric is padded with the dyeing liquor and subsequently fixed/set at about 180 to 230° C.

Organic and inorganic acids such as acetic acid, succinic acid, boric acid or phosphoric acid are included to set a pH in the range from 4 to 5, preferably 4.5. It is advantageous to buffer the pH setting and to add a sufficient amount of a buffering system. The acetic acid/sodium acetate system is an example of an advantageous buffering system.

Furthermore, the dyes and dye mixtures according to the invention are also well suited to dyeing hydrophobic fiber materials from supercritical carbon dioxide.

To use the dye or dye mixture in textile printing, the requisite amounts of the abovementioned dye formulations are kneaded in a conventional manner together with thickeners, for example alkali metal alginates or the like, and if appropriate further additives, for example fixation accelerants, wetting agents and oxidizing agents, to give print pastes.

The present invention also provides inks for digital textile printing by the inkjet process, comprising a present invention dye of the general formula (I).

The inks of the present invention are preferably aqueous and comprise one or more of the present invention's dyes of the general formula (I), for example in amounts of 0.1% to 50% by weight, preferably in amounts of 0.5% to 30% by weight and more preferably in amounts of 1% to 15% by weight based on the total weight of the ink. They further comprise in particular from 0.1% to 20% by weight of a dispersant. Suitable dispersants are known to one skilled in the art, are commercially available and include for example sulfonated or sulfomethylated lignins, condensation products of aromatic sulfonic acids and formaldehyde, condensation products of substituted or unsubstituted phenol and formaldehyde, polyacrylates and corresponding copolymers, modified polyurethanes and reaction products of alkylene oxides with alkylatable compounds, for example fatty alcohols, fatty amines, fatty acids, carboxamides and substituted or unsubstituted phenols.

The inks of the present invention may further comprise customary additives, for example viscosity moderators to set viscosities in the range from 1.5 to 40.0 mPas in the temperature range of 20 to 50° C. Preferred inks have a viscosity in the range from 1.5 to 20 mPas and particularly preferred inks have a viscosity in the range from 1.5 to 15 mPas.

Useful viscosity moderators include rheological additives, for example polyvinyl-caprolactam, polyvinylpyrrolidone and also their copolymers, polyetherpolyol, associative thickeners, polyureas, sodium alginates, modified galactomannans, polyetherurea, polyurethane and nonionic cellulose ethers.

By way of further additives, the inks of the present invention may include surface-active substances to set surface tensions in the range from 20 to 65 mN/m, which are if appropriate adapted depending on the process used (thermal or piezo technology). Useful surface-active substances include for example surfactants of any kind, preferably nonionic surfactants, butyldiglycol and 1,2 hexanediol.

The inks may further include customary additives, for example chemical species to inhibit fungal and bacterial growth in amounts from 0.01% to 1% by weight based on the total weight of the ink.

The inks of the present invention can be prepared in conventional manner by mixing the components in water.

The examples below serve to illustrate the invention. Parts and percentages are by weight unless noted otherwise. The relationship between parts by weight and parts by volume is that of the kilogram to the liter.

SYNTHESIS EXAMPLE 1

Preparation of Substance 38

5.24 g of 6-bromo-2,4-dinitroaniline were introduced into a mixture of 9.8 ml of sulfuric acid (96% ic), 0.5 ml of water and 3.5 ml of nitrosylsulfuric acid (40% ic) at 30 to 35° C. After 3 hours of stirring at 30 to 35° C., excess nitrite was destroyed with amidosulfonic acid. The diazonium salt solution thus obtained was expediently added dropwise to a mixture of 4.9 g of 2,3-dihydro-7-hydroxyquinolin-4-keto-1-propionyl methyl ester, 50 ml of methanol and 200 g of ice. After stirring for one hour the solids were filtered off with suction, washed with water and dried to leave 7.9 g of the dye example 38.

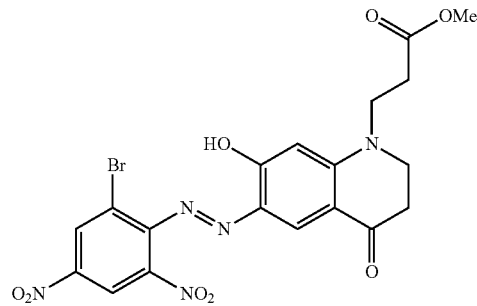

(Example 38)

SYNTHESIS EXAMPLE 2

Preparation of Substance 450

8.16 g of 5-amino-3-methyl-thiophene-2,4-dicarbonitrile were introduced into a mixture of 40 mL of acetic acid, 10 ml of Propionic acid and 9.01 ml of nitrosylsulfuric acid (40%) at 0 to 5° C. After 3 hours of stirring at 0 to 5° C., excess nitrite was destroyed with amidosulfonic acid. The diazonium salt solution thus obtained was expediently added dropwise to a mixture of 12.46 g of 2,3-dihydro-7-hydroxyquinolin-4-keto-1-propionyl methyl ester, 100 ml of methanol and 300 g of ice. After stirring for one hour the solids were filtered off with suction, washed with water and dried to leave 13.0 g of the dye example 450.

(Example 450)

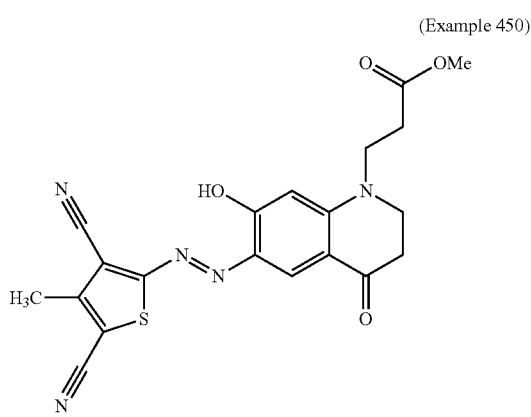 [SMILES: COC(=O)CCN1CCC(=O)c2cc(/N=N/c3sc(C#N)c(C)c3C#N)c(O)cc21]

SYNTHESIS EXAMPLE 3

Preparation of Substance 342

8.69 g of 2,4-dinitroaniline were introduced into a mixture of 20 ml of sulfuric acid (96% ic), 1.2 ml of water and 8.55 ml of nitrosylsulfuric acid (40%) at 30 to 35° C. After 3 hours of stirring at 30 to 35° C., excess nitrite was destroyed with amidosulfonic acid. The diazonium salt solution thus obtained was expediently added dropwise to a mixture of 13.2 g of 2,3-dihydro-7-methoxyquinolin-4-keto-1-propionyl methyl ester, 100 ml of methanol and 300 g of ice. After stirring for one hour the solids were filtered off with suction, washed with water and dried to leave 16.3 g of the Dye example 342.

(Example 342)

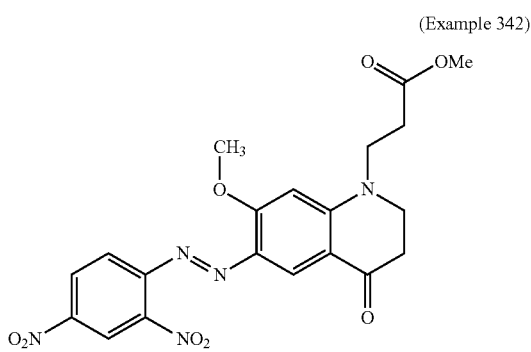 [SMILES: COC(=O)CCN1CCC(=O)c2cc(/N=N/c3ccc([N+](=O)[O-])cc3[N+](=O)[O-])c(OC)cc21]

Through analogy, all the dyes of the present invention can be synthesized according to the methods described above.

APPLICATION EXAMPLE 1

3 g of the dye example 38 were ground in a glass beads mill together with 3 g dispersing reagent and 94 g water, which was converted into 3% aqueous dispersion. Using that formulation, a 1% dyeing (based on dye and substrate) is produced on polyester fabric by high temperature exhaust process at 130° C. and was reduction cleared. The rubine dyeing so obtained has very good in-use fastness properties, especially excellent fastness to washing.

APPLICATION EXAMPLE 2

3 g of the dye example 450 were ground in a glass beads mill together with 3 g dispersing reagent and 94 g water, which was converted into 3% aqueous dispersion. Using that formulation, a 1% dyeing (based on dye and substrate) was produced on polyester fabric by high temperature exhaust process at 130° C. and was reduction cleared. The bright rubine dyeing so obtained has very good in-use fastness properties, especially excellent fastness to washing.

APPLICATION EXAMPLE 3

A textile fabric consisting of polyester was padded with liquor consisting of 50 g/l of 8% sodium alginate solution, 100 g/l 8 to 12% carob flour ether solution and 5 g/l of monosodium phosphate in water and then dried. The wet pickup was 70%. The textile thus pretreated was then printed with an aqueous ink prepared in accordance with the procedure described above and containing 3.5% of the dye example 38, 2.5% of Disperbyk® 190 dispersant,
30% of 1,5-pentanediol,
5% of the diethylene glycol monomethyl ether,
0.01% of Mergal® K9N biocide and
58.99% of water
using a drop-on-demand (piezo) in jet print head. The print was fully dried. Fixing was effected by means of superheated steam at 175° C. for 7 minutes. The print was subsequently subjected to an alkaline reduction clear, rinsed warm and then dried.

APPLICATION EXAMPLE 4

A textile fabric consisting of polyester was padded with liquor consisting of 50 g/l of 8% sodium alginate solution, 100 g/l 8 to 12% carob flour ether solution and 5 g/l of monosodium phosphate in water and then dried. The wet pickup was 70%. The textile thus pretreated was then printed with an aqueous ink prepared in accordance with the procedure described above and containing 3.5% of the dye example 450, 2.5% of Disperbyk® 190 dispersant,
30% of 1,5-pentanediol,
5% of the diethylene glycol monomethyl ether,
0.01% of Mergal® K9N biocide and
58.99% of water
using a drop-on-demand (piezo) in jet print head. The print was fully dried. Fixing was effected by means of superheated steam at 175° C. for 7 minutes. The print was subsequently subjected to an alkaline reduction clear, rinsed warm and then dried.

COMPARISON EXAMPLE 1 a)

The build-up on standard 100% Polyester was measured for a dye of the present invention [Example 15] and for a commonly used dye [C.I. Disperse Red 369, formula (xc1)]. The results are compared and are as shown in FIG. 1

The dye according to Example 15 of the present invention has build-up on Toray polyester at 130° C. which is similar to the commercial product C.I. Disperse Red 369 (Comparison 1).

b)

The wet fastness on standard 100% polyester (exhaust dyed 130° C., post-set 30" 180° C.) was measured for the same dye of the present invention [Example 15] as in a) and for a the same commonly used dye [C.I. Disperse Red 369, formula (xc1)]. The results are compared

| Exhaust dyed 100% PES Toray | AATCC TM61 2A 49° C. | | ISO 105-C06 B2 | | Alk perspiration ISO 105 E04 | | Acid perspiration ISO 105 E04 | |
|---|---|---|---|---|---|---|---|---|
| | PES | PA | PES | PA | PES | PA | PES | PA |
| Comparison 1 (C.I. Disperse Red 369) | 4 | 3-4 | 4 | 4 | 3-4 | 3-4 | 4 | 3 |
| Example 15 | 5 | 5 | 5 | 5 | 5 | 5 | 5 | 4-5 |

From the data it is clear that the inventive dye of Example 15 has superior wet fastness properties compared to C.I. Disperse Red 369.

Thus it can be concluded that the inventive dyes have better wet fastness properties than the industry standard whilst they also maintain the same build-up properties.

COMPARISON EXAMPLE 2 a)

Figure 2:
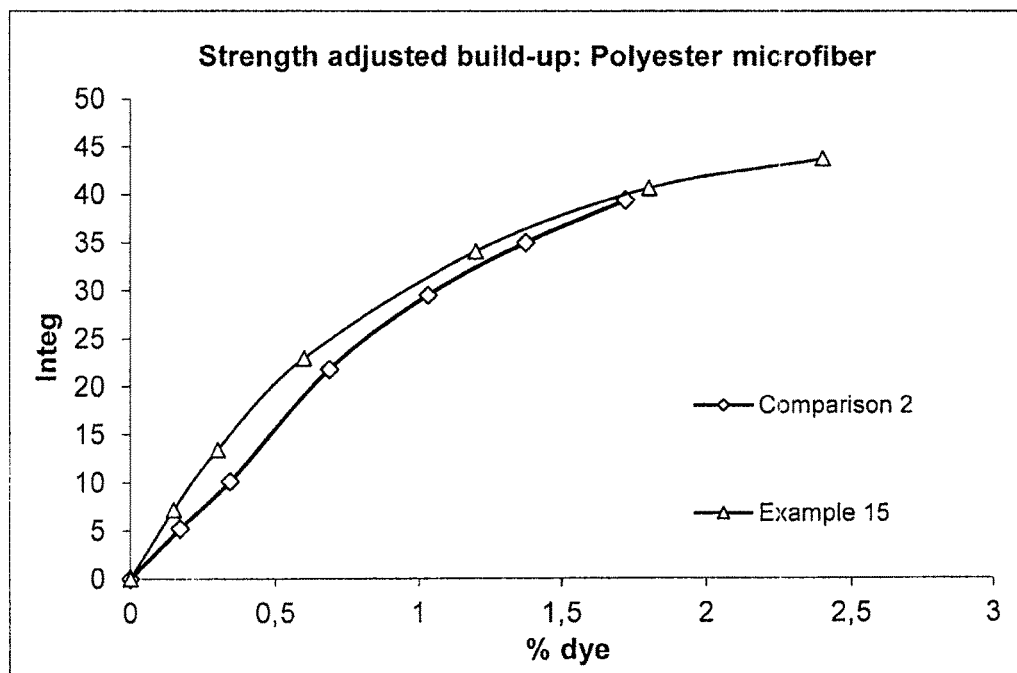
FIG. 2 illustrates the dye according to Example 15 of the present invention which has build-up on Toray polyester at 130° C. compared to Comparison 2.

The build-up on 100% polyester microfiber at 130° C. was measured for a dye of the present invention [Example 15] and for a commonly used dye [formula (xc2)]. The results are compared and are given in FIG. 2.

It can be seen that the dyes of the invention have a better build-up on polyester microfiber than the other industry standard for this colour.

b)

The wet fastness on polyester/cotton (dyed by Pad-Dry-Thermofix method 220° C.) of the same dyes as in a), i.e. [Expl. 15] and [formula xc2](comparison 2) was determined. Also the test was applied to the [C.I. Disperse Red 369] from Comparison Example 1 (comparison 3).

| Pad-dry-thermofix 220° C. | Combi test | |
|---|---|---|
| Polyester/cotton 65/35 | PES | CTN |
| Comparison 2 | 4 | 5 |
| Comparison 3 (C.I. Disperse Red 356) | 2-3 | 5 |
| Example 15 | 4-5 | 5 |

The inventive dye of Example 15 has better fastness compared to the dyes Comparison 2 and Comparison 3 (C.I. Disperse Red 356) in the Combination fastness test for polyester/cotton workwear (dry heat ISO 105 P01 5' 190° C., followed by wash ISO 105-C05 4 hrs 95° C.). Other wet fastness properties are similar.

It can therefore be summarized that the dyes of the present invention show the same or even better build-up properties than the dyes now used and at the same time have improved fastness properties.

The invention claimed is:

1. A dye of the formula (I) and mixtures thereof:

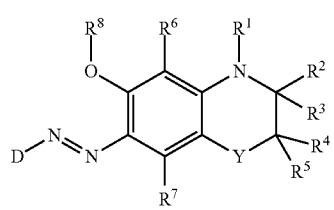

(I)

wherein
Y is a group of general formula (II) to (IV)

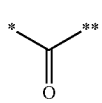

(II)

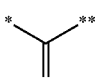

(III)

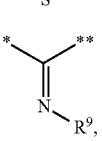

(IV)

$R^1$ is alkyl, alkenyl, cycloalkyl, aryl, heteroaryl or heterocycloalkyl,
or
alkyl interrupted by one or more heteroatoms selected from the group consisting of oxygen and sulphur,
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$,
or
alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, $R^2$ to $R^8$ independent of each other is hydrogen, alkyl, aryl, alkoxyl, cycloalkyl or halogen, or alkyl interrupted by one or more heteroatoms selected from the group consisting of oxygen and sulphur, or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, $R^9$ is alkyl, aryl, cycloalkyl or alkyl interrupted by one or more heteroatoms selected from the group consisting of oxygen and sulphur, or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diarylsulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diarylsulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N, N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, D represents a group of formula (VI)

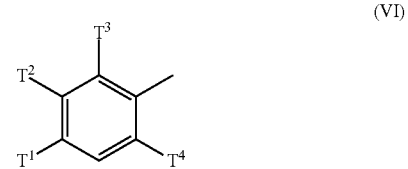

wherein $T^1$ to $T^4$ independent from each other is hydrogen, alkyl, cycloalkyl, alkenyl, alkynyl, aryl, alkoxyl, halogen, cyano, nitro, acyl, aryloyl, arylsulfonyl, alkylsulfonyl, N-monoalkyl-sulfamoyl, N,N-dialkyl-sulfamoyl, alkoxylcarbonyl, aryloxycarbonyl, N-monoalkyl-carbamoyl, N,N-dialkyl-carbamoyl, aryloyloxy, acyloxy, aryloxy, thiocyano, hydroxyl, arylmethoxy, arylsulphonyloxy, alkylsulphonyloxy, aryloxysulfonyl, -[(alkoxycarbonyl)-methoxyl]carbonyl, [(aryloxycarbonyl)-methoxyl]carbonyl, [(alkylacyl)-methoxy]carbonyl, [(arylacyl)-methoxy]carbonyl or trifluoromethyl, or alkyl interrupted by one or more heteroatoms selected from the group consisting of oxygen and sulfur, or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diarylsulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$, whereby at least one of $T^1$, $T^2$, $T^3$ and $T^4$ is not hydrogen,
or
D represents a group of formula (VII)

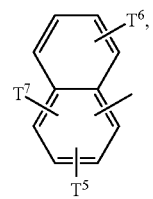

(VII)

wherein $T^5$ to $T^7$ independent from each other is hydrogen, alkyl, cycloalkyl, alkenyl, alkynyl, aryl, alkoxyl, halogen, cyano, nitro, acyl, arylacyl, alkoxycarbonyl, aryloxycarbonyl, [(alkoxycarbonyl)-methoxyl]carbonyl, [(aryloxycarbonyl)-methoxyl]carbonyl, [(alkylacyl)-methoxy]carbonyl, [(arylacyl)-methoxy]carbonyl, N-monoalkyl-carbamoyl or N,N-dialkyl-carbamoyl, or alkyl interrupted by one or more heteroatoms selected from the group consisting of oxygen and sulfur, or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkyl-sulphonyloxy, aryloxysulfonyl, alkoxylsulfonyl and COOR$^{12}$, whereby at least one of T$^5$, T$^6$ and T$^7$ is not hydrogen, or D represents a group of the formula (VIII)

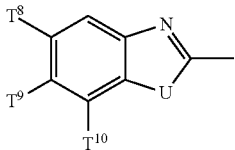
(VIII)

wherein

U is oxygen, sulphur or N—R$^{15}$,

T$^8$ and T$^{10}$ independent of each other is hydrogen, fluorine, chlorine or bromine, T$^9$ is hydrogen, alkylsulfonyl, thiocyano, alkoxy, halogen or nitro, R$^{15}$ is alkyl, aryl or cycloalkyl, or D represents a group of the formula (IX)

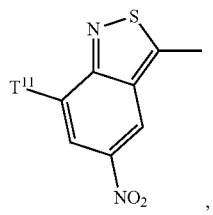
(IX)

wherein

T$^{11}$ is hydrogen, nitro or halogen, or

D represents a group of the formula (X)

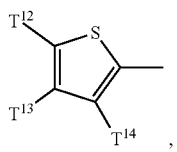
(X)

wherein

T$^{12}$ and T$^{14}$ independent from each other is nitro, cyano, acyl or alkoxycarbonyl, T$^{13}$ is hydrogen, aryl, alkyl or halogen, or alkyl interrupted by one or more heteroatoms selected from the group consisting of oxygen and sulfur, or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N, N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or D represents a group of the formula (XI)

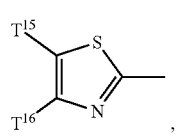

(XI)

wherein
$T^{15}$ and $T^{16}$ independent from each other is hydrogen, halogen, alkyl, nitro, cyano, acyl, alkoxycarbonyl or aryl,
or
alkyl interrupted by one or more heteroatoms selected from the group consisting of oxygen and sulfur,
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$,
or
alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$,
or
aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$,
whereby at least one of $T^{15}$ and $T^{16}$ is not hydrogen,
or
D represents a group of the formula (XII)

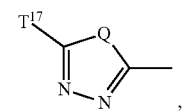

(XII)

wherein
$T^{17}$ is aryl or thioalkoxyl,
or
aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$, Q is oxygen or sulphur,
or
D represents a group of the formula (XIII)

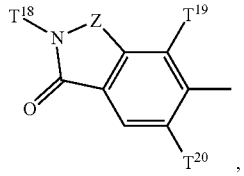
(XIII)

wherein
$T^{18}$ is alkyl, alkenyl or aryl,
or
alkyl interrupted by one or more heteroatoms selected from the group consisting of oxygen and sulfur,
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$
or
alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl, and COOR$^{12}$,
or
aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$,
$T^{19}$ and $T^{20}$ independent from each other is hydrogen, halogen, cyano, nitro or trifluoromethyl,
Z is a carbonyl or a sulfonyl,
or
D represents a group of the formula (XIV)

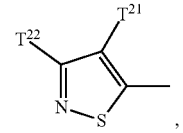
(XIV)

wherein
$T^{21}$ is cyano, nitro or alkoxycarbonyl,
$T^{22}$ is alkyl, hydrogen, halogen or aryl,
or
alkyl interrupted by one or more heteroatoms selected from the group consisting of oxygen and sulfur,
or
alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or alkyl interrupted by one or more heteroatoms selected from the group consisting of oxygen or sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$ or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, MN-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or D represents a group of the formula (XV)

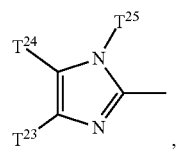

(XV)

wherein

T$^{23}$ and T$^{24}$ independent from each other is cyano, nitro, halogen, aryl or trifluoromethyl, T$^{25}$ is hydrogen, alkyl, alkenyl or aryl, or alkyl interrupted by one or more heteroatoms selected from the group consisting of oxygen and sulphur, or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or D represents a group of the formula (XVI)

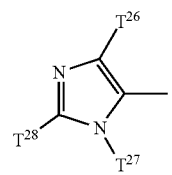

wherein $T^{26}$ is cyano, nitro, aryl or trifluoromethyl, $T^{27}$ is hydrogen, aryl or alkyl, or alkyl interrupted by one or more heteroatoms selected from the group consisting of oxygen and sulfur, or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, $T^{28}$ is hydrogen, alkyl, alkenyl, alkynyl, aryl or alkoxycarbonyl, or alkyl interrupted by one or more heteroatoms selected from the group consisting of oxygen and sulfur, or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N, N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diarylsulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diarylsulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or D represents a group of the formula (XVII)

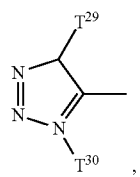

(XVII)

wherein $T^{29}$ is cyano, nitro, aryl or trifluoromethyl, $T^{30}$ is hydrogen, alkyl, alkenyl, alkenyl, alkynyl, aryl, arylmethyl or alkoxycarbonyl, or alkyl interrupted by one or more heteroatoms selected from the group consisting of oxygen and sulfur or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diarylsulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diarylsulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or D represents a group of the formula (XVIII)

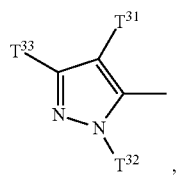

(XVIII)

wherein

T$^{31}$ is cyano, nitro, aryl or trifluoromethyl, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, T$^{32}$ is hydrogen, alkyl, alkenyl, alkynyl, aryl or alkoxycarbonyl, or alkyl interrupted by one or more heteroatoms selected from the group consisting of oxygen and sulphur, or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkyl-sulphonyloxy, aryloxysulfonyl, alkoxylsulfonyl and COOR$^{12}$, T$^{33}$ is hydrogen or alkyl or alkyl interrupted by one or more heteroatoms selected from the group consisting of oxygen and sulphur, or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or aryl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or D represents a group of the formula (XIX)

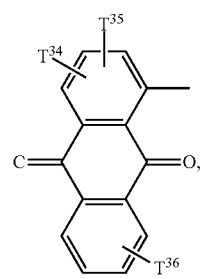

wherein

T$^{34}$, T$^{35}$ and T$^{36}$ independent from each other is hydrogen, halogen, nitro, cyano, hydroxyl, alkoxylcarbonyl, alkyl or acyl, or alkyl substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N,N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diaryl-sulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and COOR$^{12}$, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, amino, N-monoalkyl-amino, N,N-dialkyl-amino, N-monoaryl-amino, N,N-diaryl-amino, N-alkyl-N-aryl-amino, N-monocycloalkyl-amino, N,N-dicycloalkyl-amino, N-monoalkyl-monocycloalkyl-amino, N,N-monoaryl-monocycloalkyl-amino, N-acylamino, N-alkylsulfonyl-amino, halogen, cyano, thiocyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, N-monocycloalkyl-carbamoyl, N-monoalkyl-carbamoyl, N,N-dicycloalkyl-carbamoyl, N, N-dialkyl-carbamoyl, N-monoaryl-carbamoyl, N,N-diaryl-carbamoyl, N-monocycloalkyl-N-monoarylcarbamoyl, N-monoalkyl-N-monoaryl-carbamoyl, sulfamoyl, N-monocycloalkyl-sulfamoyl, N-monoalkyl-sulfamoyl, N,N-dicycloalkyl-sulfamoyl, N,N-dialkyl-sulfamoyl, N-monoaryl-sulfamoyl, N,N-diarylsulfamoyl, N-monocycloalkyl-N-monoarylsulfamoyl, N-monoalkyl-N-monoarylsulfamoyl, arylsulphonyloxy, alkylsulphonyloxy, aryloxysulfonyl, alkoxylsulfonyl and $COOR^{12}$, or D represents a group of the formula (XX)

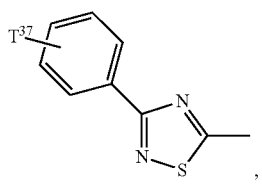

wherein $T^{37}$ is hydrogen, halogen or nitro, $R^{12}$ is hydrogen, alkyl, alkenyl, cycloalkyl, aryl, heteroaryl or heterocycloalkyl, or alkyl interrupted by one or more heteroatoms selected from the group consisting of oxygen and sulfur, or alkyl substituted by one or more substituents selected from the group consisting of hydroxy, aryl, cycloalkyl, alkoxy, thioalkoxy, halogen, cyano, amino, thiocyano, nitro, acyl, thioacyl, alkylsulfonyl, aryloyl, trifluoromethyl, heteroaryl, heterocycloalkyl, alkoxythiocarbonyl, acyloxy, aryloyloxy, carbamoyl, sulfamoyl, arylsulphonyloxy, alkylsulphonyloxy, aryloxysulfonyl and alkoxylsulfonyl, or alkyl interrupted by one or more heteroatoms selected from the group consisting of oxygen and sulphur and substituted by one or more substituents selected from the group consisting of hydroxy, aryl, cycloalkyl, alkoxy, thioalkoxy, halogen, cyano, amino, thiocyano, nitro, acyl, thioacyl, alkylsulfonyl, aryloyl, trifluoromethyl, heteroaryl, heterocycloalkyl, alkoxythiocarbonyl, acyloxy, aryloyloxy, carbamoyl, sulfamoyl, arylsulphonyloxy, alkylsulphonyloxy, aryloxysulfonyl and alkoxylsulfonyl, or aryl substituted by one or more substituents selected from the group consisting of hydroxy, aryl, cycloalkyl, alkoxy, thioalkoxy, amino, thiocyano, halogen, cyano, nitro, acyl, thioacyl, alkylsulfonyl, aryloyl, trifluoromethyl, heteroaryl, heterocycloalkyl, alkoxycarbonyl, alkoxythiocarbonyl, acyloxy, aryloyloxy, carbamoyl, sulfamoyl, arylsulphonyloxy, alkylsulphonyloxy, aryloxysulfonyl and alkoxylsulfonyl, with the proviso that when D represents a group of formula (XV) Y is carbonyl only and no fused-ring formation is allowed among $R^2$ to $R^{14}$.

2. The dye according to claim 1 having formula (I-a),

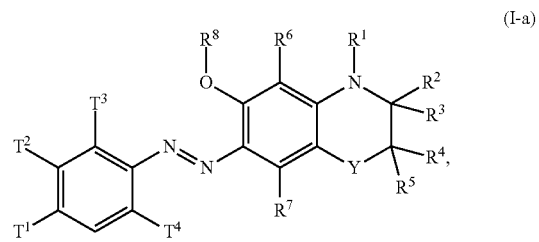

wherein each of $T^1$ to $T^4$ independent from each other is hydrogen, $(C_1-C_6)$-alkyl, $(C_3-C_6)$-cycloalkyl, substituted $(C_1-C_6)$-alkyl, $(C_3-C_4)$-alkenyl, $(C_3-C_4)$-alkynyl, aryl, O-interrupted $(C_1-C_6)$-alkyl, S-interrupted $(C_1-C_6)$-alkyl, $(C_1-C_8)$-alkoxyl, $(C_1-C_6)$-cycloalkyl, halogen, cyano, nitro, arylsulfonyl, arylsulfonyloxy, $(C_1-C_6)$-alkylsulfonyl, $(C_1-C_6)$-alkoxylsulfonyl, N—$(C_1-C_6)$-alkylsulfamoyl, N,N-bis$(C_1-C_6)$alkylsulfamoyl, N—$(C_1-C_6)$-alkyl carbamoyl, N-bis$(C_1-C_6)$alkyl-carbamoyl, $(C_1-C_6)$-alkylacyl, arylacyl, $(C_1-C_6)$-alkoxylcarbonyl, aryloxycarbonyl, thiocyano, hydroxyl, aryloxy, arylmethoxyl, aryloyloxy, arylsulfonyloxy, {([$(C_1-C_6)$-alkoxylcarbonyl]methoxyl} carbonyl, [(aryloxycarbonyl)methoxy] carbonyl, {[$(C_1-C_6)$-alkylacyl]-methoxy}carbonyl or [(arylacyl)-methoxy]carbonyl, $R^1$ is $(C_1-C_6)$-alkyl, $(C_1-C_6)$-acyloxy substituted $(C_2-C_6)$ alkyl, cyano$(C_1-C_6)$alkyl, arylmethyl, arylacyl $(C_1-C_6)$ alkyl, 2-$(C_1-C_6)$alkoxyl-2-oxoethyl, O-interrupted $(C_2-C_6)$-alkyl, S-interrupted $(C_2-C_6)$-alkyl, $(C_3-C_4)$-alkenyl, $(C_3-C_4)$-alkynyl, 3-$(C_1-C_6)$alkoxyl-3-oxopropyl, 3-[O-interrupted $(C_2-C_6)$-alkoxyl]-3-oxopropyl, 2-$(C_1-C_6)$alkoxyl-2-oxoethyl, 2-[O-interrupted $(C_2-C_6)$-alkoxyl]-2-oxoethyl, 2-{[$(C_1-C_6)$-alkylacyl]-methoxy}-2-oxoethyl, 3-{[$(C_1-C_6)$-alkylacyl]-methoxy}-3-oxopropyl, 2-[(arylacyl)-methoxy]-2-oxoethyl, 3-[(arylacyl)-methoxy]-3-oxopropyl, 3-{[$(C_1-C_6)$-alkoxylcarbonyl]-methoxy}-3-oxopropyl, 3-(arylmethoxy)-3-oxopropyl, 3-[(arylacyl)-methoxy]-3-oxopropyl, 2-(cyanomethoxy)-2-oxoethyl, 3-(cyanomethoxy)-3-oxopropyl, 2-{[$(C_1-C_6)$-alkoxylcarbonyl]methoxy}-2-oxoethyl, 1-[$(C_1-C_6)$-alkyl]-3-[$(C_1-C_6)$-alkoxyl]-3-oxopropyl, 1-[$(C_1-C_6)$-alkyl]-3-[O-interrupted $(C_1-C_6)$-alkoxyl]-3-oxopropyl, 1-[$(C_1-C_6)$-alkyl]-3-(arylmethoxyl)-3-oxopropyl, —[$(C_1-C_6)$-alkyl]-3-{[$(C_1-C_6)$-alkylacyl]methoxy}-3-oxopropyl or 1-[$(C_1-C_6)$-alkyl]-3-{[$(C_1-C_6)$-alkoxylcarbonyl]-methoxy}-3-oxopropyl, $R^2$ to $R^7$ independent from each other is hydrogen, $(C_1-C_6)$alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl, and Y is carbonyl.

3. The dye according to claim 2 having formula (I-a), wherein

T$^1$, T$^3$ and T$^4$ independent from each other is hydrogen, nitro, cyano, bromine, chlorine, benzoxyl, phenoxy, methoxy, ethoxy, methyl, trifluromethyl, ethyl, benzoyl, acetyl, hydroxyl, methoxycarbonyl, ethoxycarbonyl, methylsulfonyl, cyanomethylsulfonyl, acetonylsulfonyl, (2-ethoxy-2-oxoethyl)sulfonyl, (2-methoxy-2-oxoethyl)sulfonyl, phenylsulfonyloxy, phenoxylsulfonyl, ethoxylsulfonyl, phenoxylsulfonyl cyanomethoxylcarbonyl, (2-ethoxy-2-oxoethyl)carbonyl, (2-methoxy-2-oxoethyl)carbonyl, acetonylcarbonyl or phenacylcarbonyl, T$^2$ is hydrogen, chlorine, bromine, methoxy, ethoxy, phenoxy, benzoxy, nitro, methyl or ethyl, R$^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-(C$_1$-C$_6$) alkoxyl-3-oxopropyl, 3-[O-interrupted (C$_2$-C$_6$)-alkoxyl]-3-oxopropyl, 2-(C$_1$-C$_6$)alkyl-2-oxoethyl, 2-[O-interrupted (C$_2$-C$_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[(C$_1$-C$_6$)alkylacyl]-methoxyl}-3-oxopropyl, 3-[(arylacyl)-methoxy]-3-oxopropyl, 3-{[(C$_1$-C$_6$)-alkoxycabonyl]methoxy}-3-oxopropyl, 2-{[(C$_1$-C$_6$)-alkoxycabonyl]methoxy}-2-oxoethyl or 2-{[(C$_1$-C$_6$) alkylacyl]-methoxyl}2-oxoethyl, R$^2$ to R$^7$ independent from each other is hydrogen, bromine, chlorine, ethyl or methyl, R$^8$ is hydrogen, methyl, ethyl, propyl, isopropyl, 2-ethoxy-2-oxoethyl or 2-methoxy-2-oxoethyl and Y is carbonyl.

4. The dye according to claim 1 having formula (I-b)

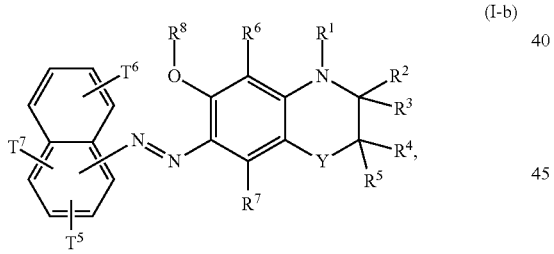

(I-b)

wherein

T$^5$ to T$^7$ independent from each other is hydrogen, (C$_1$-C$_6$)alkyl, (C$_3$-C$_8$)cycloalkyl, O-interrupted (C$_1$-C$_6$)-alkyl, S-interrupted (C$_1$-C$_6$)-alkyl, aryl, (C$_1$-C$_6$) alkoxyl, halogen, cyano, nitro, (C$_1$-C$_6$)-alkylacyl, arylacyl, (C$_1$-C$_6$)-alkoxycarbonyl, aryloxycarbonyl, N—(C$_1$-C$_6$)-alkyl carbamoyl, or N,N-bis(C$_1$-C$_6$)-alkyl carbamoyl, whereby at least one of T$^5$, T$^6$ and T$^7$ is not hydrogen, R$^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-(C$_1$-C$_6$) alkoxyl-3-oxopropyl, 3-[O-interrupted (C$_2$-C$_6$)-alkoxyl]-3-oxopropyl, 2-(C$_1$-C$_6$)alkyl-2-oxoethyl, 2-[O-interrupted (C$_2$-C$_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[(C$_1$-C$_6$)alkylacyl]-methoxyl}-3-oxopropyl, 3-[(arylacyl)-methoxy]-3-oxopropyl, 3-{[(C$_1$-C$_6$)-alkoxycabonyl]methoxy}-3-oxopropyl, 2-{[(C$_1$-C$_6$)-alkoxycabonyl]methoxy}-2-oxoethyl or 2-{[(C$_1$-C$_6$) alkylacyl]-methoxyl}-2-oxoethyl, R$^2$ to R$^7$ independent from each other is hydrogen, (C$_1$-C$_6$)alkyl, aryl, (C$_1$-C$_8$)alkoxyl, (C$_3$-C$_8$)cycloalkyl, O-interrupted (C$_2$-C$_6$)alkyl, S-interrupted (C$_2$-C$_6$)alkyl or halogen, R$^8$ is hydrogen, (C$_1$-C$_6$)alkyl, (C$_3$-C$_4$)-alkenyl, (C$_3$-C$_4$)-alkynyl, arylmethyl, 2-(C$_1$-C$_6$)alkoxyl-2-oxoethyl, 2-(arylmethyl)-2-oxoethyl, cyano(C$_1$-C$_6$)alkyl, O-interrupted (C$_1$-C$_6$)alkyl or S-interrupted (C$_1$-C$_6$)alkyl and Y is carbonyl.

5. The dye according to claim 1 having formula (I-c)

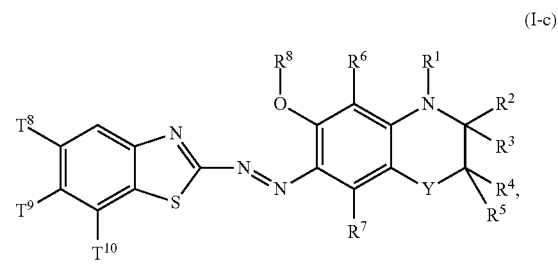

(I-c)

wherein

T$^8$ and T$^{10}$ independent from each other is hydrogen, chlorine or bromine, T$^9$ is hydrogen, (C$_1$-C$_6$)-alkylsulfonyl, thiocyano, (C$_1$-C$_6$)-alkoxy, chlorine or nitro, R$^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-(C$_1$-C$_6$) alkoxyl-3-oxopropyl, 3-[O-interrupted (C$_2$-C$_6$)-alkoxyl]-3-oxopropyl, 2-(C$_1$-C$_6$)alkyl-2-oxoethyl, 2-[O-interrupted (C$_2$-C$_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[(C$_1$-C$_6$)alkylacyl]-methoxyl}-3-oxopropyl, 3-[(arylacyl)-methoxy]-3-oxopropyl, 3-{[(C$_1$-C$_6$)-alkoxycabonyl]methoxy}-3-oxopropyl, 2-{[(C$_1$-C$_6$)-alkoxycabonyl]methoxy}-2-oxoethyl or 2-{[(C$_1$-C$_6$) alkylacyl]-methoxyl}-2-oxoethyl, R$^2$ to R$^7$ independent from each other is hydrogen, (C$_1$-C$_6$)alkyl, aryl, (C$_1$-C$_8$)alkoxyl, (C$_3$-C$_8$)cycloalkyl, O-interrupted (C$_2$-C$_6$)alkyl, S-interrupted (C$_2$-C$_6$)alkyl or halogen, R$^8$ is hydrogen, (C$_1$-C$_6$)alkyl, (C$_3$-C$_4$)-alkenyl, (C$_3$-C$_4$)-alkynyl, arylmethyl, 2-(C$_1$-C$_6$)alkoxyl-2-oxoethyl, 2-(arylmethyl)-2-oxoethyl, cyano(C$_1$-C$_6$)alkyl, O-interrupted (C$_1$-C$_6$)alkyl or S-interrupted (C$_1$-C$_6$)alkyl and Y is carbonyl.

6. The dye according to claim 1 having formula (I-d)

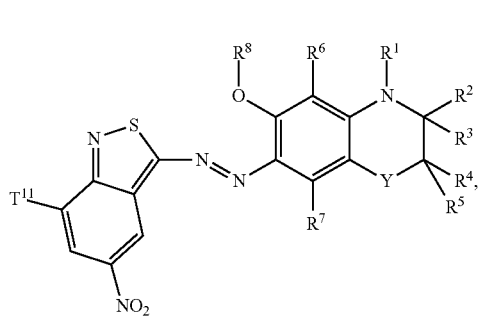

(I-d)

wherein $T^{11}$ is hydrogen, nitro or bromine, $R^1$ is methyl, ethyl, propyl, isopropyl, n-butyl, isobutyl, benzyl, 2-methoxyethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-($C_1$-$C_6$) alkoxyl-3-oxopropyl, 3-[O-interrupted ($C_2$-$C_6$)-alkoxyl]-3-oxopropyl, 2-($C_1$-$C_6$)alkyl-2-oxoethyl, 2-[O-interrupted ($C_2$-$C_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[($C_1$-$C_6$)alkylacyl]-methoxyl}-3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)-alkoxycabonyl]methoxy}-2-oxoethyl or 2-{[($C_1$-$C_6$) alkylacyl]-methoxyl}2-oxoethyl, $R^2$ to $R^7$ independent from each other is hydrogen, ($C_1$-$C_6$)alkyl, aryl, ($C_1$-$C_8$)alkoxyl, ($C_3$-$C_8$)cycloalkyl, O-interrupted ($C_2$-$C_6$)alkyl, S-interrupted ($C_2$-$C_6$)alkyl or halogen, $R^8$ is hydrogen, ($C_1$-$C_6$)alkyl, ($C_3$-$C_4$)-alkenyl, ($C_3$-$C_4$)-alkynyl, arylmethyl, 2-($C_1$-$C_6$)alkoxyl-2-oxoethyl, 2-(arylmethyl)-2-oxoethyl, cyano($C_1$-$C_6$)alkyl, O-interrupted ($C_1$-$C_6$)alkyl or S-interrupted ($C_1$-$C_6$)alkyl and Y is carbonyl.

7. The dye according to claim 1 having formula (I-e)

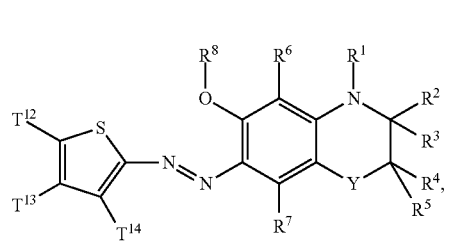

(I-e)

wherein $T^{12}$ and $T^{14}$ independent from each other, are nitro, cyano, formyl, acetyl or ($C_1$-$C_6$)-alkoxycarbonyl, $T^{13}$ is hydrogen, aryl, ($C_1$-$C_6$)-alkyl or halogen, $R^1$ is methyl, ethyl, propyl, isopropyl, n-butyl, isobutyl, benzyl, 2-methoxyethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-($C_1$-$C_6$) alkoxyl-3-oxopropyl, 3-[O-interrupted ($C_2$-$C_6$)-alkoxyl]-3-oxopropyl, 2-($C_1$-$C_6$)alkyl-2-oxoethyl, 2-[O-interrupted ($C_2$-$C_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[($C_1$-$C_6$)alkylacyl]-methoxyl}-3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)-alkoxycabonyl]methoxy}-2-oxoethyl or 2-{[($C_1$-$C_6$) alkylacyl]-methoxyl}-2-oxoethyl, $R^2$ to $R^7$ independent from each other is hydrogen, ($C_1$-$C_6$)alkyl, aryl, ($C_1$-$C_8$)alkoxyl, ($C_3$-$C_8$)cycloalkyl, O-interrupted ($C_2$-$C_6$)alkyl, S-interrupted ($C_2$-$C_6$)alkyl or halogen, $R^8$ is hydrogen, ($C_1$-$C_6$)alkyl, ($C_3$-$C_4$)-alkenyl, ($C_3$-$C_4$)-alkynyl, arylmethyl, 2-($C_1$-$C_6$)alkoxyl-2-oxoethyl, 2-(arylmethyl)-2-oxoethyl, cyano($C_1$-$C_6$)alkyl, O-interrupted ($C_1$-$C_6$)alkyl or S-interrupted ($C_1$-$C_6$)alkyl and Y is carbonyl.

8. The dye according to claim 1 having formula (I-f)

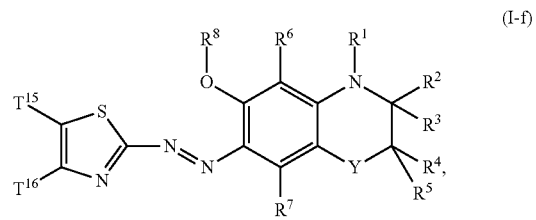

(I-f)

wherein $T^{15}$ and $T^{16}$ independent from each other is hydrogen, halogen, ($C_1$-$C_6$)-alkyl, nitro, cyano, formyl, acetyl, ($C_1$-$C_6$)-alkoxycarbonyl, O-interrupted ($C_1$-$C_6$)-alkyl, S-interrupted ($C_1$-$C_6$)-alkyl or aryl, $R^1$ is methyl, ethyl, propyl, isopropyl, n-butyl, isobutyl, benzyl, 2-methoxyethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-($C_1$-$C_6$) alkoxyl-3-oxopropyl, 3-[O-interrupted ($C_2$-$C_6$)-alkoxyl]-3-oxopropyl, 2-($C_1$-$C_6$)alkyl-2-oxoethyl, 2-[O-interrupted ($C_2$-$C_6$)-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[($C_1$-$C_6$)alkylacyl]-methoxyl}-3-oxopropyl, 3-[(arylacyl)-methoxy]-3-oxopropyl, 3-{[($C_1$-$C_6$)-alkoxycabonyl]methoxy}-3-oxopropyl, 2-{[($C_1$-$C_6$)-alkoxycabonyl]methoxy}-2-oxoethyl or 2-{[($C_1$-$C_6$) alkylacyl]-methoxyl}-2-oxoethyl, $R^2$ to $R^7$ independent from each other is hydrogen, ($C_1$-$C_6$)alkyl, aryl, ($C_1$-$C_8$)alkoxyl, ($C_3$-$C_8$)cycloalkyl, O-interrupted ($C_2$-$C_6$)alkyl, S-interrupted ($C_2$-$C_6$)alkyl or halogen, $R^8$ is hydrogen, ($C_1$-$C_6$)alkyl, ($C_3$-$C_4$)-alkenyl, ($C_3$-$C_4$)-alkynyl, arylmethyl, 2-($C_1$-$C_6$)alkoxyl-2-oxoethyl, 2-(arylmethyl)-2-oxoethyl, cyano($C_1$-$C_6$)alkyl, O-interrupted ($C_1$-$C_6$)alkyl or S-interrupted ($C_1$-$C_6$)alkyl and Y is carbonyl.

9. The dye according to claim 1 having formula (I-g)

(I-g)

wherein $T^{17}$ is aryl or $(C_1-C_6)$-thioalkoxyl,

Q is oxygen or sulphur, $R^1$ is methyl, ethyl, propyl, isopropyl, n-butyl, isobutyl, benzyl, 2-methoxyethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$ alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy)}-3-oxopropyl, 2-{[$(C_1-C_6)$-alkoxycabonyl]methoxy}-2-oxoethyl or 2-{[$(C_1-C_6)$ alkylacyl]-methoxyl}-2-oxoethyl, $R^2$ to $R^7$ independent from each other is hydrogen, $(C_1-C_6)$alkyl, aryl, $(C_1-C_8)$alkoxyl, $(C_3-C_8)$cycloalkyl, O-interrupted $(C_2-C_6)$alkyl, S-interrupted $(C_2-C_6)$ alkyl, halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

10. The dye according to claim 1 having formula (I-h)

(I-h)

wherein $T^{18}$ is $(C_1-C_6)$-alkyl, $(C_1-C_6)$-acyloxy substituted $(C_1-C_6)$-alkyl, cyano$(C_1-C_6)$-alkyl, arylmethyl, arylcarbonyl substituted $(C_1-C_6)$-alkyl, 2-$(C_1-C_6)$-alkoxyl-2-oxoethyl, O-interrupted $(C_1-C_6)$-alkyl, S-interrupted $(C_1-C_6)$-alkyl or aryl, $T^{19}$ and $T^{20}$ independent from each other are hydrogen, halogen, cyano, nitro or trifluoromethyl, Z is a carbonyl or a sulfonyl rest, $R^1$ is methyl, ethyl, propyl, isopropyl, n-butyl, isobutyl, benzyl, 2-methoxyethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$ alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$ alkylacyl]-methoxyl}-2-oxoethyl, $R^2$ to $R^7$ independent from each other is hydrogen, $(C_1-C_6)$alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

11. The dye according to claim 1 having formula (I-i)

(I-i)

wherein $T^{21}$ is cyano, nitro or $(C_1-C_6)$-alkoxycarbonyl, $T^{22}$ is $(C_1-C_6)$-alkyl, hydrogen, halogen or aryl, $R^1$ is methyl, ethyl, propyl, isopropyl, n-butyl, isobutyl, benzyl, 2-methoxyethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$ alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$ alkylacyl]-methoxyl}-2-oxoethyl, $R^2$ to $R^7$ independent from each other is hydrogen, $(C_1-C_6)$alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

12. The dye according to claim 1 having formula (I-j)

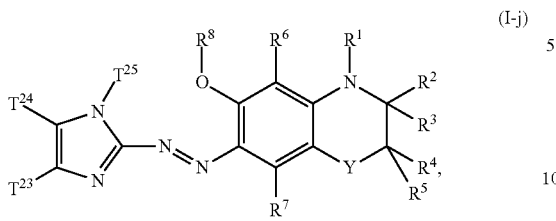

wherein $T^{23}$ and $T^{24}$ independent from each other is cyano, nitro, halogen, aryl or trifluoromethyl, $T^{25}$ is hydrogen, $(C_1-C_6)$-alkyl, O-interrupted $(C_1-C_6)$-alkyl, S-interrupted $(C_1-C_6)$-alkyl or aryl, $R^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$ alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$alkylacyl]-methoxyl}-2-oxoethyl, Each of $R^2$ to $R^7$, independent from each other, is hydrogen, $(C_1-C_6)$alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

13. The dye according to claim 1 having formula (I-k)

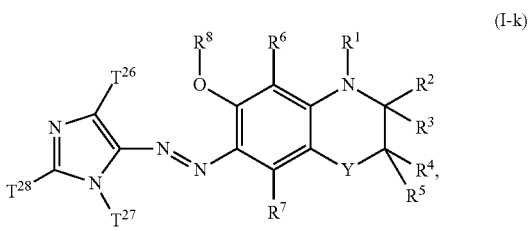

wherein $T^{26}$ is cyano, nitro, aryl or trifluoromethyl, $T^{27}$ is hydrogen, aryl or $(C_1-C_6)$-alkyl, $T^{28}$ is hydrogen, $(C_1-C_6)$-acyloxy substituted $(C_1-C_6)$ alkyl, cyano$(C_1-C_6)$alkyl, aryl, O-interrupted $(C_1-C_6)$-alkyl or S-interrupted $(C_1-C_6)$-alkyl, $R^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$ alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$alkylacyl]-methoxyl}-2-oxoethyl, $R^2$ to $R^7$ independent from each other is hydrogen, $(C_1-C_6)$alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

14. The dye according to claim 1 having formula (I-l)

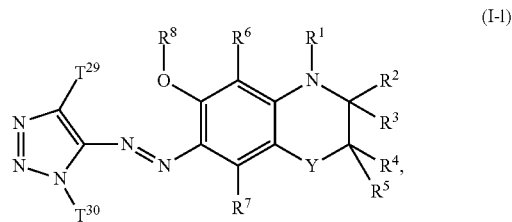

wherein $T^{29}$ is cyano, nitro, aryl or trifluoromethyl, $T^{30}$ is hydrogen, $(C_1-C_6)$-alkyl, cyano$(C_1-C_6)$alkyl, O-interrupted $(C_1-C_6)$alkyl, S-interrupted $(C_1-C_6)$alkyl, aryl, benzyl, $(C_1-C_6)$-acyloxy substituted $(C_1-C_6)$alkyl or cyano$(C_1-C_6)$alkyl, $R^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$ alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$alkylacyl]-methoxyl}-2-oxoethyl, $R^2$ to $R^7$ independent from each other is hydrogen, $(C_1-C_6)$alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

15. The dye according to claim 1 having formula (I-m)

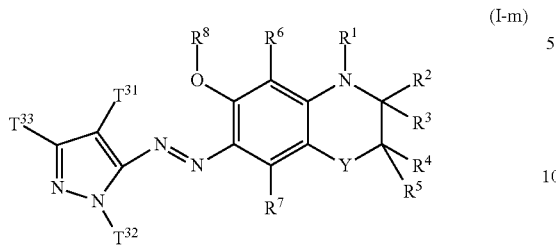

wherein $T^{31}$ is cyano, nitro, aryl or trifluoromethyl, $T^{32}$ is hydrogen, $(C_1-C_6)$-alkyl, O-interrupted $(C_1-C_6)$-alkyl, S-interrupted $(C_1-C_6)$-alkyl, cyano$(C_1-C_6)$alkyl, arylmethyl, cyano$(C_1-C_6)$alkyl or $(C_1-C_6)$-acyloxy substituted $(C_1-C_6)$alkyl, $T^{33}$ is hydrogen or $(C_1-C_6)$alkyl, $R^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$ alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$ alkylacyl]-methoxyl}-2-oxoethyl, $R^2$ to $R^7$ independent from each other is hydrogen, $(C_1-C_6)$alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

16. The dye according to claim 1 having formula (I-n)

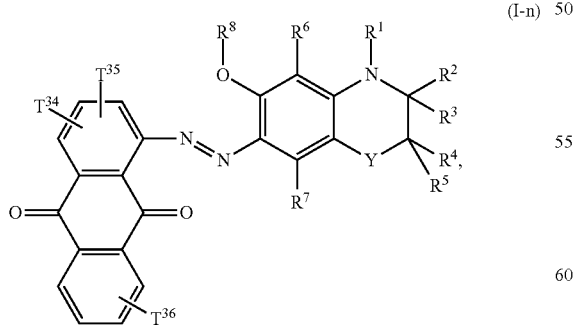

wherein $T^{34}$, $T^{35}$ and $T^{36}$ independent from each other is hydrogen, halogen, nitro, cyano, hydroxyl, $(C_1-C_6)$-alkoxylcarbonyl, $(C_1-C_6)$-alkyl or acyl, $R^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$ alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$ alkylacyl]-methoxyl}-2-oxoethyl, $R^2$ to $R^7$ independent from each other is hydrogen, $(C_1-C_6)$alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

17. The dye according to claim 1 having formula (I-o)

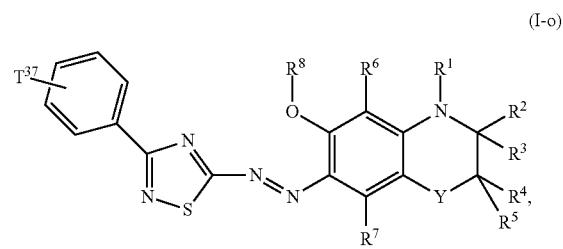

wherein $T^{37}$ is nitro, hydrogen or halogen, $R^1$ is methyl, ethyl, propyl, isopropyl, n-butyl, isobutyl, benzyl, 2-methoxylethyl, 2-ethoxylethyl, 2-acetoxyethyl, 2-(propionyl)oxyethyl, 2-(benzoyl)oxyethyl, cyanomethyl, 2-cyanoethyl, 3-cyanopropyl, 3-$(C_1-C_6)$ alkoxyl-3-oxopropyl, 3-[O-interrupted $(C_2-C_6)$-alkoxyl]-3-oxopropyl, 2-$(C_1-C_6)$alkyl-2-oxoethyl, 2-[O-interrupted $(C_2-C_6)$-alkoxyl]-2-oxoethyl, 2-(cyanomethoxy)-2-oxoethyl, 3-(cyanomethoxy)-3-oxopropyl, 2-[(arylacyl)methoxy]-2-oxoethyl, 3-[(arylacyl)methoxy]-3-oxopropyl, 3-(arylmethoxy)-3-oxopropyl, 3-{[$(C_1-C_6)$alkylacyl]-methoxyl}-3-oxopropyl, 3-[(arylacyl)-methoxy]-3-oxopropyl, 3-{[$(C_1-C_6)$-alkoxycabonyl]methoxy}-3-oxopropyl, 2-{[$(C_1-C_6)$-alkoxycabonyl]methoxy}-2-oxoethyl or 2-{[$(C_1-C_6)$ alkylacyl]-methoxyl}-2-oxoethyl, $R^2$ to $R^7$ independent from each other is hydrogen, $(C_1-C_6)$alkyl, aryl, $(C_1-C_8)$alkoxyl, $(C_3-C_8)$cycloalkyl, O-interrupted $(C_2-C_6)$alkyl, S-interrupted $(C_2-C_6)$alkyl or halogen, $R^8$ is hydrogen, $(C_1-C_6)$alkyl, $(C_3-C_4)$-alkenyl, $(C_3-C_4)$-alkynyl, arylmethyl, 2-$(C_1-C_6)$alkoxyl-2-oxoethyl, 2-(arylmethyl)-2-oxoethyl, cyano$(C_1-C_6)$alkyl, O-interrupted $(C_1-C_6)$alkyl or S-interrupted $(C_1-C_6)$alkyl and Y is carbonyl.

18. A process for the production of the dye as claimed in claim 1 and mixtures thereof, comprising
   a) diazotization of a compound of the general formula (XD)

$$D\text{-}NH_2 \quad (XD),$$

wherein
   D is as defined in claim 1, and
   b) reacting the obtained corresponding diazonium salt with a compound of formula (XC)

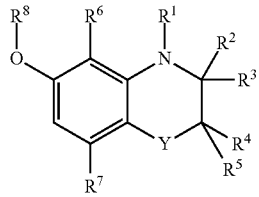

(XC)

wherein $R^1$ to $R^8$ and Y are each as defined in claim 1.

19. A process of dyeing and printing a hydrophobic material which comprises contacting the material with the dye according to claim 1.

* * * * *